US012667361B2

(12) United States Patent
Marmor et al.

(10) Patent No.: US 12,667,361 B2
(45) Date of Patent: Jun. 30, 2026

(54) DEVICES, SYSTEMS, AND METHODS FOR MANAGING BLOOD FLOW

(71) Applicant: REVASCARDIO LTD., Ra'anana (IL)

(72) Inventors: Shahaf Marmor, Tel Aviv (IL); Oded Meiri, Ram-On (IL); Assaf Alon, Elkana (IL); Chaim Zeev Aber, Ra'anana (IL); David Shlomo Chayen, Tel Aviv (IL)

(73) Assignee: REVASCARDIO LTD., Ra'anana (IL)

( * ) Notice: Subject to any disclaimer, the term of this patent is extended or adjusted under 35 U.S.C. 154(b) by 0 days.

(21) Appl. No.: 19/386,177

(22) Filed: Nov. 11, 2025

(65) Prior Publication Data

US 2026/0060685 A1     Mar. 5, 2026

Related U.S. Application Data

(63) Continuation of application No. 19/098,279, filed on Apr. 2, 2025, now Pat. No. 12,490,989.

(30) Foreign Application Priority Data

| Apr. 2, 2024 | (IL) | ......................................... | 311902 |
| Sep. 7, 2024 | (IL) | ......................................... | 315496 |

(51) Int. Cl.
  *A61B 17/12*     (2006.01)
  *A61B 17/00*     (2006.01)
  (Continued)

(52) U.S. Cl.
  CPC ................. *A61B 17/12036* (2013.01); *A61B 17/00234* (2013.01); *A61B 17/12122* (2013.01);
  (Continued)

(58) Field of Classification Search
  CPC ........ A61B 17/00234; A61B 17/12122; A61B 90/06; A61B 2017/00252;
  (Continued)

(56) References Cited

U.S. PATENT DOCUMENTS

| 4,934,996 A | * | 6/1990 | Mohl | .................... | A61M 25/04 |
| | | | | | 604/920 |
| 6,503,272 B2 | | 1/2003 | Duerig et al. | | |

(Continued)

FOREIGN PATENT DOCUMENTS

| IL | 151931 A | 2/2012 |
| WO | 1998046115 A2 | 10/1998 |

(Continued)

OTHER PUBLICATIONS

International Search Report and Written Opinion for International Application No. PCT/IB202/053433, dated Jun. 2, 2025 (16 pages).

*Primary Examiner* — Susan S Su
*Assistant Examiner* — Erin A Kim
(74) *Attorney, Agent, or Firm* — Finnegan, Henderson, Farabow, Garrett & Dunner LLP

(57) ABSTRACT

Devices, systems, and methods for causing retrograde oxygenated blood flow in at least a portion of the venous system of the myocardium are disclosed. Devices and methods include a method for causing retrograde oxygenated blood flow in at least a portion of the venous system of the myocardium, the method comprising: implanting a variable occluder in a coronary sinus region proximate a left atrium, wherein the variable occluder is configured to gradually increase a level of blood flow restriction over a period of days to enable a venous system of the myocardium to compensate for increased pressure caused by the gradual increase in the level of blood flow restriction; and following venous system compensation, shunting oxygenated blood flow into the coronary sinus to cause retrograde flow of oxygenated blood in at least a portion of the venous system of the myocardium to thereby enable revascularization of the myocardium.

26 Claims, 22 Drawing Sheets

(51) Int. Cl.
| | |
|---|---|
| *A61B 17/34* | (2006.01) |
| *A61B 90/00* | (2016.01) |
| *A61M 27/00* | (2006.01) |

(52) U.S. Cl.
CPC ........ *A61B 17/12172* (2013.01); *A61B 17/34* (2013.01); *A61B 90/06* (2016.02); *A61M 27/002* (2013.01); *A61B 2017/00022* (2013.01); *A61B 2017/00252* (2013.01); *A61B 2090/064* (2016.02); *A61M 2205/04* (2013.01); *A61M 2205/3331* (2013.01); *A61M 2210/125* (2013.01)

(58) Field of Classification Search
CPC ........ A61B 17/12036; A61M 2205/04; A61M 2205/3331; A61M 2210/125
See application file for complete search history.

(56) References Cited

U.S. PATENT DOCUMENTS

| | | | |
|---|---|---|---|
| 6,569,145 | B1 | 5/2003 | Shmulewitz et al. |
| 10,092,295 | B2 | 10/2018 | Bödewadt et al. |
| 12,490,989 | B2 * | 12/2025 | Marmor ........... A61B 17/12036 |
| 2002/0062146 | A1 | 5/2002 | Makower et al. |
| 2006/0106449 | A1 | 5/2006 | Muvhar |
| 2013/0304196 | A1 | 11/2013 | Kelly |
| 2017/0106176 | A1 * | 4/2017 | Taft ..................... A61M 27/008 |
| 2023/0346381 | A1 | 11/2023 | Quadri et al. |
| 2024/0252319 | A1 | 8/2024 | Matheny |

FOREIGN PATENT DOCUMENTS

| | | |
|---|---|---|
| WO | 2024191842 A1 | 9/2024 |
| WO | 2024249425 A1 | 12/2024 |

* cited by examiner

306A

306A

110

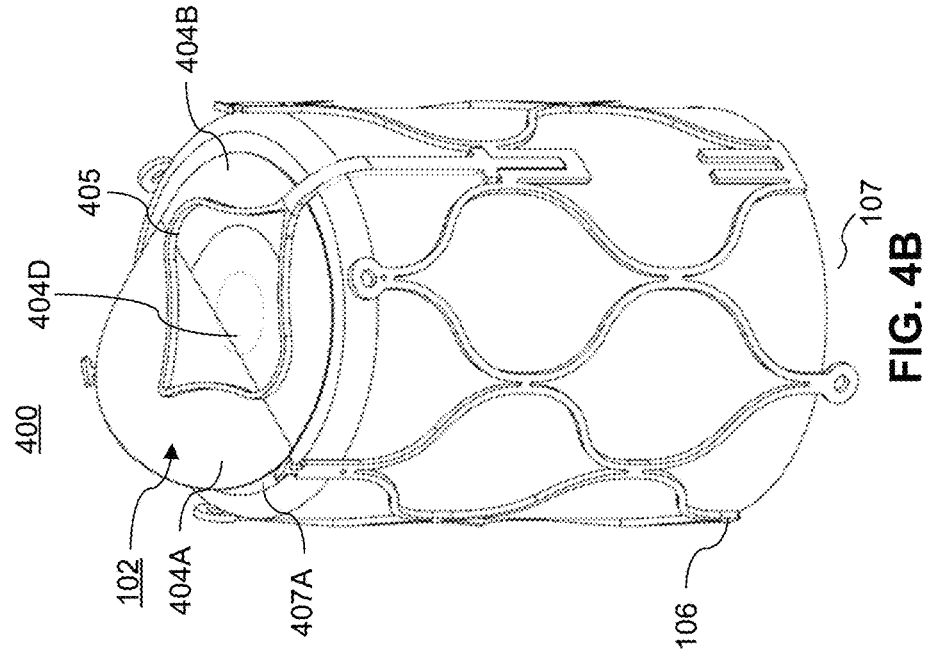
FIG. 4B
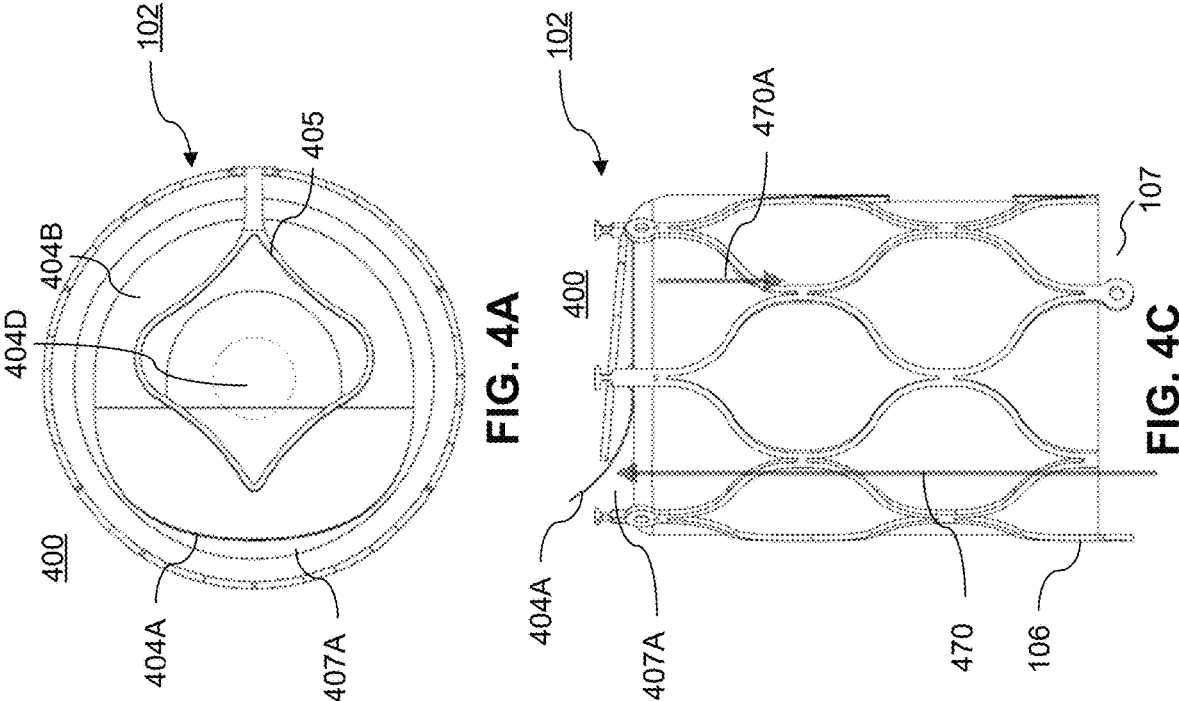
FIG. 4A
FIG. 4C

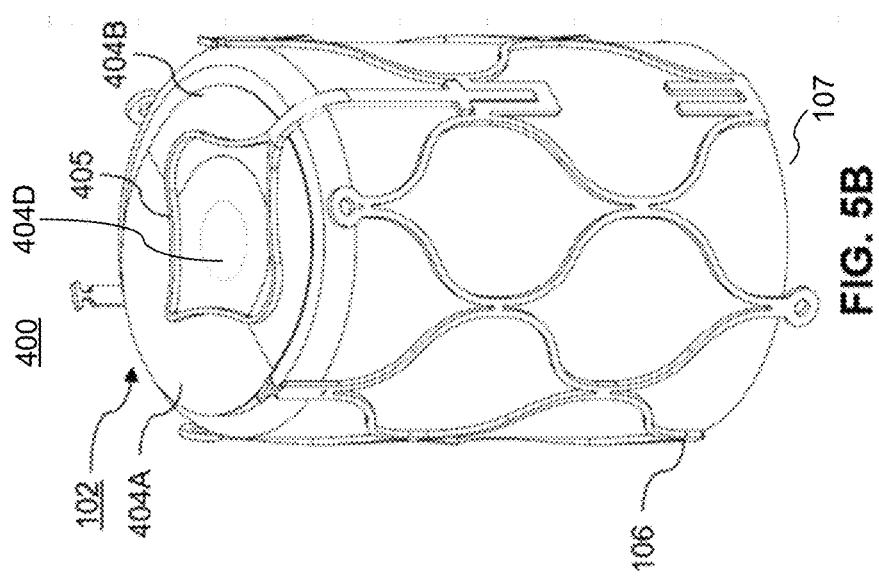
FIG. 5B
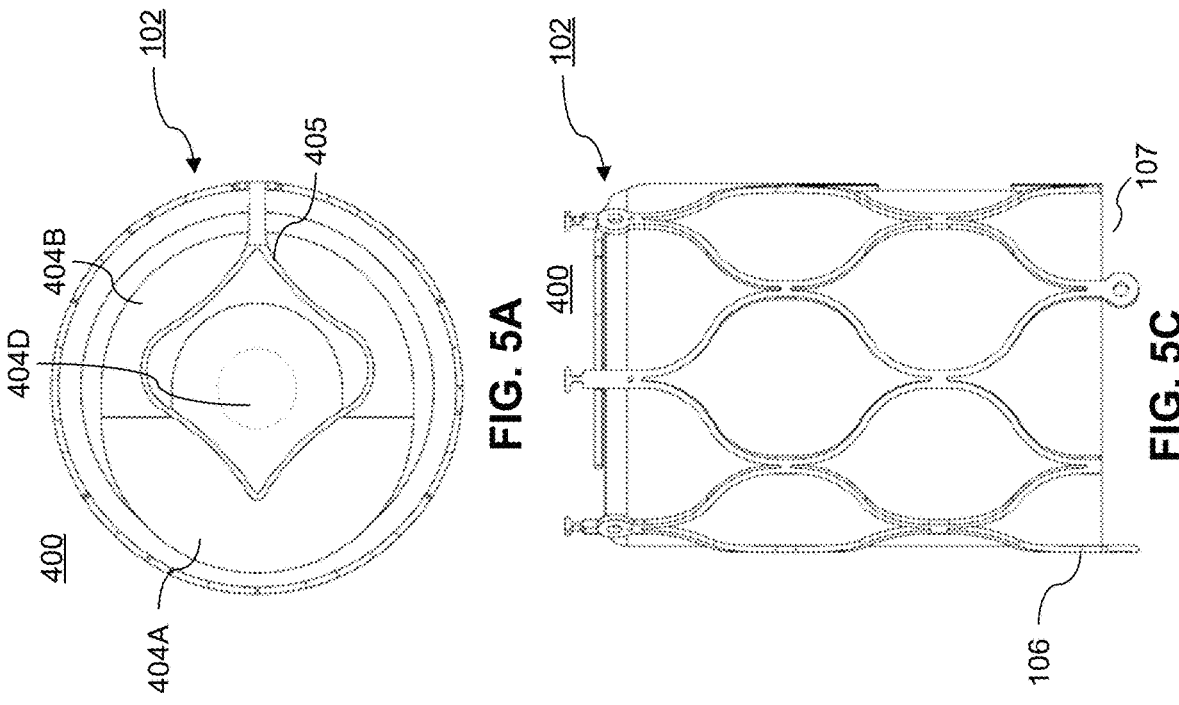
FIG. 5A
FIG. 5C

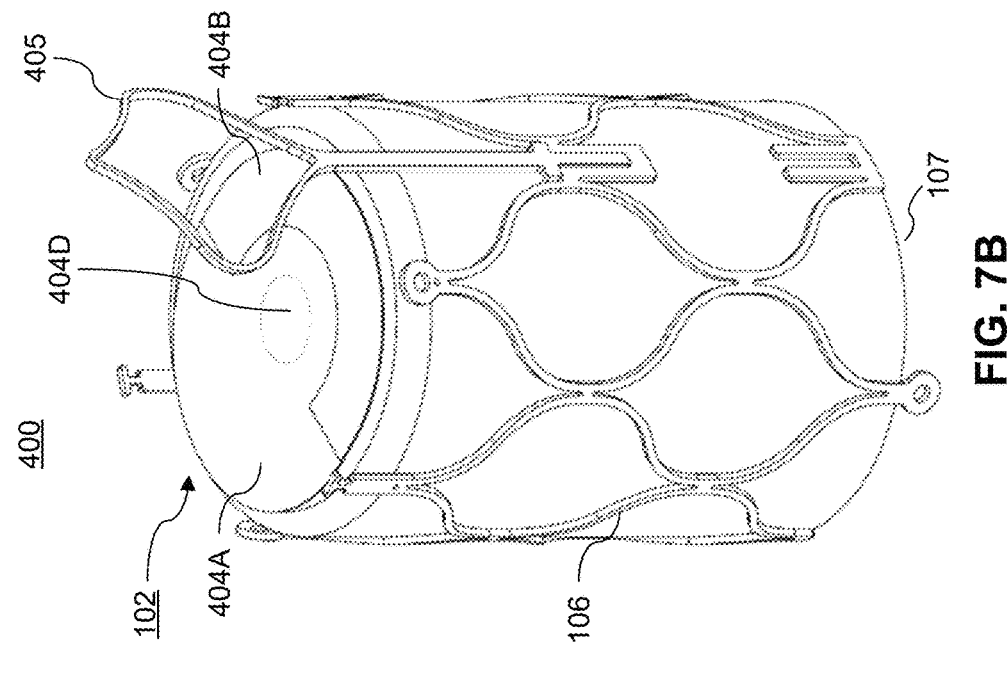
FIG. 7B
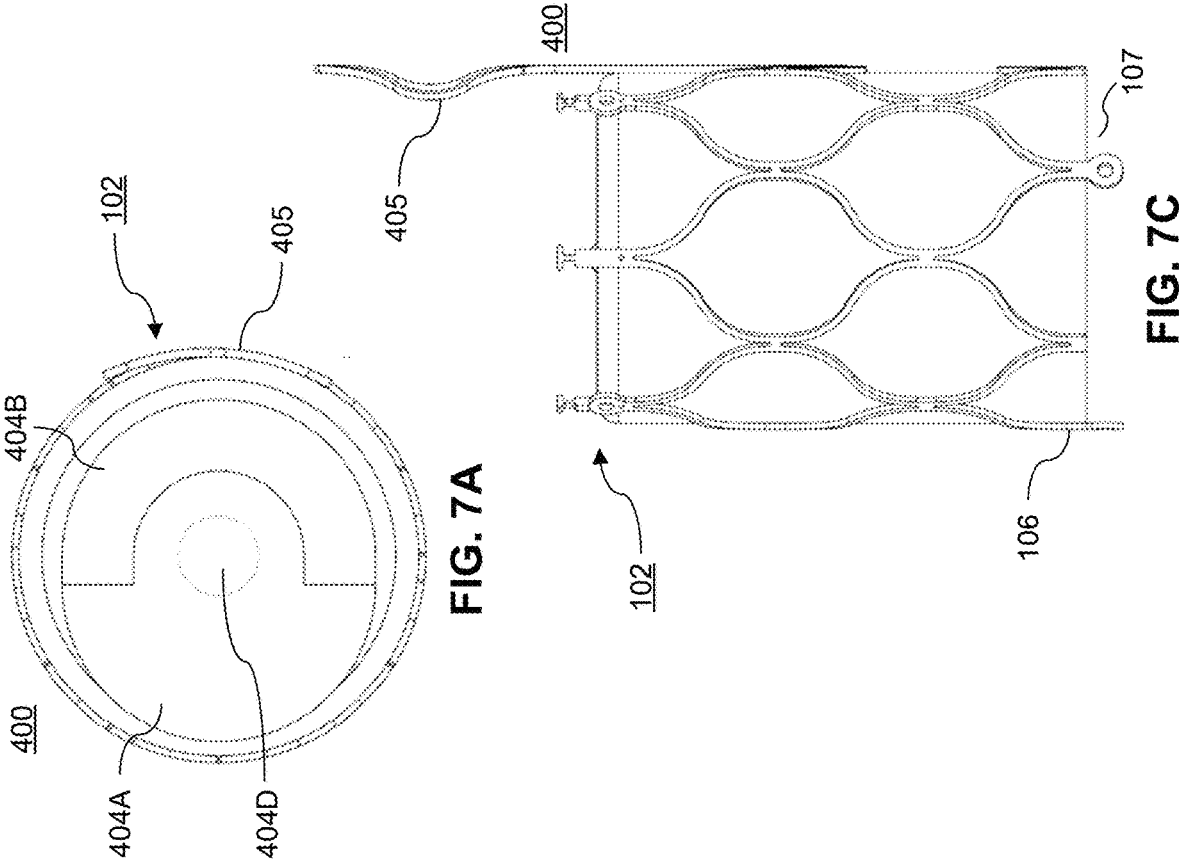
FIG. 7A
FIG. 7C

Implant a variable occluder in a coronary sinus region proximate a left atrium    2002

Following venous system compensation, shunt oxygenated blood flow into the coronary sinus to cause retrograde flow of oxygenated blood in at least a portion of the venous system of the myocardium to thereby enable revascularization of the myocardium    2004

DEVICES, SYSTEMS, AND METHODS FOR MANAGING BLOOD FLOW

CROSS-REFERENCE TO RELATED APPLICATIONS

This application is a continuation of U.S. application Ser. No. 19/098,279, filed on Apr. 2, 2025, which is based on and claims benefit of priority of Israeli Patent Application No. 311902, filed on Apr. 2, 2024, and Israeli Patent Application No. 315496, filed on Sep. 7, 2024, the contents of all of which are incorporated herein by reference in their entireties.

TECHNICAL FIELD

The present disclosure generally relates to the field of medical devices, and particularly relates to devices, systems, and methods for manipulating blood flow in the cardiovascular system, including via controlled occlusion.

BACKGROUND

The primary function of the heart (myocardium) is to pump oxygenated blood throughout the body. The heart includes four chambers: left and right atria and left and right ventricles, as well as a series of valves, and a network of veins and arteries. In a healthy myocardium, deoxygenated blood from the body enters the right atrium through the superior and inferior vena cava. This blood is forced through the tricuspid valve and into the right ventricle, where it is then pumped to the lungs for oxygenation via the pulmonary valve and pulmonary arteries. Oxygenated blood then returns from the lungs towards the left atrium via the pulmonary veins where the oxygenated blood is then pumped into the left ventricle through the mitral valve. The left ventricle pumps this oxygenated blood through the aortic valve and into the aorta where it is then distributed throughout the body via a complex network of arterial vessels.

While the superior and inferior vena cava are primarily responsible for directing deoxygenated blood from the body and into the right atrium, the coronary sinus is primarily responsible for directing venous (i.e., deoxygenated) blood from the vasculature of heart tissue into the right atrium. This large cardiac vein arises at the junction of the great cardiac vein and oblique vein of the left ventricle and is partially situated within the posterior atrioventricular groove between the left atrium and left ventricle. Tributary veins, including the anterior interventricular vein (AIVV), great cardiac vein (GVC), and posterior interventricular vein (PIVV), each drain into the coronary sinus. The oxygen saturation (PO2) within the coronary sinus generally falls in the range of 15-35+/−5 mmHg.

When vasculature within the heart is insufficiently oxygenated, e.g., as a result of coronary artery disease, atherosclerosis, and arteriosclerosis, complications including angina, heart attack, and heart failure may arise. Various surgical techniques may be used to mitigate these complications. Angioplasty, for example, (also known as Percutaneous Coronary Interventions, Balloon Angioplasty and Coronary Artery Balloon Dilation), involves the surgical widening of a clogged or otherwise narrowed artery. Here, the surgeon delivers a catheter balloon system to the site of obstruction and inflates the balloon to widen the obstruction and improve blood flow through the artery. A stent may be inserted to prevent the artery from contracting, thereby maintaining blood flow therethrough. The surgeon may also use a laser (laser angioplasty) or cutting tool (atherectomy) to vaporize or cut away any blockage.

Another method for correcting oxygen deficiency is coronary bypass surgery (also known as coronary artery bypass grafting or "CABG"). Here, an open-heart procedure is used to graft a healthy blood vessel onto the heart to reroute blood around the obstructed artery. The graft may be harvested from the patient or a donor and usually originates from one or more of the leg, arm, or chest, depending on the number of grafts needed. Complications and recovery time tend to be more extensive due to the invasiveness of the open-heart procedure, which usually requires the surgeon to stop the heart to complete the procedure and increases the risk of infection at both the chest incision and graft incision sites.

Yet another method for correcting oxygen deficiency involves perfusion of oxygenated blood throughout the heart using one or more surgically created holes in the left ventricle. In transmyocardial revascularization (TMR), one or more lasers are used to create multiple channels through the left ventricle to improve direct perfusion to the myocardium. The method may be beneficial when a patient is not responsive to or ineligible for coronary bypass surgery or percutaneous coronary intervention. Like TMR, percutaneous myocardial revascularization (PMR) also uses surgically created holes to enable direct myocardial perfusion; the procedure, however, tends to be less invasive.

Still, other methods contemplate the use of various stent devices or grafts to direct oxygenated blood from the left ventricle to a coronary artery or to provide a retrograde flow of oxygenated blood from the left ventricle to the myocardium via the coronary sinus. PCT Application No. PCT/IB2023/051918 (the disclosure of which is hereby incorporated herein by reference) discloses a method and device for creating a passage between a cavity in a heart chamber and a lumen in a vessel while extending the passage in a retrograde flow direction within the lumen by flow deflection. The device disclosed therefore, is designed to occlude blood flow through a coronary sinus, as well as shunt blood from a heart chamber towards the vessel. When a positive pressure gradient persists between the blood in the heart chamber and the blood in the coronary sinus, for example, a retrograde flow of oxygenated blood towards the myocardium may ensue post-procedure. However, in some cases, a positive pressure gradient does not development immediately. Typical occluders do not allow for highly sensitive pressure gradient occlusion at the target pressures, increased occlusion over time while also enabling tool crossing at a delayed time point.

Another source of heart failure may occur as the result of elevated left atrial pressure (LAP), which in turn causes back pressure in the lungs and can lead to dangerous fluid buildup in the lungs. One method of alleviating this dangerous condition is to reduce left atrial pressure.

The devices, systems and methods described herein address at least some of the drawbacks of traditional occluders and revascularization techniques. Such devices, systems, and methods may allow for venous system compensation within a vessel. The venous system compensation may occur in varying inventive ways within the scope of this disclosure. For example, a variable occluder may benefit patients in a first stage of redirecting blood flow to minimize dramatic pressure changes within a vessel. A medical practitioner might be able to confirm the existence of venous system compensation prior to causing retrograde flow of oxygenated blood.

SUMMARY

Embodiments consistent with the present disclosure provide devices, systems, and methods for promoting venous system compensation to enable retrograde oxygenated blood flow in myocardia, including by using a variable occluder.

Some embodiments include a method for causing retrograde oxygenated blood flow in at least a portion of the venous system of the myocardium. Embodiments may include implanting a variable occluder in a coronary sinus region proximate a left atrium. The variable occluder may be configured to gradually increase a level of blood flow restriction over a period of days to enable a venous system of the myocardium to compensate for increased pressure caused by the gradual increase in the level of blood flow restriction. Embodiments may also include following venous system compensation, shunting oxygenated blood flow into the coronary sinus to cause retrograde flow of oxygenated blood in at least a portion of the venous system of the myocardium to thereby enable revascularization of the myocardium.

Some embodiments include a device for promoting venous system compensation to enable retrograde blood flow in at least a portion of the venous system of the myocardium. Embodiments may include a support configured for implantation within a coronary sinus at a location proximate a left atrium. The support may be adapted to transition between a compressed state for delivery within the coronary sinus and an expanded state for fixation within the coronary sinus. The support in the expanded state may include a passageway therethrough. Embodiments may include a variable occluder associated with the support. The variable occluder may be configured to gradually increase a level of antegrade blood flow restriction through the passageway over a period of days to enable the at least a portion of the venous system of the myocardium to compensate for increased pressure caused by the gradual increase in the level of antegrade blood flow restriction. The variable occluder may be further configured to substantially occlude antegrade blood flow through the passageway when a pressure on an upstream side of the variable occluder reaches a threshold of between 30 and 60 mmHg. The variable occluder may further be configured to cause retrograde flow in the at least a portion of the venous system of the myocardium on an upstream side of the variable occluder The foregoing summary is intended to provide an introductory flavor of a few aspects of innovations described more fully herein.

BRIEF DESCRIPTION OF THE DRAWINGS

The accompanying drawings, which are incorporated in and constitute a part of this disclosure, illustrate disclosed embodiments and, together with the description, serve to explain the disclosed embodiments. The particulars shown are by way of example and for purposes of illustrative discussion of embodiments of the present disclosure. The description taken with the drawings makes apparent to those skilled in the art how embodiments of the present disclosure may be practiced.

FIG. 4A is a plan view of an example variable occluder in an open state, consistent with consistent with some disclosed embodiments.

FIG. 4B is an isometric view of the example occluder illustrated in FIG. 4A.

FIG. 4C is a side view of the example occluder illustrated in FIG. 4A.

FIG. 5A is a plan view of the example variable occluder illustrated in FIG. 4A in a closed state, consistent with some disclosed embodiments.

FIG. 5B is an isometric view of the example occluder illustrated in FIG. 5A.

FIG. 5C is a side view of the example occluder illustrated in FIG. 5A.

FIG. 7A is a plan view of the example occluder illustrated in FIG. 4A in a deactivated state, consistent with some disclosed embodiments.

FIG. 7B is an isometric view of the example occluder illustrated in FIG. 7A.

FIG. 7C is a side view of the example occluder illustrated in FIG. 7A.

DETAILED DESCRIPTION

Figure 1A:
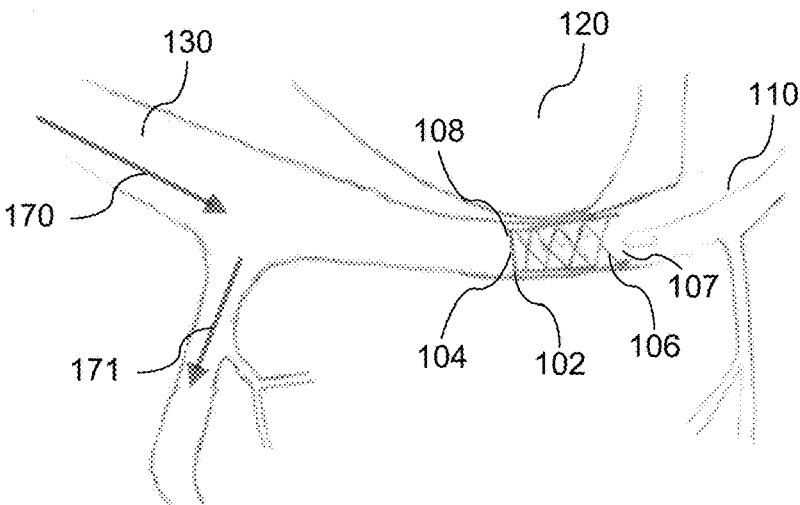
FIGS. 1A, 1B, and 1C graphically depict steps of an example process for causing retrograde flow in at least a portion of a biological structure, consistent with some disclosed embodiments.

Exemplary embodiments are described with reference to the accompanying drawings. The figures are not necessarily drawn to scale. Elements represented by the same or like reference numerals are intended to represent the same or like parts unless otherwise disclosed or represented. While examples and features of disclosed principles are described herein, modifications, adaptations, and other implementations are possible without departing from the spirit and scope of the disclosed embodiments. Also, the words "comprising," "having," "containing," "including," and other similar forms are intended to be equivalent in meaning and be open ended in that an item or items following any one of these words is not meant to be an exhaustive listing of such item or items or meant to be limited to only the listed item or items. It should also be noted that, as used herein and in the appended claims, the singular forms "a," "an," and "the" include plural references unless the context clearly dictates otherwise. Moreover, the relational terms herein such as "first" and "second" are used only to differentiate an entity or operation from another entity or operation, and do not require or imply any actual relationship or sequence between these entities or operations.

As used herein, unless specifically stated otherwise, the term "or" encompasses all possible combinations, except where infeasible. For example, if it is stated that a component can include A or B, then, unless specifically stated otherwise or infeasible, the component can include A or B, or A and B. As a second example, if it is stated that a component can include at least one of A, B, or C, then, unless specifically stated otherwise or infeasible, the component can include A, B, or C, or A and B, or A and C, or B and C, or A, B, and C.

This disclosure employs open-ended permissive language, indicating for example, that some embodiments "may" employ, involve, or include specific features. The use of the term "may" and other open-ended terminology is intended to indicate that although not every embodiment may employ the specific disclosed feature, at least one embodiment employs the specific disclosed feature.

In the following description, various working examples are provided for illustrative purposes. However, is to be understood the present disclosure may be practiced without one or more of these details. Reference will now be made in detail to non-limiting examples of this disclosure, examples of which are illustrated in the accompanying drawings. The examples are described below by referring to the drawings, wherein like reference numerals refer to like elements. When similar reference numerals are shown, corresponding description(s) are not repeated, and the interested reader is referred to the previously discussed figure(s) for a description of the like element(s).

Some embodiments of the present disclosure relate generally to medical devices, methods, and systems for managing blood flow. For example, some disclosed embodiments may relate to a method for causing retrograde oxygenated blood flow in at least a portion of the venous system of the myocardium. As used herein, the venous system of the myocardium refers to at least a portion of the collection or network of veins that drains deoxygenated blood from the myocardium and returns the deoxygenated blood to the right atrium. Some examples of a portion of the venous system of the myocardium may include the coronary sinus, the great cardiac vein, the middle cardiac vein, the small cardiac vein, the posterior vein of the left ventricle, the oblique vein of the left atrium, and/or any other blood vessel that drains deoxygenated blood from the myocardium, including capillaries.

Figure 1B:
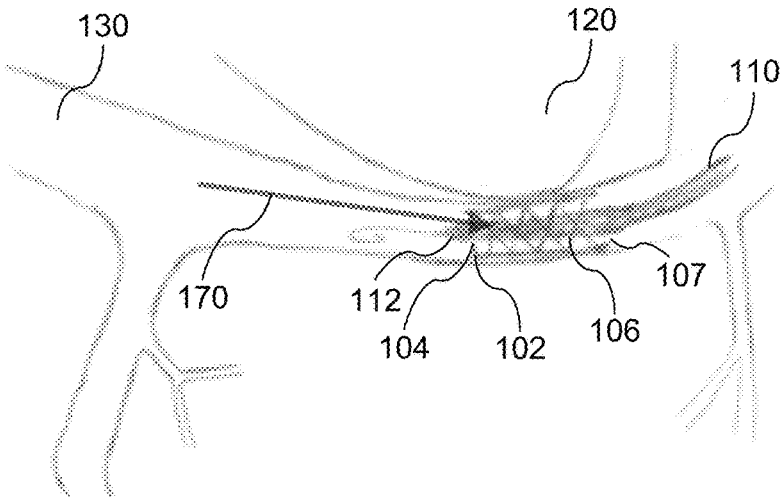
Figure 1C:
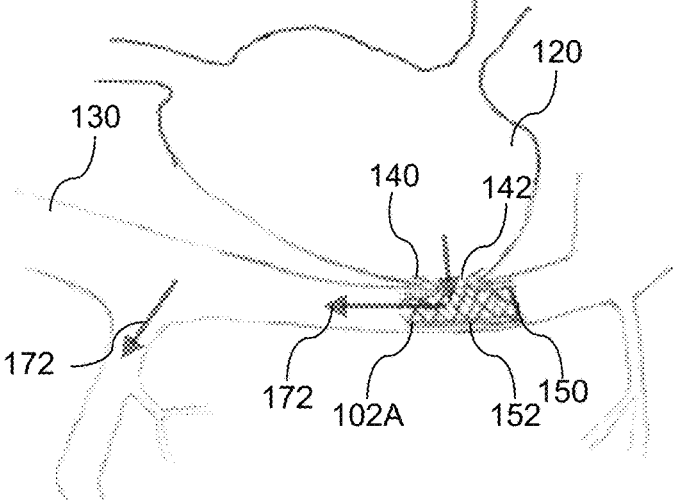

By way of non-limiting example, a portion of the venous system of the myocardium may include coronary sinus 130 as depicted in FIG. 1A-1C.

As used herein, retrograde flow refers to a flow in a direction opposite a normal or expected direction. For example, retrograde flow in at least part of the venous system of the myocardium refers to a flow of blood in a direction opposing a vein-natural direction (e.g., towards the myocardium). By way of non-limiting example, retrograde flow in the coronary sinus may include a flow of blood through the coronary sinus away from the right atrium (e.g., through the great cardiac vein). Retrograde flow in at least a portion of the venous system of the myocardium may refer to reverse flow in the coronary veins and capillaries that branch off (e.g., directly, indirectly) the coronary sinus. The venous system naturally carries deoxygenated blood in an antegrade direction toward the right atrium of the heart. To achieve retrograde flow of oxygenated blood in the venous system, a source of oxygenated blood may be supplied to the venous system of the myocardium, as discussed later in greater detail. As used herein, antegrade flow refers to a flow in a normal or expected direction. For example, antegrade flow in at least part of the venous system of the myocardium may include a flow of blood in a vein-natural direction (e.g., towards the right atrium). Antegrade flow in the coronary sinus involves a flow of blood through the coronary sinus and towards the right atrium.

As used herein, causing retrograde flow refers to inducing a flow of fluid in a structure in a direction different from a normal or typical direction. For example, one or more devices or components may be inserted or implanted into a biological structure (e.g., blood vessel) to at least partially occlude or restrict normal antegrade flow. Additionally or alternatively, one or more devices or components may be inserted or implanted into a first biological structure carrying oxygenated blood (e.g., left atrium, left ventricle) to provide a passageway to facilitate a supply and flow of the oxygenated blood in a retrograde direction in a second biological structure (e.g., at least a portion of the venous system of the myocardium).

Non-limiting examples of causing retrograde flow are described and exemplified elsewhere herein, including as depicted in FIGS. 1C and 15.

In some embodiments, a method may include implanting a variable occluder in a coronary sinus region proximate a left atrium. The left atrium is one of the four chambers of the heart. It is located in the upper left part of the heart and, in normal operation, receives oxygenated blood from the lungs. In this way, the left atrium may be used as a source of oxygenated blood. The coronary sinus is a large venous structure in the heart that, in normal operation, collects deoxygenated blood from the heart muscle (myocardium) and drains it into the right atrium. It runs along the posterior (back) side of the heart, within the coronary sulcus, and in normal antegrade operation receives blood from several cardiac veins, including the great cardiac vein, middle cardiac vein, small cardiac vein, and others. A portion of the coronary sinus passes adjacent the left atrium. Any region of the coronary sinus that passes adjacent the left atrium is proximate the left atrium.

By way of non-limiting example, FIG. 1A-1C depict a region of coronary sinus 130 proximate left atrium 120.

As used herein, an occluder refers to a device, component, or combination of devices and/or components configured to restrict fluid flowing through a structure, such as blood flowing through a biological structure, e.g., a blood vessel. For example, an occluder may be configured to at least partially block or restrict a flow of fluid flow. Thus, an occluder may include any component, device, or structure that blocks, obstructs, slows, or inhibits fluid flow, including partially and/or fully. Further, an occluder may be configured to at least partially block or restrict a natural flow of fluid (e.g., antegrade flow) in a blood vessel. Other non-limiting examples of an occluder are disclosed in Israeli Patent Application No. 310788 and PCT Application No. PCT/IB2025/051423 (the entire disclosures of which are incorporated herein by reference).

A partial occlusion may occur when an object or obstruction partially blocks a passage such that fluid flows at a reduced rate compared to a normal flow rate without the object or obstruction. For example, an occluder that partially occludes a biological structure may permit a reduced amount of fluid to flow through a biological structure relative to the amount of fluid that would ordinarily flow through the biological structure without the occluder present. A full occlusion may occur when an object or obstruction completely blocks a passage such that substantially no fluid flows passes through. For example, an occluder that fully occludes a biological structure may permit substantially no fluid (e.g., 0%, 1%, less than 1% of normal flow) to flow past or through the occluder.

As used herein, variable refers to a capability to change or take on different values or forms. Thus, a variable occluder refers to a device or component configured to adjust or vary a level or extent of occlusion (i.e., flow restriction). Depending on design, an extent of occlusion of a variable occluder may change in response to changes in pressure, changes in a pressure gradient, manual adjustment, time delay, or as the result of natural occurrence over time.

For example, a variable occluder may include an adjustable portion configured such that adjustments affecting the adjustable portion change (e.g., reduces, increases) a level of blood flow restriction therethrough. By way of non-limiting example, adjusting may include opening, closing, restricting, dilating, deflating, inflating, collapsing, or expanding an adjustable portion.

By way of non-limiting examples, FIGS. 1A and 1B generally depict occluding surface 104 of an exemplary variable occluder 102. Other non-limiting examples of an occluding surface of a variable occluder include flap 404A and fixed portion 404B as depicted in FIGS. 4A, 5A, 6A, and 7A, the operation of which is described later in greater detail.

Additionally or alternatively, a variable occluder may include a pierceable, removable, or biodegradable portion such that after piercing (e.g., by a tool), removal (e.g., surgically), or biodegradation of the portion, the level of occlusion decreases and the flow of fluid increases. A biodegradable portion may include any material configured to break down naturally via microorganisms, enzymes, or environmental factors over time. For example, biodegradable materials may include polyols or magnesium alloy. By way of non-limiting example, a pierceable portion may include a material that can be pierced or punctured by a catheter, such as nitinol or polyurethane.

Figures 6A, 6B, 6C, 6D:
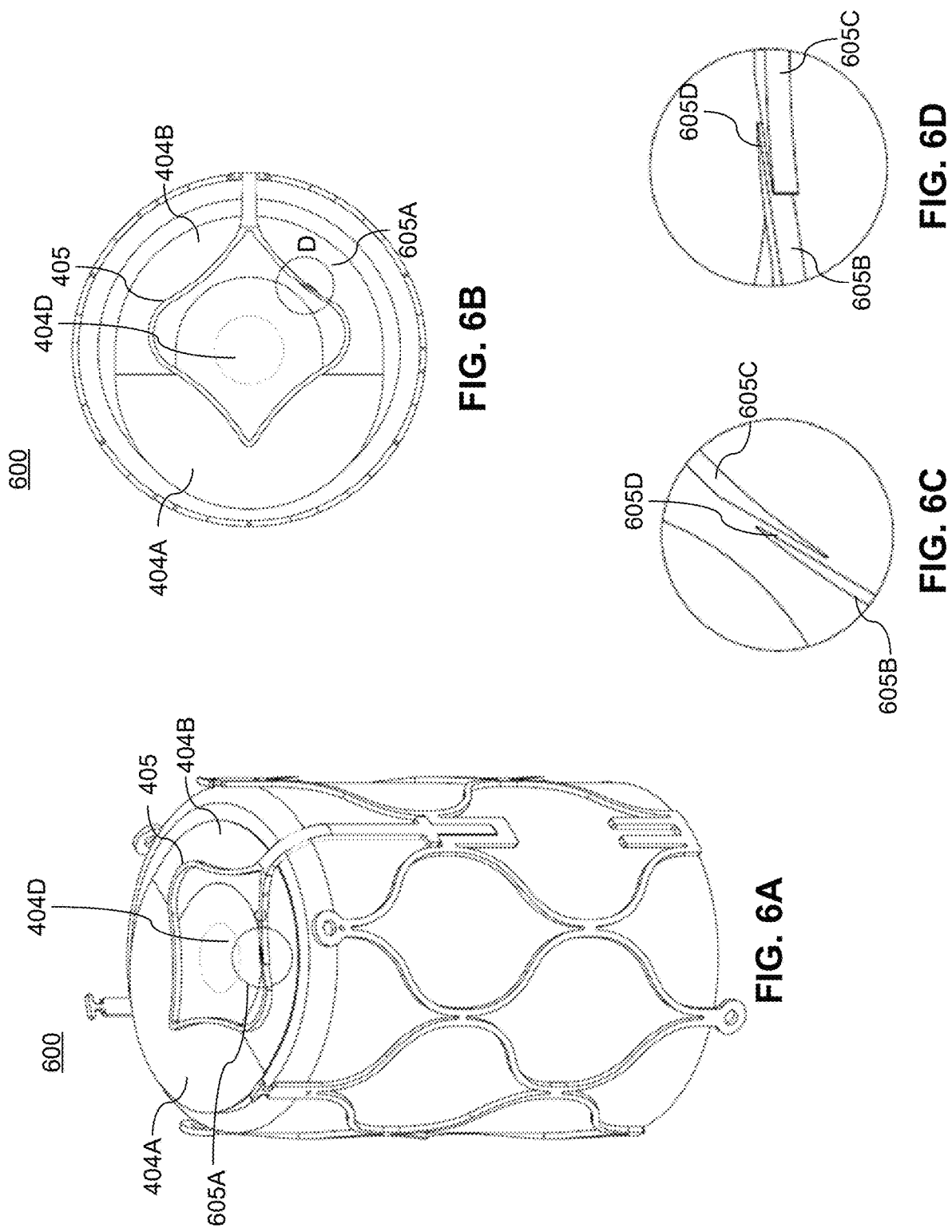
FIG. 6A is an isometric view of an example occluder with a discontinuous frame, consistent with some disclosed embodiments.
FIG. 6B is a plan view of the example occluder illustrated in FIG. 6A.
FIG. 6C is an expanded view of a portion of the discontinuous frame illustrated in FIG. 6A.
FIG. 6D is an expanded view of a portion of the discontinuous frame illustrated in FIG. 6B.

By way of another non-limiting example, occluding surface 104 of variable occluder 102 depicted in FIG. 1A may be pierceable, such as by tool 110 as depicted in FIG. 1B. Other non-limiting examples of a pierceable occluding surface of a variable occluder is depicted in FIG. 6A, the operation of which is described later in greater detail.

Alternatively or additionally, a variable occluder may be configured to form flow restriction over time. For example, a variable occluder may provide a structure treated to encourage a growth of tissue or clotting over time. Non-limiting examples of such a treatment may include plasma treatment to enhance protein adsorption and cell attachment, roughening, hydroxyapatite coating, chemical etching, peptide or protein coating (e.g., Arginyl-Glycyl-Aspartic acid), or any other means of treatment to encourage tissue growth known to those skilled in the art. In this way, a level of blood flow restriction increases over time as the occluding surface is formed.

Additionally or alternatively, a variable occluder may include a portion that is substantially impermeable or adapted to decrease permeability to blood over time. The term impermeable refers to the complete or significant blockage of a substance from passing through. For example, a substantially impermeable surface may include a surface that permits substantially no fluid (e.g., 0%, 1%, less than 1%) to flow therethrough. In one non-limiting example, a variable occluder may include a surface comprising a material that is adapted to decrease permeability over time.

By way of non-limiting example, occluding surface 104 depicted in FIG. 1A may be made of materials adapted to decrease in permeability over time. For example, the material may be porous (e.g., porous titanium) around and into which fibrous tissue or collagen may form. Non-limiting examples of variable occluders are further described and exemplified elsewhere herein, including as depicted in FIGS. 4A, 8A, 9A, 10A, 11A, 12A, 13A, and 14A-14F.

In some embodiments, a variable occluder may include a stent. As used herein, a stent refers to a scaffold (e.g., cone) or tube configured to be placed or located in a structure to keep the structure open, or to affix another element within the structure. A stent may be configured to engage with the walls of a structure to secure a positioning of the stent in the structure. For example, a stent may include a mesh or scaffold that, when implanted in a structure (e.g., coronary sinus), contacts the walls of the structure to maintain a stable orientation and a support for an occluder surface, as described in greater detail herein. In other contexts, a stent may also serve as a scaffold to maintain an opening. Stents may be made of stainless steel, cobalt-chromium alloys, platinum-chrome alloys, poly-l-lactic acid (PLLA), poly (lactic-co-glycolic acid) (PLGA), nitinol or any other biocompatible material.

In one non-limiting example, FIG. 4A-4C depict variable occluder 102 including stent 106. Further, FIG. 1A-1C depict stent 106 and stent 152 engaging with the walls of coronary sinus 130, thereby securing the occluder's positioning within coronary sinus 130.

In some disclosed embodiments, an occluding surface may radially traverse the stent. As used herein, an occluding surface includes a layer, face, membrane, structure, or combination thereof configured to block, seal, or obstruct a passage or opening to at least partially prevent a flow of fluid therethrough. For example, an occluding surface may include one or more layers, faces, or membranes that together are configured to at least partially prevent a flow of fluid. Further, an occluding surface may have a substantially flat shape, a substantially scoop shape, or any other shape or configuration that accomplishes the occluding function.

By way of non-limiting example, FIG. 4A-4C depict occluding surface 104 with flap 404A, fixed portion 404B, and flexible frame 405, the operation of which is further described in greater detail elsewhere herein.

An occluding surface may radially traverse a stent. Radially traversing refers to covering a face or a portion of a diameter or face of a stent. For example, an occluding surface may be said to radially traverse a stent if the orientation of the occluding surface extends along all or a portion of a radius of the stent (i.e., a radius that defines a passageway through the stent). In some disclosed embodiments, the radial traversal of the occluding surface extents over the outermost edge of the stent passageway. However it is contemplated that the occluding surface may radially traverse the stent from a location inset from an edge of the stent (e.g., within the passageway). In one example, when a first component is located within a second component or partially or fully extends over a second component at least partially covering or sealing the second component, the first component may be considered to radially traverse the second component.

Figures 10A, 10B:
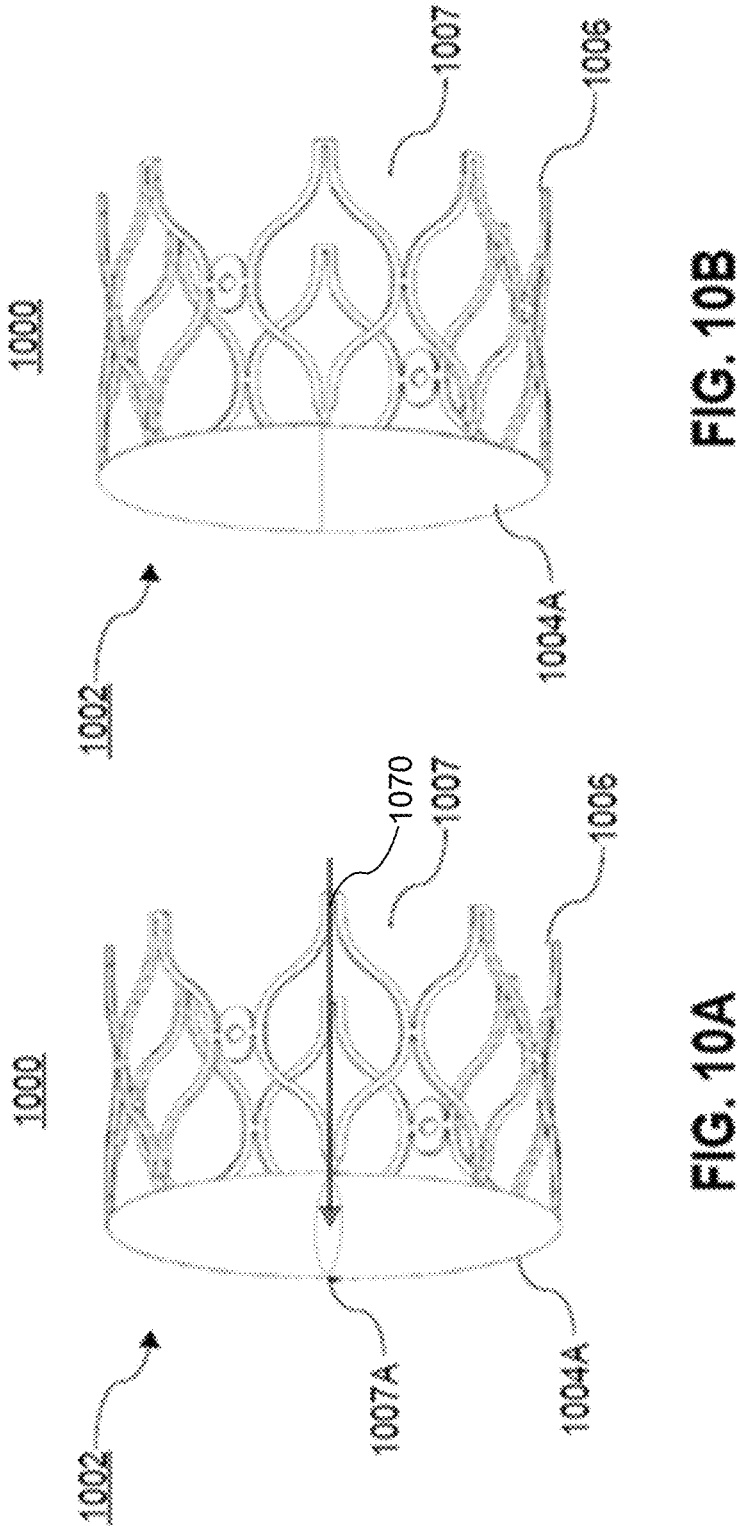
FIG. 10A is an isometric view of another example occluder in an open state, consistent with some disclosed embodiments.
FIG. 10B is an isometric view of the example occluder illustrated in FIG. 10A in a closed state, consistent with some disclosed embodiments.

By way of non-limiting example, FIG. 4A-4C depict occluding surface 104 radially traversing stent 106. Other non-limiting examples of an occluding surface radially traversing a stent are depicted in FIG. 10A (e.g., device 1000 with an occluding surface including flaps 1004A radially traversing support 1006), 11A (e.g., device 1100 with an occluding surface including perforated sheet 1104D radially traversing support 1106), and 14A-14F (e.g., occluding surface 1404 radially traversing first section 1411 of support 1406), as described later in greater detail.

In some embodiments, a stent may include a coupling element configured to couple or decouple an occluding surface radially traversing the stent. For example, a coupling element may include a tether or engagement feature, as described and exemplified elsewhere herein, configured for decoupling. By way of non-limiting example, decoupling may include cutting, removing, disconnecting, disengaging, or severing the coupling element such that the occluding surface is no longer connected or coupled to the stent. In a coupled state, for example, the occluder may be fixedly closed. Upon decoupling the occluder may be permitted to open, for example, in response to pressure.

In some embodiments, the occluding surface may include at least one sheet of material. As used herein, a sheet of material refers to a layer, face, or membrane. For example, an occluding surface may include one or more sheets of material that together are configured to at least partially prevent a flow of fluid. The material may include any biocompatible material as described and exemplified elsewhere herein.

Figures 11A, 11B:
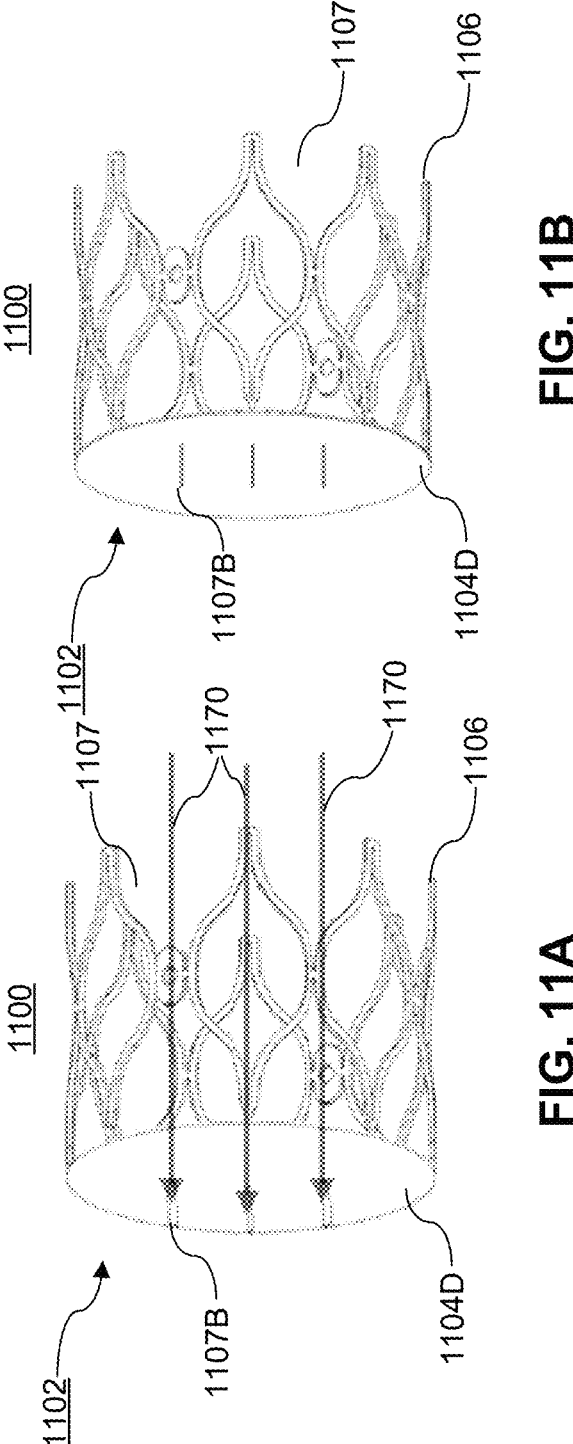
FIG. 11A is an isometric view of another example occluder in an open state, consistent with some disclosed embodiments.
FIG. 11B is an isometric view of the example occluder illustrated in FIG. 11A in a closed state, consistent with some disclosed embodiments.

By way of non-limiting example, FIG. 11A-11B depict an occluding surface including one sheet of material such as perforated sheet 1104D. In other non-limiting examples, an occluding surface may include a plurality of sheets of material (e.g., at least two). In such examples, additional sheets of material may provide increased strength or resistance to an occluding surface, thereby decreasing a risk of failure (e.g., due to too great a pressure against the occluding surface).

As used herein, implanting refers to a process of placing or locating a device, component, or combination of device and/or component inside a body. Implanting may include surgically placing a device or a component at a treatment site inside a biological structure. By way of one non-limiting example, implanting the variable occluder may include delivering it to the heart using a minimally invasive procedure called percutaneous coronary intervention (PCI). In this procedure, a small incision may be made in the right internal jugular vein or left subclavian vein. A catheter is advanced into the superior vena cava to the right atrium. The same or another catheter may be used to locate the opening of the coronary sinus near the tricuspid valve (posteroinferior aspect of the right atrium). A guidewire may then be advanced into the coronary sinus, following its curvature. A balloon may be advanced along the guidewire to a location for implantation (e.g., a coronary sinus region proximate the left atrium). The balloon may be expanded to widen the coronary sinus. A stent and the variable occluder, both of which in a compressed state, may be advanced along the guidewire to the location for implantation, at which location the stent and the variable occluder may be expanded, thereby completing the implantation of the variable occluder.

The coronary sinus is one example of a location in which an occluder may be implanted. Other examples of structures in which or through which an occluder may be implanted or conveyed include any other blood vessel, a capillary, an artery, a vein, a heart chamber (e.g., left atrium, left ventricle, right atrium, right ventricle), or any other anatomical organ. In some embodiments, a medical device or component may be configured to be implanted at a treatment site in a biological structure to cause a temporary or permanent change or transformation. A treatment site may refer to a particular location on or within the body of a patient at which a medical intervention, procedure, device, or therapy is applied. For example, a treatment site may include an area within a biological structure at which location a medical device or component may be implanted. By way of non-limiting example, a treatment site may include a location for implantation of an occluder in a first biological structure (e.g., coronary sinus, great cardiac vein, oblique vein of the left atrium) proximate a second biological structure (e.g., left atrium, left ventricle) to at least partially occlude a flow of fluid (e.g., blood) through the first biological structure.

In some embodiments, implanting may include permanent implants or temporary implants. A permanent implant may include a medical device or component configured to remain in the body indefinitely or for an extended period of time (e.g., years, decades). For example, a permanent implant may be configured to provide long-term support, function, or therapy without the need for removal. A temporary implant may include a medical device or component configured to remain in the body for a limited period of time (e.g., days, weeks, months). For example, a temporary implant may be configured to be removed (e.g., surgically) or otherwise disabled (e.g., dissolved, deactivated) such that the implant does not perform an intended or expected functionality.

In some embodiments, a variable occluder may be configured for transvascular delivery in a compressed state for implantation in the coronary sinus via expansion in the region of the left atrium. As used herein, transvascular delivery refers to a process of implanting, locating, or placing a device or component through blood vessels. For example, transvascular delivery may include PCI, as described earlier.

Figure 2:
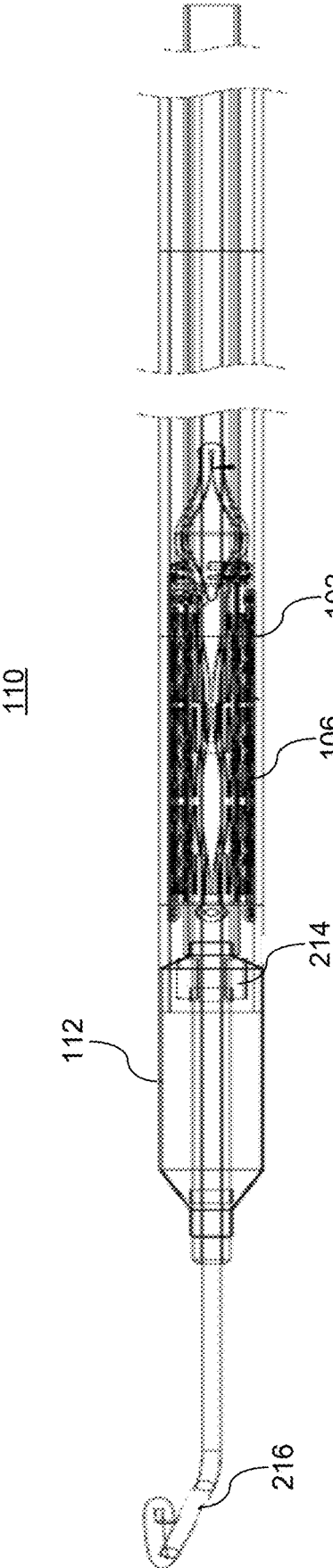
FIG. 2 is a side view of an example implantation tool, consistent with some disclosed embodiments.

By way of non-limiting example, FIG. 2 depicts a tool 110 configured to transvascularly deliver a variable occluder in a compressed state for implantation in a biological structure (e.g., coronary sinus). Tool 110 may be inserted into a vascular system of a body and guided to a treatment site inside the biological structure. By way of non-limiting example, tool 110 may include a puncture component having a sharp edge, such as disclosed in PCT Application No. PCT/IB2023/061707, incorporated herein in its entirety by reference.

Additionally or alternatively, in some embodiments, a tool configured to transvascularly deliver a component or device to a location within a body may include a cannula or pushing component. A cannula refers to a flexible or hollow tube or needle. For example, an inner surface of a cannula may include a rail configured to mate or engage with a variable occluder. In such an example, the variable occluder may be cannulated (e.g., having a hollow center for receiving or engaging with a cannula). A pushing component refers to a structure configured to push, advance, or deploy at least a portion of the tool or an implantable device. Further, the pushing component may be configured to be releasably connected or engaged with the tool or implantable device. For example, the pushing tool may include grooves or projections that may engage with a variable occluder.

By way of non-limiting example, the pushing component may include a catheter that may be guided along or over a guidewire to push or direct (e.g., by a pushing motion) a variable occluder to a location within a biological structure (e.g., portion of the venous system of the myocardium) for implantation. Further, the catheter may be a retractable delivery catheter adjustable between a delivery configuration, in which the delivery catheter covers or constrains a device or component to be implanted, and a deployed configuration, in which the delivery catheter is retracted to expose the device or component to be implanted.

As used herein, a compressed state refers to a state in which a device or component is compacted or reduced in size or volume. For example, a variable occluder in a compressed state may occupy a reduced volume compared to a variable occluder in an expanded state. Further, a variable occluder in a compressed state may be folded or squeezed such that it is contained within a delivery catheter.

Figure 3A:
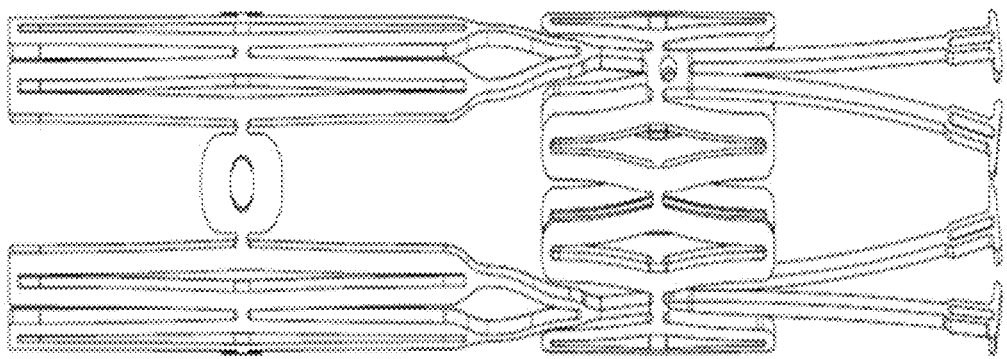
FIG. 3A is a side view of an example support in a compressed state, consistent with some disclosed embodiments.
Figure 3B:
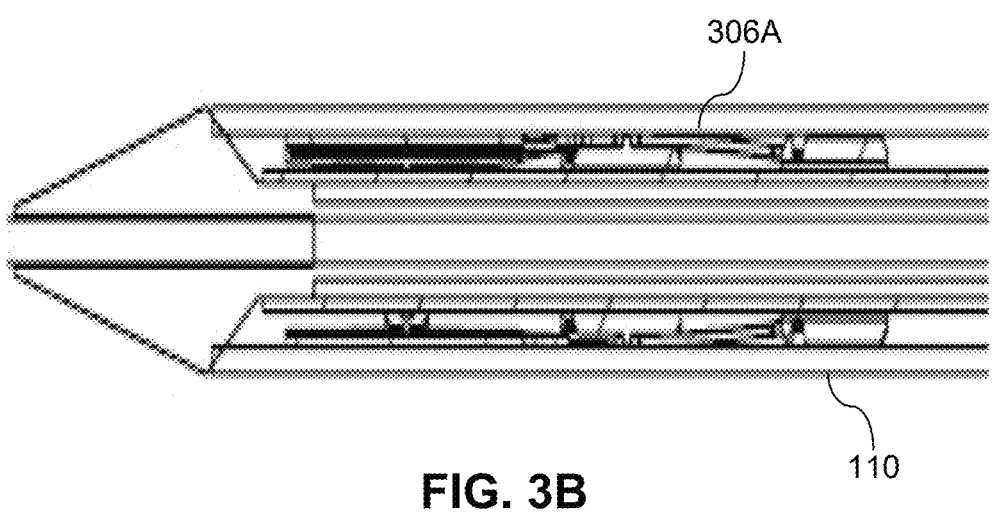
FIG. 3B is a side view of the example support depicted in FIG. 3A inside an example tool, consistent with some disclosed embodiments.

By way of non-limiting example, FIG. 2 depicts an occluder 102 in a compressed state contained within tool 110. Further, FIG. 3A depicts support 306A in a compressed state, and FIG. 3B depicts support 306A in a compressed state inside tool 110. In general, it may be understood that any device or component configured for implantation and disclosed herein may have a compressed state and an expanded state.

As used herein, expansion refers to the act of becoming larger, opening or spreading out. Expansion may occur, for example, through inflation, returning to a larger shape (in the case of a shape memory alloy), or through deformation, or any other transformation that causes a device or component to increase in size, volume or footprint. For example, expansion may occur by releasing a compressed device from an enclosure such that the compressed device unfolds or increases in size to an original size. Further, expansion may occur by inflating a device using a gas or fluid, including inflating the device located within another device, thereby inflating the other device as well.

By way of non-limiting example, FIG. 2 depicts tool 110 storing occluder 102 and stent 106 in a compressed state and an expandable element 112. After tool 110 is positioned at a desired location within a biological structure (e.g., coronary sinus region proximate the left atrium), occluder 102 and stent 106 may be released from tool 110 and expanded (e.g., due to stored elastic energy, by expandable element 112).

In some embodiments, a variable occluder may be configured to gradually increase a level of blood flow restriction over a period of days. Blood flow restriction refers to regulation and/or limitation of blood flow. Blood flow restriction may be partial or complete and may be caused by a barrier, obstruction, or obstacle. For example, a variable occluder implanted in a biological structure (e.g., coronary sinus) may be configured to transition from an open state, in which a first level of blood flow restriction permits a reduced blood flow (e.g., compared to a blood flow in an absence of the variable occluder), to a closed state, in which a second level of blood flow restriction permits a substantially zero blood flow (e.g., no flow, negligible flow).

The restriction may gradually increase over a period of days, meaning that as days pass, an amount of restriction increases. The gradual increase of restriction may be measured on an average such that during initial days after implantation, a level of restriction may vary and only after the passage of time (e.g., a couple of weeks), an average level of restriction may increase. The gradual increase in restriction may occur slowly or steadily in a progressive or incremental manner. The gradual restriction need not occur in a linear manner over the period. For example, during initial days after implantation, a level of restriction may remain relatively constant and only after the passage of time, a level of restriction may increase. Alternatively, a change in restriction may be relatively constant or predictable over a period of time. The pace at which restriction gradually progresses from a least restrictive state to a most restrictive state may vary on a case-by-case basis. For example, it might depend on the biology of the patient, the ability of the patient to adapt to the gradual restriction, or even the design choice of the medical device designer. A target to be reached for the end of the period for some embodiments may be full occlusion of the vessel, such as the coronary sinus, such that antegrade flow in the vessel is substantially prevented. In other embodiments, the target to be reached for the end of the period may be less than full occlusion such that it permits less than 30%, 20%, 15%, 10%, 5% of normal blood flow.

A variable occluder is configured to gradually increase a level of blood flow restriction if it is specifically designed to achieve the function of a gradually increased blood flow restriction. All of the occluders described herein and illustrated in the accompanying figures are non-limiting examples of variable occluders configured to gradually increase a level of blood flow restriction. Other occluder devices may alternatively be employed, and methods of causing retrograde oxygenated blood flow in at least part of the venous system of the myocardium are not necessarily limited to any particular occluder structure. Rather any structure designed to accomplish the gradual restriction may be used in conjunction with methods described herein.

In some embodiments, a variable occluder gradually increasing a level of blood flow restriction may enable a venous system of the myocardium to compensate for increased pressure caused by the gradual increase in the level of blood flow restriction. Venous system compensation refers to physiological mechanisms by which the venous system adapts to changes in pressure and/or blood volume. After implantation of the occluder, an initial level of occlusion may cause an increase in venous pressure in the coronary sinus on an upstream side of the occluder. This increase in coronary sinus pressure will result in an increase in pressure within the blood vessels that branch off the coronary sinus on the upstream side of the occluder. If occlusion were to occur instantaneously rather than over a period of time, the venous system of the myocardium would experience a significant and instantaneous spike in pressure greater than the venous system might be capable of handling. Such an instantaneous pressure spike might cause irreparable and dangerous damage to the heart. In contrast, by increasing the back pressure in the coronary sinus gradually, the venous system of the heart is provided an opportunity to gradually adapt to the increased pressure. As higher levels of occlusion occur, the venous system can incrementally, gradually, progressively, and/or continuously adapt to ever more increasing levels of occlusion.

The venous system of the myocardium may adapt in one or more different manners. For example, venous system compensation may include venous dilation (i.e., widening of blood vessels) to accommodate an increased pressure. Further, venous system compensation may include angiogenesis. Angiogenesis refers to the process through which new blood vessels form from pre-existing blood vessels. For example, venous system compensation may include the generation and development of new blood vessels to provide a new flow path for blood, which can decrease pressure in the pre-existing blood vessels, enabling a venous system of the myocardium to compensate for increased pressure caused by the gradual increase in the level of blood flow restriction. Over time, the venous system can adapt to higher and higher levels of pressure and/or blood volume. As this occurs, higher and higher levels of occlusion also occur, until a maximum desired level of occlusion is reached (which may or may not be full occlusion). In some patients, this venous system compensation may occur more quickly than in other patients. Thus, a particular occluder with particular occluder characteristics may be selected for a particular patient. In other situations where a patient is expected to respond as does a large group of typical patients, no specially selected occluder may be necessary.

Although the above explanation relates to the specific example of the coronary sinus and the venous system of the myocardium, embodiments of this disclosure are not so restricted. Principles of this disclosure may be applied to other areas of the body and to other blood vessels. Thus, in a broader, sense, a variable occluder may be implanted in another blood vessel, wherein the variable occluder is configured to gradually increase a level of blood flow restriction over a period of days to enable a venous system to compensate for increased pressure caused by the gradual increase in the level of blood flow restriction.

In some embodiments, a variable occluder may be configured to gradually increase the level of blood flow restriction as a function of pressure. A function of pressure refers to a relationship in which at least one variable or characteristic changes or is dependent on pressure. For example, increasing a level of blood flow restriction as a function of pressure may include using a self-expanding or self-closing material (e.g., nitinol, spring, flap, slit in a membrane) configured to close an opening in response to a pressure-dependent mechanism (e.g., actuator triggered by a pressure sensor; deformation of a material; movement of a flap; deformation). The pressure may include a relative pressure differential across or on two different sides of a device or component. For example, a pressure sensor may be configured to detect a pressure gradient across a variable occluder and may be connected to the variable occluder such that, when a pressure gradient threshold is reached, the variable occluder moves or is altered to increase a level of blood flow restriction. The occluder may be biased toward a closed or maximally restricting position, opening against the force of pressure. Thus, in this example, as the pressure drops, the occluder moves toward the closed position.

For example, an occluder may be configured such that when the pressure on an upstream side of the occlusion surface falls below a threshold (e.g., 20 mmHg, 30 mmHg, 40 mmHg, 50 mmHg, 60 mmHg), substantially full occlusion occurs, and above the threshold (e.g., 30 mmHg, 40 mmHg, 50 mmHg, 60 mmHg), the amount of blood permitted to pass the occlusion surface decreases as the pressure on the upstream side of the occlusion surface decreases. In some embodiments, full occlusion may refer to a complete cessation of blood flow through the occluder, and in other embodiments, full occlusion may refer to a sufficient level of occlusion, less than full occlusion, and/or capable of occlusion.

In some embodiments, a variable occluder may be configured to gradually increase the level of blood flow restriction as a function of time. As used herein, a function of time refers to a relationship in which at least one variable or characteristic changes or is dependent on time. For example, increasing a level of blood flow restriction as a function of time may include using a self-expanding or self-closing material (e.g., nitinol, spring) configured to close an opening in response to a time-dependent mechanism (e.g., actuator triggered by a clock or timer). Further, a biodegradable material may be configured to maintain an opening and, as time passes, to the material may dissolve, thereby increasing a level of blood flow restriction over time.

By way of non-limiting example, FIG. 4A-4C depict variable occluder 102 in an open state, in which flap 404A is open and permitting a reduced flow of fluid therethrough (e.g., as depicted by flow arrow 470). Further, FIG. 5A-5C depict variable occluder 102 in a closed state, in which flap 404A is closed and permits substantially no flow of fluid therethrough. Flap 404A may be transitioned or controlled between an open state and a closed state by flexible frame 405. In some examples, flexible frame 405 may include a time-dependent mechanism to increase a level of blood flow restriction through variable occluder 102 by closing flap 404A.

In some embodiments, a method may further include sensing pressure upstream of the variable occluder. As used herein, sensing refers to detecting or measuring a property or condition in or of an environment. For example, a sensor may be configured to sense a variable associated with an environment, such as a pressure in a biological structure (e.g., at least a portion of the venous system of the myocardium). As used herein, upstream refers to a direction against normal antegrade flow. For example, upstream in a coronary sinus may include a location in the coronary sinus closer to the myocardium. Downstream refers to a direction of normal antegrade flow. For example, downstream in a coronary sinus may include a location in the coronary sinus closer to the right atrium.

In some embodiments, a method may further include increasing the level of blood flow restriction in response to a drop in upstream pressure. As used herein, upstream pressure refers to the pressure associated with an upstream region with respect to a direction of natural flow. As used herein, a drop in pressure or decreasing pressure refer to a decrease or reduction in pressure in an environment or across a structure. For example, a drop in pressure or a decrease in pressure may be detected by a pressure sensor. In some examples, a drop in pressure or decrease in pressure may be a result of venous system compensation (e.g., angiogenesis providing a new, alternate flow path for retrograde blood flow).

Additionally or alternatively, in some embodiments, a variable occluder may be configured such that the level of blood flow restriction increases as a result of decreasing pressure on an upstream side of the occluder. Upstream pressure with respect to a variable occluder implanted in a coronary sinus may include the pressure within the coronary sinus on a side of the variable occluder farthest from the right atrium.

Figures 8A, 8B:
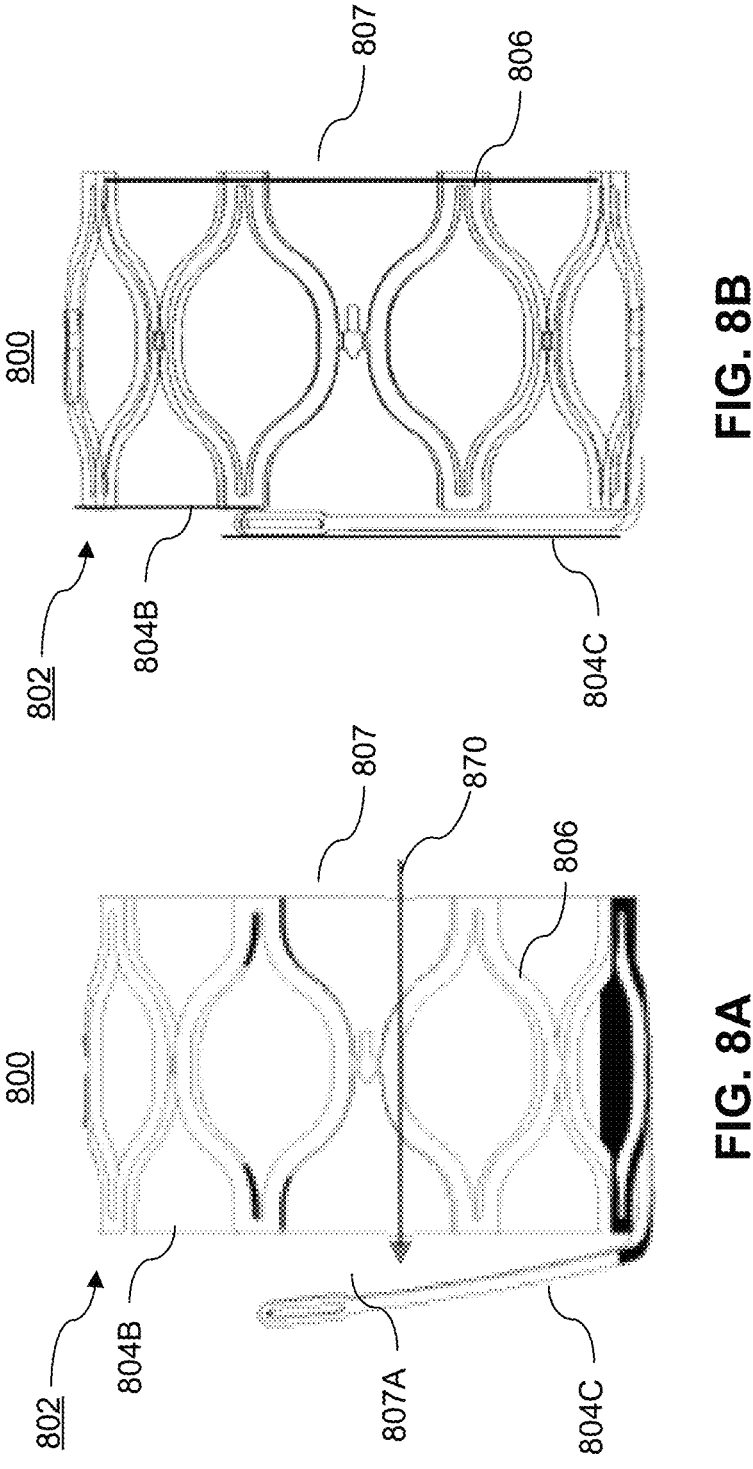
FIG. 8A is a side view of another example occluder in an open state, consistent with some disclosed embodiments.
FIG. 8B is a side view of the example occluder illustrated in FIG. 8A in a closed state, consistent with some disclosed embodiments.
Figures 9A, 9B:
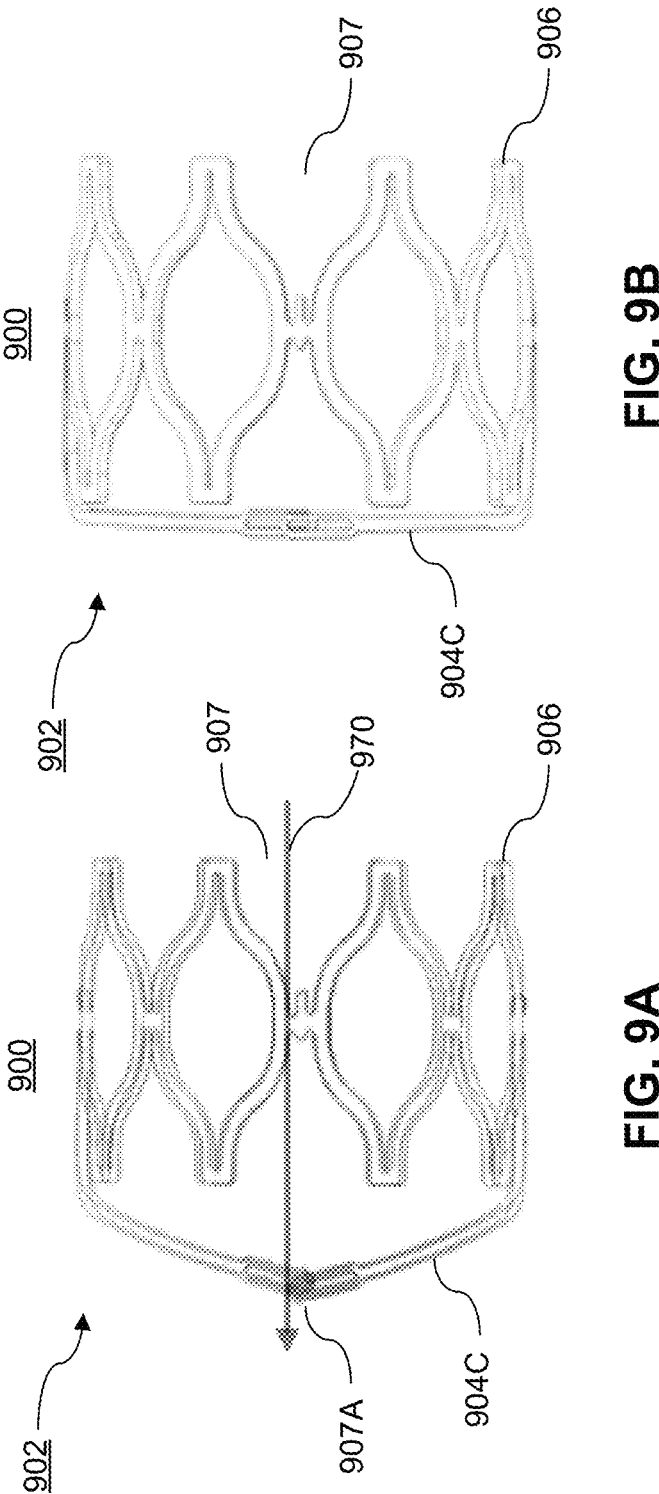
FIG. 9A is a side view of another example occluder in an open state, consistent with some disclosed embodiments.
FIG. 9B is a side view of the example occluder illustrated in FIG. 9A in a closed state, consistent with some disclosed embodiments.

By way of non-limiting example, FIGS. 4A, 5A, 7A depict flexible frame 405; FIG. 8A depicts flap sheet 804C (having a flexible frame and sheet); and FIG. 9A depicts flap sheet 904C (having a flexible frame and sheet). Any of the aforementioned elements may be configured to control an amount or degree to which flap 404A is opened. As illustrated, flexible frame 405 acts as a stop, restricting amount of permitted movement of flap 404A. For example, flexible frame 405 may be constructed with properties permitting varying degree of flex depending on the fluid force applied (or the force delta acting on flexible frame 405). In this example, flexible frame 405 is configured to decrease the amount or degree to which flap 404A is open (i.e., increase a level of blood flow restriction) as a function of pressure.

The degree of flex permitted (and hence the relationship between applied pressure and the degree of valve opening/closing), is a function of design choice for achieving a goal of venous system remodeling. Specific pressure ranges are described elsewhere herein. As the venous system adjusts or remodels as the result of increased upstream pressure (i.e., a higher volume of blood flows in a retrograde manner through branches of the venous system of the myocardium, the pressure will drop on the upstream side of device 400. As the pressure drops over time, the occluder will gradually close as the result of less upstream blood pressure against the occluder. In this way, gradual venous system remodeling may be achieved.

By way of non-limiting example, FIG. 5A-5C depict flap 404A of variable occluder 102 in a closed state. Flap 404A may be configured to close (i.e., increase a level of blood flow restriction) by flexible frame 405 due to a drop in upstream pressure (e.g., as detected by pressure sensor 108 or simply as the result of lower force exerted on the upstream side of the flap 404A). In another example, FIG. 4A-4C depict flap 404A in an open state. Flap 404A may be configured to open based on a force exerted by a pressure upstream of flap 404A (e.g., as indicated by flow arrow 470), and flexible frame 405 may be configured to close flap 404A. As the pressure upstream of flap 404A decreases (thereby decreasing the opening force exerted by said pressure), the closing force exerted by flexible frame 405 may gradually close flap 404A (thereby increasing a level of blood flow restriction).

Opening and closing of the occluder may follow a design gradient where an amount of closure adjusts incrementally based on the applied pressure. For example, the occluder may be designed so that each increment of pressure drop is precisely (or generally) calibrated to respond to applied pressure (or pressure delta across the occluder), ensuring a controlled and predictable change in closure. That is, the occluder may close according to a designed amount, each increment of which is a function of pressure applied or a delta in pressure across the occluder. The gradient may not necessarily be precisely calibrated. It may be sufficient that, generally speaking, as pressure drops, occlusion increases.

By way of non-limiting example and with reference to FIG. 1A, increased pressure in coronary sinus 130 caused by implanted variable occluder 102 may induce angiogenesis to provide a new, alternate flow path for blood in branches upstream of the occluded region. As depicted in FIG. 1A, flow arrow 170 may represent antegrade deoxygenated blood flow from the myocardium and flow arrow 171 may represent alternate retrograde deoxygenated blood flow.

Additionally or alternatively, venous system compensation may include establishing a positive pressure gradient. A positive pressure gradient refers to a positive difference in pressure between the blood pressure in a left heart chamber (e.g., left atrium) and the blood pressure at a location upstream an implanted variable occluder (e.g., within coronary sinus region proximate the left atrium). The positive pressure gradient may, if the left heart chamber and location upstream the implanted variable occluder were flow connected, facilitate a flow of fluid from the left heart chamber into the location upstream the implanted variable occluder, including in a retrograde direction. By way of non-limiting example, a positive pressure gradient may be more than 2 mmHg, 4 mmHg, 5 mmHg, 8 mmHg, or 10 mmHg.

In some embodiments, a method may include determining the venous system compensation by comparing blood pressure in the left atrium with blood pressure upstream of the variable occluder. Measurements of pressure may be taken at each location to determine that the pressure differential between the left atrium and the coronary sinus is sufficient to establish retrograde flow following a bridging shunt implantation. In some examples, venous system compensation may be determined directly via imaging techniques, such as ultrasound imaging, magnetic resonance imaging (MRI), magnetic resonance venography (MRV), computed tomography (CT), or CT venography (CTV). Additionally or alternatively, in some examples, venous system compensation may be determined indirectly, including by measuring any hemodynamic parameter, such as central venous pressure (CVP), arterial pressure, pulmonary artery pressure (PAP), cardiac output (CO), systemic vascular resistance (SVR), wedge pressure, flow rate in at least a portion of the coronary venous system, a density of blood in the coronary venous system, a viscosity of blood in the coronary venous system, or any other suitable hemodynamic parameter known to those skilled in the art. Further, the hemodynamic parameter may be measured in resting or active state of a patient. Additionally or alternatively, the hemodynamic parameter may be measured under a full occlusion or a partial occlusion, including as provided by a variable occluder implanted in a blood vessel (e.g., coronary sinus).

In some embodiments, a method may include, following venous system compensation, shunting oxygenated blood flow into the coronary sinus. Shunting refers to taking an action which causes blood to flow from one biological structure to another. This may be accomplished by implanting a shunt, which may include any structure capable of bridging two biological structures, such as a heart chamber and a blood vessel. For example, the shunt may be configured for deployment in a passageway between a first biological structure and a second adjacent biological structure. For example, an opening may be formed in each structure and a shunt implanted through both openings to form a bridged passageway.

In some embodiments, shunting oxygenated blood flow into the coronary sinus may be from the left atrium. This may occur, for example, by implanting a shunt between the left atrium and the coronary sinus. This shunting may occur following venous system compensation as described earlier, enabling the venous system of the myocardium to adapt to increased pressure levels such as those found in the left atrium. After the venous system compensation occurs, the venous system of the myocardium should be sufficiently adjusted or remodeled to handle greater pressure of blood shunted from the left atrium.

The shunt may be deployed in a passageway (formed by piercing the tissue) between two cavities such as the coronary sinus and the left atrium. This piercing may occur using any number of procedures and/or devices, and the method of this disclosure is not necessarily limited to any particular procedure or device. deployment may pertain to the positioning or placement of a device or component in the body. In a broadest sense, a passageway may occur any channel or opening that allows a fluid, such as blood, to flow through. The passageway may be formed by a pre-incised hole. Furthermore, in some embodiments, the shunt may be configured to bridge a first cavity in the first biological structure and a second cavity in the second biological structure. The bridging of the first cavity in the first biological structure and the second cavity in the second biological structure may include providing a structure that allows fluid to flow between the first cavity and the second cavity. It is contemplated that the first biological structure and the second biological structure may be any biological organ or structure such as—but not limited to—blood vessels, anatomical cavities, and/or anatomical chambers. Furthermore, a shunt may redirect the flow of bodily fluids, as discussed further herein.

One non-limiting example of a shunt includes shunt 140, as depicted in FIGS. 1C and 15 and as described and exemplified elsewhere herein. Other examples of shunts that may be employed with the methods described herein include those described in PCT/IB2023/051918, the contents of which are incorporated herein by reference.

In some embodiments, a shunt may include a frame with a biocompatible flexible material to allow transition between a compressed state suitable for transvascular delivery via a catheter and an expanded state. The flexible material may include any material providing the desired effect but being safe for use in a human for a period of time and at times, an extended period of time. The choice of flexible material may prevent the shunt from interfering with natural contraction of the atrial chamber. It may additionally have non-uniform flexibility to improve its function within the heart. Note that all metal outer edges such as those of the frame may be rounded to reduce trauma to the tissue in contact. In addition, the flexibility of the outer edges which engage with tissue may have a higher degree of flexibility. The frame portion of the shunt may interconnect with a stabilizer portion and/or to the flow-deflecting portion. Relevant flexible materials will be recognized by those skilled in the art. Such materials include those which provide strength to resist deformation over time, have ability to expand due to pressure decrease on outer circumference and are flexible for tolerance of a range of anatomy variance. Non-limiting examples may include a super elastic alloy, and/or a shape memory material, such as a shape memory alloy (SMA) such as a nickel-titanium alloy otherwise known as nitinol or NiTiCu (nickel titan copper), CuZn (copper zinc), CuZnAl (copper zinc aluminum) and/or CuAlNi (copper zinc nickel). Other suitable materials may include other metals or stainless steels. The flexible material may be further be coated and or textured to increase biocompatibility for improved blood flow, and optimal engagement with tissue in a pre-incised hole. In some embodiments, the flexible material-based frame structure may be further covered or coated by a pliable material (such as a fabric cover) forming a pliable covering to further increase biocompatibility or serve as a continuous sheet for portions other than the shunt (e.g., the flow deflector). The pliable material may have increased flexibility over the flexible material mentioned in the context of the frame structure. In some embodiments, the pliable covering is at least partially impermeable to fluid and specifically blood flow. In some embodiments, the pliable covering is substantially impermeably to fluid and specifically blood flow. In some embodiments, the pliable covering is porous. In some embodiments, the pliable material is configured to seal a stabilizer such as an anchor or a flange against a wall of the heart chamber upon deployment.

In some embodiments, a shunt may include a tubular region ending in a perimeter edge opening on a distal end of the tube as well as a stabilizer (e.g., flange) extending from the tubular region. The stabilizer (e.g., flange) may be located on a side of the tubular region opposite the deflector portion (i.e., the distal end of the shunt structure). In some examples, the stabilizer (e.g., flange) may be configured to contact a wall of the heart chamber upon deployment. The flange may contact the internal wall of a heart chamber such that a seal is formed and substantially no blood passes between the flange and the internal wall of the heart chamber. The flange may have a radius of curvature at different points. The flange may be asymmetrical in terms of the radius of curvature at different locations or length of flange at different locations.

In some embodiments, the stabilizer or flange may include a frame making up a plurality of arms configured to contact, engage, or seal the stabilizer or flange against a wall of the heart chamber upon deployment. An additional stabilizer may be located on a side of the tubular region adjacent to the flow deflector (e.g., the proximal end of the shunt). In some embodiments, the shunt may include a tubular region and an anchor extending from the tubular region.

In some embodiments, a shunt may include orientation markers to facilitate rotational orientation around the central opening of the shunt. The orientation markers may be configured to allow for control of rotational orientation of the shunt around the central opening. In some embodiments, this control of rotational orientation of the shunt around the central opening may define an extent of flow deflection in the second cavity or channel of vein (e.g., the coronary sinus). Orientation markers are known in the art and non-limiting examples may include tantalum makers or structural design at specific locations including for example a tether or wire.

In some embodiments, a tubular shunt may apply a radial force from the center of the shunt outwards for example, such that it applies a force on the tissue surrounding the pre-incised hole. The stabilizer portion may have a spring-like bias and facilitate compliant fixation within the passageway. In some embodiments, the tubular shunt may apply a radial force as well as a lateral force from the center of the shunt. In other examples, the stabilizer may have an inner diameter progressively decreasing from a distal to proximal end, for example the central passageway may be in the form of a cone which is configured to apply radial forces on the pre-incised hole thereby stabilizing the device or portions thereof. In this way, the stabilizer may exert a restraining force on the surface of the atrium inner wall or alternatively on the passageway, resisting shifting of the shunt in a direction towards the coronary sinus or flow deflector position. Thus, the stabilizer may be configured to ensure the shunt and/or flow deflector does not shift despite pressure applied.

The stabilizer may be integrally connected to the shunt and the flow deflector. In some embodiments, a single frame forms the structure of an intravascular device comprising the stabilizer, shunt structure and long-term flow deflector.

In some embodiments, the stabilizer portion may include a flange on a distal end of the shunt configured to contact an interior surface of a heart chamber such as the left atrium.

The flange may be configured to extend beyond a periphery of a distal end of the tubular shunt and into the first cavity of the first organ. In some examples, the flange on the distal end of the shunt may be configured to seal against an inner wall of the cavity in the organ. The flange may be a flexible flange, comprising a flat or flexible plate or sheet having an outer periphery and a flexible tube or flange frame arranged or adapted for stabilizing the flexible plate or sheet. In this case, the flange may be configured for location inside a heart chamber, the flange portion including a plurality outwardly extending prongs forming a portion of the frame. In some examples, each prong may have a distal end curved in a tissue-contacting direction. Disclosed embodiments are not limited to particular numbers of components and may include a different number of leaflets or prongs, for examples one, two, three, four, five, six, eight, nine, ten, eleven, or twelve.

In some embodiments, the stabilizer may include a flange on a distal end of the shunt and additionally include a second stabilizer having a plurality of prongs having a distal end curved in a vessel wall-contacting direction (i.e., coronary sinus wall) on a proximal end of the shunt structure.

In some embodiments, the stabilizer may be configured to recover substantially to its preloaded shape (i.e., prior to loading in the delivery catheter) following release from the delivery catheter. That is, the stabilizer may resist being pulled back through the distal opening of the delivery catheter.

In some embodiments, shunting blood flow from the left atrium into the coronary sinus may include transvascularly delivering a shunt. Transvascular component delivery is a process of deploying a component (in this instance a shunt) through the blood vessels to reach a target area. This method utilizes the body's vascular system as a pathway along which the shunt is advanced. In some instances, the pathway might also include intermediate organs such as heart chambers. For example, an incision may be made through the skin and a blood vessel near the skin, and a guidewire may be inserted into the blood vessel and advanced toward a region of the coronary sinus proximate the left atrium. In this instance, the pathway may include the right atrium.

In some embodiments, shunting blood flow from the left atrium to the coronary sinus may include transvascularly delivering a puncturing tool to the region of the coronary sinus proximate the left atrium. A puncturing tool refers to device or instrument configured to create an opening or perforation in a structure. For example, a puncturing tool may include a sharp tip, such as a needle, configured to pierce or puncture a biological structure (e.g., wall of heart chamber, wall of blood vessel). The puncturing tool may be transvascularly delivered using a catheter or guidewire.

Figure 18:
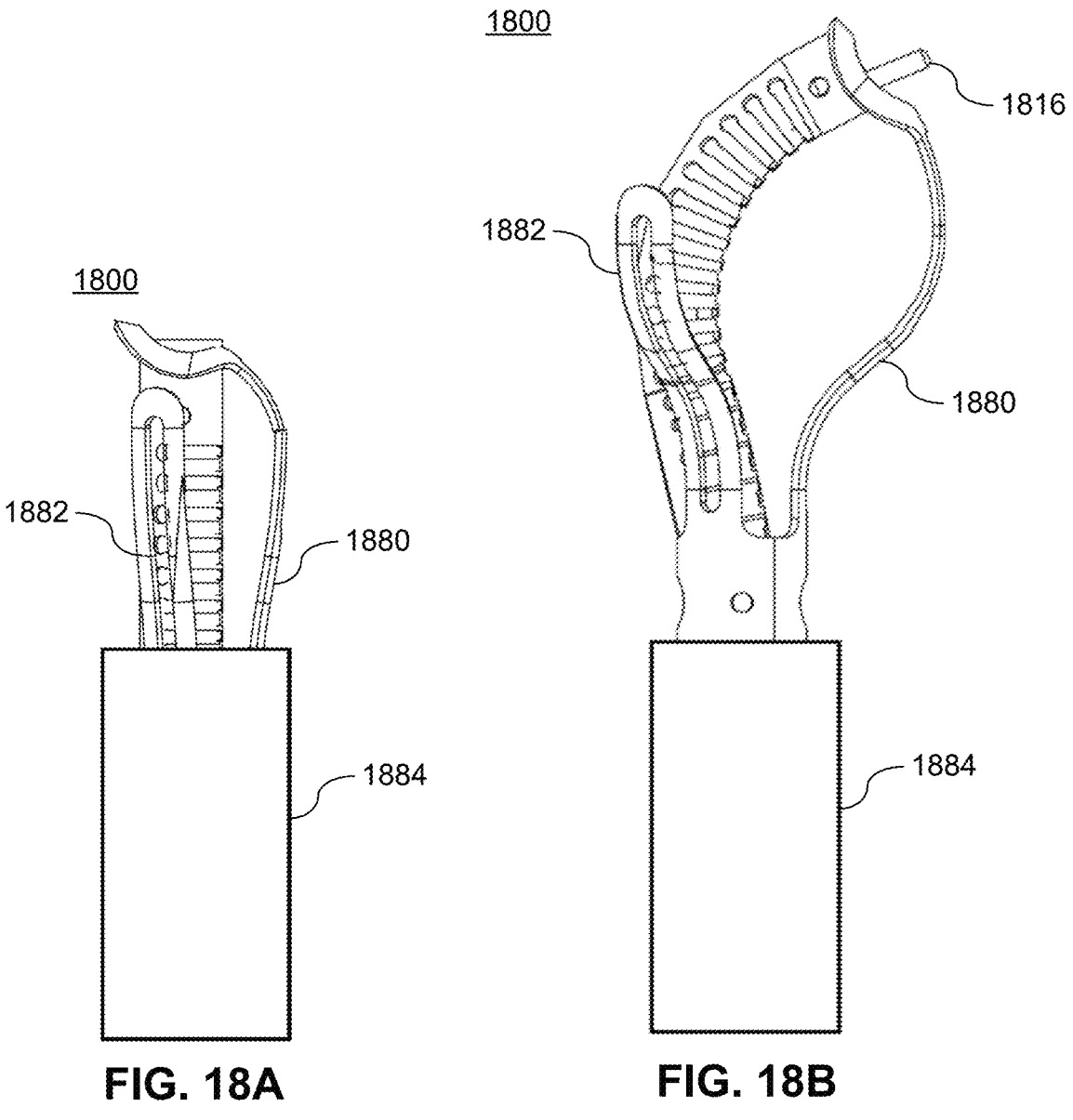
FIG. 18A is a side view of a puncturing tool in a compressed state, consistent with some disclosed embodiments.
FIG. 18B is a side view of the puncturing tool illustrated in FIG. 18A in an expanded state, consistent with some disclosed embodiments.

By way of non-limiting example, FIG. 18A depicts example puncturing tool 1800 in a compressed state for transvascular delivery (e.g., to a region of the coronary sinus proximate the left atrium). Puncturing tool 1800 may include a flexible positioning arm 1880. Flexible positioning arm 1880 may be configured to transition from a compressed state (e.g., as depicted in FIG. 18A) to an expanded state (e.g., as depicted in FIG. 18B). Further, puncturing tool 1800 may include a flexible support arm 1882. Flexible support arm 1882 may be substantially more flexible than flexible positioning arm 1880 and may be configured to cooperate with flexible positioning arm 1880 to secure puncturing tool 1800 against a wall of a vessel, such as a region of the coronary sinus proximate the left atrium (e.g., by moving, rotating, expanding, collapsing, twisting, or pressing). Flexible positioning arm 1880 and flexible support arm 1882 may be held or maintained in a compressed state within a sheath 1884 such that when sheath 1884 is pulled away, flexible positioning arm 1880 and flexible support arm 1882 are released into their respective expanded states. Puncturing tool 1800 may include a puncturing component 1816 having a sharp edge. Other non-limiting examples of puncturing tools are disclosed in PCT Application No. PCT/IB2023/061707 (incorporated herein by reference), any of which may be used to form a perforation through the coronary sinus and the left atrium.

A catheter containing the shunt may be advanced along the guidewire and into the perforation, where the shunt may open in a self-expanding manner (e.g., following release from a sheath), with a balloon, using mechanical means, or in any other manner.

Figure 19:
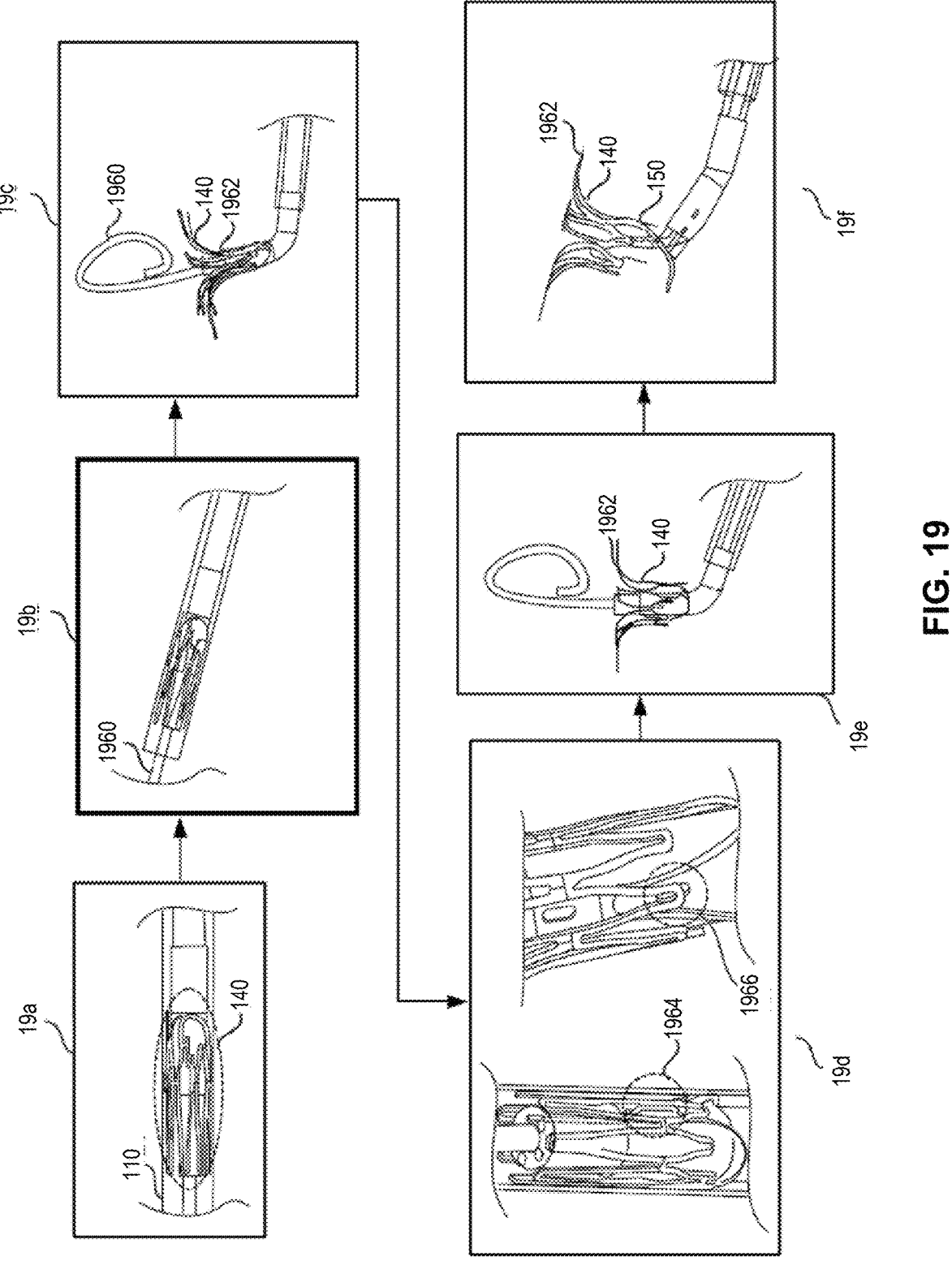
FIG. 19 is a graphical flow chart of an example process for implanting a shunt, consistent with some disclosed embodiments.

By way of non-limiting example and as shown in FIG. 19, in step 19*a*, shunt 140 may be placed inside tool 110 in a compressed configuration, where shunt 140 may be compressed around or adjacent to guide wire 1960. If flow deflection is desired, in the compressed configuration, flow deflector 150 may be configured to nest (e.g., be placed, at least partially, or enclosed) within shunt 140. In other embodiments of the compressed configuration, flow deflector 150 may be configured to run parallel and adjacent to shunt 140. Tool 110 may be placed in the body of a patient, and tool 110 may traverse through vasculature of the patient to reach a desired location of deployment.

As shown in step 19*b*, tool 110 may be pulled back to cause expansion of shunt 140 from its compressed configuration. As shown in step 19*c*, stabilizer 1962 of shunt 140 may expand or unfold as tool 110 continues to be pulled back. Step 19*d* shows examples of trigger wire mechanisms 1964 and 1966. Trigger wire mechanisms 1964 and 1966 may be used for selective expansion of flow deflector 150 following the expansion of stabilizer 1962 (which may include a flange portion) and shunt 140. Upon ejection from tool 110, trigger wire mechanism 1964 and 1966 associated with flow deflector 150 may be pulled, releasing flow deflector 150 for further expansion.

As shown in step 19*e*, flow deflector 150 may include a catch for maintaining flow deflector 150 in at least a partially non-expanded configuration upon ejection from tool 110. Flow deflector 150 may be configured to extend through tool 110 in a first direction, and the trigger wire mechanism 1964 and 1966 may be configured such that when pulled from the first direction, flow deflector 150 may expand towards a second direction (e.g., as shown in step 19*f*), opposite the first direction. When ejected (e.g., deployed, expanded) from tool 110, shunt 140 may be configured to expand into a tubular shape and flow deflector 150 may be configured to expand into a bowed (e.g., curved, rounded, arched) form, as shown in step 19*f*.

Other non-limiting examples of implanting a shunt and flow deflector are further described in PCT Application No. PCT/IB2023/051918, the entire contents of which are incorporated herein by reference. The above are just examples. In their broadest sense, the methods described herein are not limited to any particular structures.

By way of non-limiting example, FIG. 1C depicts shunt 140 implanted between left atrium 120 and coronary sinus 130, thereby providing passageway 142 through which oxygenated blood may flow from left atrium 120 into coronary sinus 130. Further, in providing passageway 142, shunt 140 may facilitate a flow of oxygenated blood from the left atrium 120, thereby decreasing a left atrial pressure of left atrium 120. Decreasing the left atrial pressure may provide a pressure relief for a left atrium having an increased or elevated (with respect to typical or expected) left atrial pressure, which may be used to treat a patient having mildly reduced (HFmrEF) or preserved (HFpEF) ejection fraction heart failure with elevated left atrial pressure. The shunted oxygenated blood may optionally flow in the coronary sinus in a retrograde direction as deflected by a flow deflector, such as flow deflector 150 (e.g., as indicated by flow arrows 172), as further described and exemplified elsewhere herein.

As referred to earlier, in some embodiments, shunting blood flow from the left atrium to the coronary sinus may include manipulating the puncturing tool to form the passageway through a wall of the coronary sinus and a wall of the left atrium. As used herein, manipulating refers to controlling, guiding, or adjusting a device, component, or tool in order to accomplish a particular task or operation. For example, manipulating a puncturing tool may include adjusting or moving the puncturing tool to puncture a surface at an intended location.

A wall refers to a structure or boundary that separates or defines different spaces. For example, a wall of the coronary sinus may include the tissue structure that defines the outer boundary or layer of the coronary sinus. Similarly, a wall of the left atrium includes the tissue structure that defines the outer boundary or layer of the left atrium.

By way of non-limiting example, FIG. 2 depicts tool 110 with puncturing end 216 configured to puncture a surface of a structure. Further, FIG. 2 depicts tool 110 with orientation marker 214. Orientation marker 214 may aid a clinician in correctly positioning and orienting tool 110 to or at a desired location. In some examples, orientation marker 214 may include a radiopaque material (e.g., gold, platinum) visible under fluoroscopy or X-ray imaging. Orientation marker 214 may be used to position tool 110 at a desired location, such as in a region of the coronary sinus proximate the left atrium. Then tool 110 may be manipulated such that puncturing end 216 (e.g., puncturing tool 1800 depicted in FIG. 18) punctures the wall of the coronary sinus and the wall of the left atrium, thereby forming a passageway between the coronary sinus and the left atrium.

In some embodiments, implanting a shunt may include delivering the shunt through a punctured variable occluder. For example, when the shunt is to be implanted at a location on an opposite side of the variable occluder, a tool (e.g., catheter) containing the shunt in a compressed state may be configured to puncture or pierce and cross the variable occluder before deploying the shunt.

By way of non-limiting example, FIG. 6A-6D depict device 600 with a flexible frame 405 having a discontinuous portion 605A. Discontinuous portion 605A may include two ends 605B and 605C (best viewed in FIGS. 6C and 6D) that permit flexible frame 405 to stretch or increase in circumference at discontinuous portion 605. In this way, when a tool, such as tool 110 containing shunt 140 in a compressed state, pierces or crosses an occluding surface (e.g., flap 404A, fixed portion 404B), flexible frame 405 may stretch or expand to permit the passage of tool 110 therethrough.

In some embodiments, shunting oxygenated blood flow into the coronary sinus may cause retrograde flow of oxygenated blood in at least part of the venous system of the myocardium. For example, a pressure differential between the left atrium and the coronary sinus may facilitate retrograde blood flow in the coronary sinus after shunting. In some embodiments, a method may further include deploying a flow deflector in the coronary sinus to deflect left atrium blood flow in a retrograde direction. In some embodiments, shunting oxygenated blood flow into the coronary sinus to cause retrograde flow of oxygenated blood in at least part of the venous system of the myocardium may be achieved using a shunt and flow deflector, such as disclosed in PCT/IB2023/051918 (the entire contents of which are incorporated herein). A flow deflector refers to a device or component configured to direct, guide, steer, or redirect a flow. Deflecting may or may not result in an overall change in direction of some or all flow from a first direction to a second direction. In some embodiments, the second direction may be opposite to the first direction. In other embodiments, the second direction may be perpendicular to the first direction. It is contemplated that the second direction may be perpendicular to, parallel to, or angled relative to the first direction.

The flow deflector may have a bowed frame. A bowed frame is a frame that is bent. The bowed frame may have a scoop configuration of a curved or hollowed shape. In some embodiments, the flow deflector may form a crescent shape extending from the shunt structure. A crescent shape is a curved, moon-like form that is wider in the middle and tapers at both ends. Some embodiments involve a scoop trough that is generally circular in shape in its cross-sectional profile. The flow deflector may be configured to extend from the shunt structure and have the shape of a scoop similar to a spoon. The scoop shape may be non-tubular and may be sized to cover a full cross section of the cavity or vein (e.g., coronary sinus).

The end of the flow deflector may be configured to contact or engage with a wall portion of the blood vessel opposite the passageway i.e., contact the opposing side of the vein opposite the passageway or pre-incised hole. In some embodiments, the deflector may be sized to terminate against a wall of the blood vessel opposite the passageway. In some embodiments, the long-term flow deflector may include an edge or lip configured for engaging a wall of the coronary sinus. Consistent with some embodiments, the distal edge or lip may be flexible and configured to flex against a wall of the vein. The flow deflector may include a distal edge or lip biased to conform to a curvature of the coronary sinus. The distal scoop-shaped flow deflector may have additional flexibility at the edges or lip in order to accommodate a range of anatomy and patient to patient variance. Although the flow deflector may be shaped to cover a full cross-section of the vein, the degree of flow deflection may be controlled by shunt structure rotation such that depending on the shunt positioning, the degree of flow deflection may be controlled. In some embodiments, the flow deflector is shaped to cover a full inner perimeter of the vein.

The flow deflector may have a scoop or arc-shaped concavity sized to cover most or all of an inner circumference of the vein or coronary sinus such that it extends mostly or entirely across the entire passageway in the vein. In some examples, the flow deflector may be sized to contact a perimeter of a cavity or span the cross section of the vein.

In some embodiments, the flow deflector may include a shunt structure as well as a flexible flow-deflecting cover, also referred to as a pliable covering. In some examples, a flexible flow deflecting cover may be located on the metal flow-deflecting portion such that the flow-deflecting portion and the flexible flow-deflecting cover are configured, upon expansion, to deflect blood flow from the heart chamber in a retrograde manner within the coronary sinus.

The shunt structure may be made of a biocompatible elastically deformable material or shape memory material with sufficient flexibility and rigidity to tolerate changes in the heart chamber, passageway and vein when deployed. The flexible flow-deflecting cover on the metal flow-deflecting portion being configured, upon expansion, to deflect blood flow from the heart chamber in a retrograde manner within the coronary sinus.

In some embodiments, the flexible flow-deflecting cover may include a fabric, mesh polymer coating, synthetic material or coating or combinations thereof. The flexible flow-deflecting cover may be configured to extend over the stabilizer portion and cover at least 50% of the scoop shape. In some embodiments, the flexible flow-deflecting cover may be configured to extend over the stabilizer portion and cover at least 70% of the scoop shape. In some embodiments, the flexible flow-deflecting cover may be configured to extend over the stabilizer portion and cover at least 90% of the scoop. In some embodiments, the flexible flow-deflecting cover may be configured to extend over the stabilizer portion and cover at least 95% of the scoop shape.

The flexible flow-deflecting cover may include a fabric, mesh, polymer coating or synthetic material configured to limit blood flow. Such a cover may include a fine mesh or woven material. In some embodiments, the pliable covering may be at least partially impermeably to fluid and specifically blood. Non-limiting examples may include nylons, polyethylene, EPTFE, TPU and PTFE.

The flow deflecting portion may be configured for location in a vein and in specific embodiments, in a coronary sinus. The flow deflecting portion may be movable between an expanded position and a retracted position. The shunt structure may form a frame for the cover and provide sufficient resilience, wherein a sufficient resilience may include a resilience to be compressed to a reduced diameter for delivery in a delivery catheter. The shunt structure may also provide sufficient rigidity, wherein a sufficient rigidity may include a rigidity to maintain a deployed shape.

In some embodiments, the flow deflecting portion, when in the expanded position, may be configured to promote flow deflection within a vessel (e.g., coronary sinus) by limiting passage of blood therethrough and further be configured to allow passage of tooling through a tool passage. The tool passage may have any shape or structure that is adapted to allow a tool to pass after deployment without compromising a substantially liquid tight seal or flow deflection.

In some embodiments, the shunt structure may be configured as a tube, sized to meet the inner circumference of the coronary sinus.

In some embodiments, a cover may be positioned to extend over the circular base portion of the shunt resembling a tube and may be configured to block passage of blood, while allowing for passage of a device such as a deployment device therethrough via a tool passage. Blocking passage of blood may be a delayed process where blood or newly forming tissue may play a role in the blocking process over time.

Figure 17:
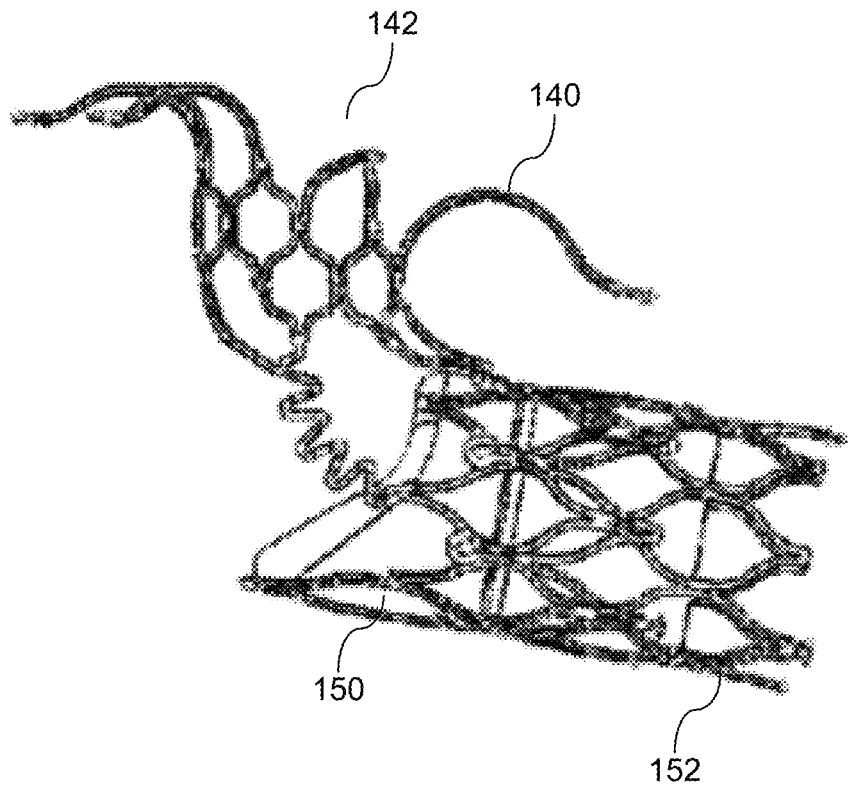
FIG. 17 is an isometric view of an example shunt and flow deflector with a variable occluder (in a deactivated flow restriction state), consistent with some disclosed embodiments.

By way of non-limiting example, FIG. 17 depicts flow deflector 150 configured to deflect a flow of oxygenated blood from passageway 142 of shunt 140. In some embodiments, shunt 140 and flow deflector 150 are implanted in left atrium 120 and coronary sinus 130 adjacent to the a flow restriction deactivated variable occluder 102A. In another non-limiting example, FIG. 1C depicts shunt 140 and flow deflector 150 respectively implanted in left atrium 120 and coronary sinus 130. As depicted in FIG. 1C, oxygenated blood may flow through passageway 142 into coronary sinus 130, in which flow deflector 150 deflects the shunted oxygenated blood in a retrograde direction in coronary sinus 130 (e.g., as indicated by flow arrows 172). As illustrated in FIG. 1C, the flow deflector 150 is located downstream of shunt 140.

In some embodiments, a shunt and a flow deflector may be integrally formed. Integrally formed refers to a component or device that is made or assembled as a single, unified piece. For example, a shunt and a flow deflector may be integrally formed using 3D printing, laser sintering, laser cutting, braiding and weaving, electroforming and electrospinning, chemical etching, or molding, and/or extrusion.

By way of non-limiting example, FIG. 17 depicts shunt 140 and flow deflector 150 integrally formed as a single component.

Additionally or alternatively, a shunt and a flow deflector may be formed as two separate components which may or may not be connected. For example, a shunt and a flow deflector may be connected by a tether or an engagement feature. A tether refers to a component or device configured to provide a connection that links one object to another. For example, a tether may include a wire, braid, suture, coil, fiber, rod, or other linkage. The tether may be formed of PTFE, polyurethane, bioabsorbable polymers, biocompatible polymers (e.g., polyurethane, expanded polytetrafluoroethylene) or metals (e.g., nitinol, titanium, titanium alloys). A flow deflector may include an engagement feature configured to mate with a corresponding engagement feature of a shunt and/or a variable occluder. An engagement feature refers to a structural or mechanical component or device configured to secure, anchor, align, or interlock two or more components or devices. For example, an engagement feature may include barbs, hooks, screws, clamps, clips, or magnets.

In some embodiments, retrograde flow of oxygenated blood in at least part of the venous system of the myocardium may enable revascularization of the myocardium. Revascularization refers to the process of providing blood flow to an area of the body that is experiencing or has experienced reduced or blocked blood supply. The lack of sufficient blood flow may cause ischemia, where tissue is damaged or dies due to insufficient oxygen and nutrients. For example, retrograde flow of oxygenated blood in the coronary sinus may flow to the myocardium through blood vessels, including preexisting blood vessels and/or those created by angiogenesis due to an increased pressure upstream of an implanted variable occluder. In this way, the oxygenated blood may flow to the myocardium, thereby revascularizing the myocardium.

Revascularization of the myocardium may be achieved using the structures illustrated in FIG. 1C, for example. In FIG. 1C, blood from the left atrium 120, enters coronary sinus 130 through passageway 142 of shunt 140. The deployment of flow deflector 150 downstream of the shunt 140, at least partially if not entirely blocks blood flow in an antegrade direction, causing blood to flow in a retrograde direction through the tributaries of coronary sinus 130. Thus, portions of the venous system of the myocardium, which typically deliver deoxygenated blood from the myocardium to the coronary sinus and then to the right atrium, function as arteries for delivering oxygenated blood to the myocardium. This may be particularly beneficial for treating ischemic tissue in the myocardium. It may also be helpful in treating heart failure by reducing excessive pressure in the left atrium.

In some embodiments, a method may include, following the venous system compensation, at least partially deactivating flow restriction by the variable occluder to thereby enable retrograde blood flow from the left atrium in the coronary sinus. Deactivating flow restriction refers to disabling or rendering a device or component inactive or non-operational. By way of non-limiting example, at least partially deactivating flow restriction may include perforating a portion of an occluder, dilating the flow restriction of the occluder, removing a flow restrictor, or adjusting the occluder or flow restrictor in a way that at least partially renders its occlusion function ineffective. For example, deactivating flow restriction may include crossing the variable occluder with a tool such as a puncturing tool disclosed in PCT Application No. PCT/IB2023/061707 (incorporated herein by reference). In another example, deactivating flow restriction may include adjusting a geometry of an occluding surface, for example by expanding an opening therein. Adjusting a geometry of an occluding surface may include transvascularly crossing or piercing the occluding surface with an expandable element. In another example, a volume of the flow restriction may be decreased by collapsing or deflating an inflatable occluder. When flow restriction is accomplished using a sheet, a membrane or other perforable material, perforation either alone or in combination with outward compression may disable the flow restriction. For example, a stent may be expanded (self-expanding or with a balloon) within the occluder to compress the flow restrictor toward the vessel wall, thereby rendering the flow restrictor completely or partially ineffective. In some instances, balloon expansion alone without a stent may be sufficient to disable the flow restrictor of the occluder. Alternatively, other types of restriction structures may be collapsed, disintegrated, or absorbed. Such processes may involve drugs or other means of inducing controlled or timed disintegration. Controlled disintegration may include a chemical or temperature-sensitive degradation. Perforating the transient occluder may refer to introducing a single hole or multiple holes. Introducing a hole may include drilling, piercing, or punching a hole in the transient occluder. Alternatively, deactivating flow restriction may include any means of manipulating an occluder or its occluding surface, which may include transvascularly crossing the variable occluder with tool having a diameter greater than the opening.

As discussed, at least partially deactivating flow restriction may include transvascularly crossing the variable occluder with an expandable element. As used herein, crossing refers to crossing refers to moving from one side of a boundary, surface, plane, or dividing line to another side. For example, in some embodiments, crossing may occur through penetration of a thin surface of material, while in other embodiments crossing may occur by passing through a thicker piece of material, such as a plug or other seal.

By way of non-limiting example, FIG. 1B depicts tool 110 puncturing and crossing occluding surface 104 of variable occluder 102. In this way, an opening is created in occluding surface 104, thereby eliminating or greatly reducing—including permanently—the level of blood flow restriction through variable occluder 102 and permitting a level of antegrade deoxygenated blow flow therethrough (e.g., as indicated by flow arrow 170). In another example, deactivating flow restriction may include deactivating a component controlling an occluding surface, such as a flexible frame. By way of non-limiting example, FIG. 7A-7C depict flexible frame 405 in a deactivated state. Flexible frame 405 may be deactivated by expansion of an expandable element of a tool after puncturing and crossing occluding surface 104, such as tool 110 depicted in FIG. 2. In the deactivated state, flexible frame 405 is no longer contacting or controlling flap 404A. In this way, the level of blood flow restriction of variable occluder 102 is no longer controllable by flexible frame 405. In some embodiments, the flexible frame 405, or other suitable structures, might be adjusted or bent inwardly, pressing flap 404A toward the coronary sinus wall.

As discussed, any expandable element may be used to deactivate the flow restriction. Such structures include but are not limited to self-expanding structures like stents, expandable balloons, shape memory expandable structures, braided expandable structures, or any other biocompatible mechanism capable of expansion.

A balloon refers to a flexible, inflatable component, element, device, or instrument configured to be expanded using a gas (e.g., air) or a fluid (e.g., saline). For example, a balloon may be configured for transvascular delivery into a blood vessel (e.g., coronary sinus) and, once positioned at a desired location, inflated (e.g., using saline, air) and subsequently deflated. If a stent is deployed for deactivating the flow restriction, the stent may be either self-expanding or balloon-expandable. By way of non-limiting example, expandable element 112 may include a stent, such as stent 106 or stent 152.

In some embodiments, an expandable element may include a stent retriever. As used herein, a stent retriever refers to a device or component configured to remove an obstacle or obstruction from a structure. For example, a stent retriever may include a self-expanding metal mesh that, when expanded at a desired location, traps an obstacle or obstruction, such as a variable occluder, such that when the stent retriever is removed, the trapped obstacle or obstruction is removed as well.

By way of non-limiting example, expandable element 112 depicted in FIG. 2 may be a balloon. Additionally or alternatively, expandable element 112 depicted in FIG. 2 may be a stent. Additionally or alternatively, expandable element 112 depicted in FIG. 2 may be a stent retriever configured to remove an implanted stent.

In some embodiments, at least partially deactivating flow restriction may include compressing an occluding portion of the variable occluder against a wall of the coronary sinus. As used herein, compressing may refer to reducing a size or a volume of an instrument, element, component, or device. For example, a compressed variable occluder may have a smaller occluding surface area with respect to the biological structure being occluded such that an amount of flow through or past the variable occluder is increased compared to a non-compressed variable occluder.

By way of non-limiting example, FIG. 1B depicts tool 110, including expandable element 112, having punctured and crossed occluding surface 104 of variable occluder 102. Expandable element 112 may be configured to expand while located within occluding surface 104, thereby creating an opening in and deactivating variable occluder 102 and enabling retrograde blood flow from the left atrium in the coronary sinus. In one non-limiting example, expandable element 112, when expanded, may compress occluding surface 104 of variable occluder 102 against a wall of coronary sinus 130. In another non-limiting example, expandable element 112, when expanded, may trap at least a portion of variable occluder 102, such as occluding surface 104, such that when tool 110 is removed, the at trapped portion of variable occluder 102 is removed as well.

In some embodiments, a variable occluder may be configured to enable simultaneous antegrade blood flow in the coronary sinus with retrograde flow in branches off of the coronary sinus. In other embodiments, some antegrade flow may occur downstream of the occluder, while retrograde flow occurs upstream of the occluder. As used herein, simultaneous refers to occurring, operating, or being done at substantially a same time. For example, simultaneous retrograde and antegrade blood flow in the coronary sinus may include a flow of blood in the coronary sinus in either or both a retrograde (e.g., toward the myocardium) or an antegrade (e.g., toward the right atrium) direction. In other words, some blood may flow in an antegrade direction in the coronary sinus (e.g., blood that passes the occluder), while other blood either flows in a retrograde direction in the coronary sinus or in a retrograde direction through vessels branching from the coronary sinus.

By way of non-limiting example, a particular pressure gradient across variable occluder flap 404A depicted in FIG. 4A-4C may cause flap 404A to only partially restrict blood flow through occluder 102. In such a circumstance, the blood passing through occluder 102 flows in an antegrade direction (e.g., as depicted by flow arrow 470), and a portion of blood blocked by occluding surface 104 might flow in a retrograde direction (or at least a portion of the blood in the coronary sinus may flow in a retrograde direction through vessels branching off the coronary sinus), such as indicated by flow arrow 470A. Thus, flap 404A may be said to permit simultaneous antegrade and retrograde flow.

Figure 20:
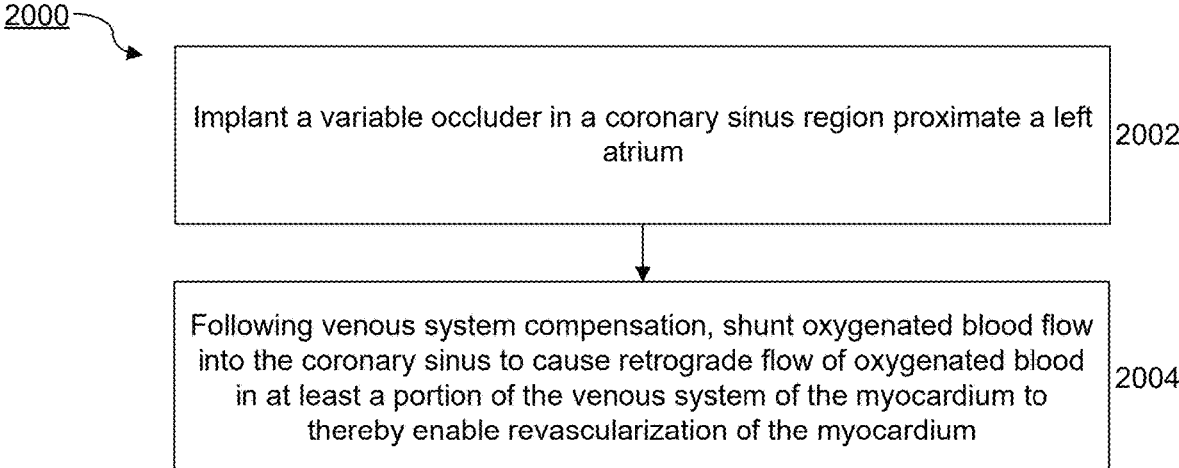
FIG. 20 is a flowchart of an example process for causing retrograde flow in at least a portion of a biological structure, consistent with some disclosed embodiments.

FIG. 20 illustrates a flowchart of a method 2000 for causing retrograde flow in at least a portion of a biological structure, consistent with some embodiments of the present disclosure. Method 2000 may include step 2002 of implanting a variable occluder in a coronary sinus region proximate a left atrium. Method 2000 may include step 2004 of, following venous system compensation, shunting oxygenated blood flow into the coronary sinus to cause retrograde flow of oxygenated blood in at least a portion of the venous system of the myocardium. For example, following venous system compensation, step 2004 may include shunting and flow directing oxygenated blood flow into the coronary sinus to cause retrograde flow of oxygenated blood in at least a portion of the venous system of the myocardium. The retrograde flow of oxygenated blood may enable revascularization of the myocardium.

Some disclosed embodiments may relate to a device for promoting venous system compensation to enable retrograde blood flow in at least a portion of the venous system of the myocardium. As used herein, enabling retrograde blood flow refers to permitting or facilitating a flow of blood in a retrograde direction in a cavity or blood vessel. Devices configured to enable retrograde blood flow are described throughout this disclosure and exemplified throughout the figures herein.

In some embodiments, a device may include a support. As used herein, a support refers to a component that provides stability, positioning, or reinforcement. For example, a support may have a tube-like structure and/or a scaffold structure, for positioning within a blood vessel. The support may be configured or used as an anchor or platform for a flow restrictor.

By way of non-limiting example, a support make take the form of stent 106, 806, 906, 1006, 1106, 1206, 1306, 1406, or 152 as illustrated throughout in the figures.

In some embodiments, a support may be configured for implantation within a coronary sinus at a location proximate a left atrium. Implantation refers to a medical procedure where something (here the support) is placed inside the body (here, a blood vessel). The support may be implanted in any manner that is medically suitable. By way of example only, the support may be transvascularly delivered to the coronary sinus at a location proximate a left atrium, as described earlier in connection with FIGS. 3A and 3B.

In some embodiments, the support may be adapted to transition between a compressed state for delivery within the coronary sinus and an expanded state for fixation within the coronary sinus. As used herein, adapted to transition between a compressed state and an expanded state refers to a characteristic of a device or component capable of changing from a collapsed configuration to an opened configuration due to or in response to one or more factors or causes. In one example, a support may be adapted to transition between a compressed state and an expanded state by, in the compressed state, being confined or contained within a tool, thereby having elastic potential energy such that, when the support is released or removed from the tool, the support uses elastic recoil to expand. Further by way of example, a support may be adapted to transition between a compressed state and an expanded state by being expandable, such as by a balloon. In another example, a support may be adapted to transition between a compressed state and an expanded state by being made of an expandable material, such as a shape memory alloy (e.g., nitinol) or biocompatible material configured to expand upon hydration by a fluid (e.g., polyvinyl alcohol hydrogel).

As used herein, fixation refers to a process or mechanism of securing something in place to prevent or limit movement. For example, fixation of a support within a structure may include the support exerting a radially outward force against the walls of the structure, thereby preventing movement or limiting migration within the structure. Further, fixation of a support within a blood vessel, such as a portion of the venous system of the myocardium (e.g., the coronary sinus), may include the support maintaining the fixation during activity of the blood vessel (e.g., antegrade blood flow, retrograde blood flow) by way of an anchor. An anchor refers to a component or device configured to secure another component or device in place and to prevent migration or displacement thereof. By way of non-limiting example, an anchor may include a flange, a rim, a barb, a hook, or any wall-embeddable sharp edge made of a biocompatible material.

In one non-limiting example, FIG. 3A depicts support 306A in a compressed state. In another non-limiting example, FIG. 3B depicts support 306A in a compressed state contained within tool 110 for delivering the compressed support 306A to a location for implantation. Further, FIG. 2 depicts tool 110 containing a support (e.g., stent 106) in a compressed state for delivery within a coronary sinus. Further by way of non-limiting example, FIGS. 1A and 1B depict a support (e.g., stent 106) in an expanded state for fixation within coronary sinus 130. As depicted in FIGS. 1A and 1B, stent 106 is fixed at a location in coronary sinus 130 proximate left atrium 120 by engaging with and exerting a radially outward force on the walls of coronary sinus 130.

In some embodiments, a support in an expanded state may include a passageway therethrough. A passageway refers to a channel or opening that allows a fluid, such as blood, to flow through. For example, a passageway of a support in an expanded state may include a channel or opening through which blood may flow. Further, a passageway of a support in an expanded state may include a channel or opening through which a tool, such as a catheter, may be inserted to pass through or along the length of the support.

By way of non-limiting example, FIGS. 1A and 1B depict a support (e.g., stent 106) in an expanded state with passageway 107 through which blood in coronary sinus 130 may flow. As depicted in FIG. 1B, passageway 107 may permit tool 110 to pass therethrough.

In some embodiments, a device may include a variable occluder associated with a support. As used herein, a variable occluder associated with a support refers to a device or component configured to adjust or vary a level or extent of occlusion (i.e., flow restriction). A variable occluder is "associated with" a support when it is connected to, attached to, part of, or engaged with the support. For example, a variable occluder may be affixed to a support via a mechanical connection (e.g., interlocked using tabs, grooves, fasteners, clamps), an adhesive (e.g., cyanoacrylate, epoxy, fibrin sealant, collagen-based adhesive), welding, heat sealing, suturing, a magnetic connection, encapsulation, coating, or any other suitable biocompatible means of connecting two components known to those skilled in the art.

By way of non-limiting example, FIG. 4A depicts a device 400 with variable occluder 102 associated with (e.g., connected to) a support (e.g., stent 106). Further, FIG. 8A depicts a device 800 with variable occluder 802 associated with (e.g., connected to) a support (e.g., stent 806). Other non-limiting examples of devices with a variable occluder associated with a support are depicted in FIGS. 9A through 14F, as further described and exemplified below.

In some embodiments, a variable occluder may be configured to gradually increase a level of antegrade blood flow restriction through a passageway over a period of days. As used herein, configured to gradually increase a level of blood flow restriction through a passageway refers to a characteristic of a device or component capable of slowly or incrementally increasing a level of occlusion of a passageway or through a passageway over time. For example, an occluding surface of a variable occluder may change or adjust a geometry to occupy or take up a larger surface area relative to a cross section of the structure in which the variable occluder is implanted. Additionally or alternatively, one or more variable openings or apertures may close over time to gradually increase a level of blood flow restriction.

In some examples, a variable occluder may be configured to gradually increase a level of blood flow restriction through a passageway as a function of pressure. For example, the variable occluder may be configured to at least partially allow blood flow passage through the passageway at a first flow volume when the pressure on the upstream side of the variable occluder is above 60 mmHg. The first flow volume may be a somewhat restricted volume when compared with the flow volume that would ordinarily pass in the absence of an occluder. Such a restriction will then cause a higher pressure on the upstream side of the occluder than would ordinarily be present. The higher pressure, in turn, will initially begin the process of venous system remodeling (e.g., in the venous system of the myocardium when the occluder is implanted in the coronary sinus). As the venous system begins to remodel, it will become capable of accepting a greater level of retrograde blood flow, which in turn will cause the pressure to drop in the coronary sinus. The occluder, which, in this example, may be pressure sensitive, will react by closing further (in response to the decrease in upstream pressure.) This incremental closure will then cause further increased pressure in the coronary sinus, causing further remodeling of the venous system, and a further pressure drop upstream of the pressure-responsive occluder. The cycle will continue with the occluder incrementally closing in response to the lower upstream pressures, until finally the venous system is sufficiently remodeled to be ready to accept retrograde oxygenated blood flow at the pressure in the range of the left atrium pressure. It may be the case that remodeling only becomes sufficient when the occluder is completely closed, permitting no passage of antegrade flow. In other instances, the occluder may not be completely closed at the time when the venous system is sufficiently remodeled. In such a circumstance, some amount of blood flow may continue to pass through the passageway of the occluder while significant retrograde flow occurs simultaneously in the venous vasculature branching off the coronary sinus.

The pressures at which the variable occluder begins and ends the process of venous system remodeling may vary according to the biology of the patient, or according to specific device design constraints. For example, venous system remodeling may begin when the occluder causes an upstream pressure in the coronary sinus of 60 mmHg or greater, and may end when the upstream pressure in the coronary sinus drops to 30 mmHg. Depending on design, at 30 mmHg, the occluder may substantially or completely block blood flow through the occluder passageway. In this example, the occluder is said to substantially restrict blood flow passage through the passageway to a second flow volume less than the first flow volume when the pressure on the upstream side of the variable occluder is below 30 mmHg and to allow a significantly higher level of blood flow passage through the passageway at a first flow volume when the pressure on the upstream side of the variable occluder is above 60 mmHg. Through trial and error, the materials and thicknesses of the components of the occluder can be selected by a skilled artisan, to conform with the desired opening and closing profile. Thus, the desired beginning and ending flow rates can be adjusted through choice of occluder materials, thicknesses, and structure. These choices may be made by the medical device designer, and therefore, the particular structures described herein are meant to be exemplary only.

Moreover, the skilled artisan has the ability to select the opening and closing endpoints as well as the profile of the intermediate positions. In some designs, it may be desired to set the upper and lower desired endpoints at 60 mmHg and 35 mmHg; 60 mmHg and 30 mmHg; 60 mmHg and 25 mmHg; 55 mmHg and 35 mmHg; 55 mmHg and 30 mmHg; 55 mmHg and 25 mmHg; 50 mmHg and 35 mmHg; 50 mmHg and 30 mmHg; 50 mmHg and 25 mmHg; 45 mmHg and 35 mmHg; 45 mmHg and 30 mmHg; 45 mmHg and 25 mmHg; 40 mmHg and 35 mmHg; 40 mmHg and 30 mmHg; 40 mmHg and 25 mmHg; or any other desired upper and lower endpoints. In general, it may be understood by one of ordinary skill in the art that the aforementioned pressure thresholds may apply to a subset of patients, and the pressure thresholds may be unique or tuned to each patient's body. Non-limiting examples of such a variable occluder are described and exemplified elsewhere herein.

While the variable occlusion is discussed in the preceding paragraphs as a function of pressure, the occluder might alternatively be designed to gradually occlude as a function of time. It may be known, for example, that after a certain number of elapsed days, weeks, or months, full myocardium vascular system remodeling will necessarily occur. Therefore, the occluder may be designed to gradually close over that time period. This may be accomplished though the mechanisms described earlier (i.e., degradation, dissolving, promoted tissue growth over the opening of the occluder, etc.) In some embodiments, a variable occluder may include at least one perforated sheet. A perforated sheet refers to a thin, flat, and flexible piece of material having at least one hole or opening therein. The opening may be, for example, between 0.5-5 mm. For example, a perforated sheet may include a single hole or a plurality of holes through which a fluid (e.g., blood) may flow. In some examples, a hole of the perforated sheet may have a diameter in the range of 0.5 mm to 0.8 mm or 1 mm to 3 mm. Further, a perforated sheet may be configured to be elastic or flexible. In some examples, a perforated sheet may be made of EPTFE, PET (Dacron), TPU, silicon, nylon, processed pericardium, or any other suitable material.

In some embodiments, a variable occluder may include at least one flap. As used herein, unless otherwise specified, a flap refers to a flexible or elastic component that is movable or hinged. For example, a flap may be connected or attached on one side to another component or structure and may be moved or pivoted on the other side. In another example, a flexible or elastic component may enable movement or pivot of the flap, dependent on a pressure applied to the flap. Alternatively, a flap may refer to a component that is associated with a flexible or elastic component, such as a flexible arm. A flap may transition from an open state to a closed state to gradually increase a level of blood flow restriction through a passageway provided by the flap in the open state.

In some embodiments, at least one flap may be movable and configured to move in a manner limiting blood flow through the passageway in response to changes in the pressure on the upstream side of the variable occluder. As used herein, movable refers to a capability of a component or device to change position. For example, a flap may be movable by being connected to a structure (e.g., a support, a flexible frame element) on one portion and not connected to the structure on another portion. In this way, the connected portion of the flap may act as a hinge. In some examples, a flap may be biased closed such that the flap may, in isolation, be in a closed state and, in response to (e.g., based on, caused by) a stimulus (e.g., pressure), may transition into an open state. By way of non-limiting example, when a pressure on an upstream side of the variable occluder (e.g., relative to the pressure on a downstream side) is above a threshold (e.g., between 30 and 60 mmHg, between 30 and 40 mmHg, between 40 and 50 mmHg, above 50 mmHg, above 40 mmHg), the pressure exerted by a fluid flowing and pushing against the flap may force the flap into an open state, thereby permitting a flow of fluid therethrough. Then, when a pressure on an upstream side of the variable occluder (relative to a pressure on a downstream side) is below a threshold (e.g., less than 30 mmHg, substantially 0 mmHg), the flap may relax into or return to a closed state, thereby substantially occluding the passageway. When exposed to pressures in between the upper and lower thresholds, the flap may assume various intermediate positions, depending on pressure (or pressure gradient across the flap). In some embodiments, a flap may be made of a same material as a perforated sheet. In other embodiments, a flap may be made of a material different from the perforated sheet.

In some embodiments, at least one flap is configured to progressively restrict antegrade blood flow through the passageway as antegrade blood flow force on the flap decreases. For example, at least one flap may be biased closed and oriented in a vessel (e.g., coronary sinus, any portion of the venous system of the myocardium, or any other part of the body) such that an antegrade blood flow above a threshold (e.g., above 30 mmHg, above 40 mmHg, above 50 mmHg, above 60 mmHg) may act on and force the at least one flap into an open state. Further, when the antegrade blood flow drops below a threshold (e.g., below 30 mmHg), the at least one flap may relax into or return to a closed state, thereby increasing a level of antegrade blood flow restriction.

By way of non-limiting example, FIG. 4A-4C depict device 400 with flap 404A in an open state (e.g., as opened by an upstream pressure greater than a threshold) and connected to fixed portion 404B on one side or one portion, thereby providing a passageway 407A through which fluid (e.g., blood) may flow. Fixed portion 404B may be configured not to move (e.g., as opposed to flap 404A) and provide a same level of blood flow restriction regardless of a position of flap 404A. Further, FIG. 5A-5C depict device 400 with flap 404A in a closed state (e.g., due to an upstream pressure being below a threshold) with no passageway therethrough, thereby having an increased level of blood flow restriction (e.g., full occlusion) compared to the open state.

In some embodiments, at least one flap may include at least one sheet of flexible material. As used herein, a sheet of flexible material refers to a layer or component that is capable of bending, stretching, or conforming to different shapes under particular expected operating conditions without permanently losing its shape. For example, a sheet of flexible material may include a layer made of a biocompatible polymer (e.g., polyurethane, silicone), EPTFE, PET (Dacron), silicon, nylon, processed pericardium, or any other suitable flexible biocompatible material.

By way of non-limiting example, FIGS. 8A and 8B depict device 800 with a flexible flap including made up of a flexible frame extending from support 806 and a flap sheet 804C as well as a static flap 804B. In the open state depicted in FIG. 8A, flap sheet 804C may provide passageway 807A through which fluid may flow (e.g., as indicated by flow arrow 870). For example, fluid may flow through passageway 807 and exert a force on flexible sheet flap 804C when the pressure gradient across variable occluder 802 is greater than a threshold. Further, when the pressure gradient across variable occluder 802 is below the threshold, the flexible flap including a flexible frame extending from support 806 and flap sheet 804C may relax or return to a closed state.

Additionally, in some embodiments, at least one sheet of flexible material may include a plurality of flexible sheets. As used herein, a plurality of flexible sheets refers to a two or more flexible sheets. For example, a plurality of flexible sheets may be stacked to provide increased strength or durability. In another example, a plurality of flexible sheets may include two flexible sheets each occupying or covering a different area.

By way of non-limiting example, FIGS. 9A and 9B depict device 900 with a variable occluder 902 having two flaps 904C made from a sheet of flexible material. In the open state depicted in FIG. 9A, both flaps 904C are flexed or extended outwards, creating passageway 907A therebetween through which fluid may flow (e.g., as indicated by flow arrow 970). The flaps 904C may be pushed or forced open when a pressure gradient across variable occluder 902 is above a threshold. Further, the flaps 904C may relax to a closed state when a pressure gradient across variable occluder 902 is below the threshold.

Further by way of non-limiting example, FIGS. 10A and 10B depict device 1000 with a variable occluder 1002 having two flaps 1004A. In the open state depicted in FIG. 10A, both flaps 1004 are pushed open (e.g., due to a pressure gradient exceeding a threshold), creating passageway 1007A through which fluid may flow (e.g., as indicated by flow arrow 1070). In the closed state depicted in FIG. 10B, both flaps 1004 are relaxed or returned to a closed state (e.g., due to a pressure gradient below a threshold), closing passageway 1007A and thereby having an increased level of flow restriction compared to the open state.

In some embodiments, a variable occluder may include a perforated sheet extending over an opening of the passageway and a flap configured to adhere to the opening to thereby seal the opening when the pressure on the upstream side of the variable occluder reaches the threshold. A sheet extending over an opening refers to the sheet covering the opening or at least a portion thereof. The opening in this context refers to the entry to a passageway or to a portion of a passageway. Sealing an opening refers to closing or covering that entry (e.g., a hole or gap in such a way that prevents or limits a fluid from passing therethrough). For example, sealing an opening may include substantially occluding the opening (e.g., flow decrease by 50%, 75%, 99%, 100% compared to normal or baseline). By way of non-limiting example, sealing an opening may include promoting tissue growth over the opening, as further described and exemplified below. In another non-limiting example, sealing an opening may include covering an opening with a flap. The occluder may be designed such that the sealing occurs only after the upstream pressure (effectively corresponding to a pressure gradient across the opening) reaches a threshold. That threshold will typically correspond to sufficient venous system remodeling.

As used herein, adhering to an opening to thereby seal the opening refers to the flap clinging or pressing up against the material forming the opening. This may occur without any adhesive, but rather as the result of pressure exerted by the blood on the flap, causing the flap to seal against an opposing surface. In addition or alternatively, an exerted pressure may cause a bonding to occur or other closure mechanisms such as magnetism may help hold the flap in a closed position. In some embodiments, adhering may include utilizing one or more magnetic elements. A magnetic element refers to a material, component, or device that can generate, interact with, or respond to a magnetic field. For example, a magnetic element may be made of or coated in a biocompatible magnetic material, such as superparamagnetic iron oxide nanoparticles (SPIONs), cobalt-chromium alloys, magnetite-polymer composites, or any other suitable biocompatible magnetic material known to those skilled in the art. In one example, a flap may include a magnetic element and a support or occluding surface may include another magnetic element such that when a pressure upstream the variable occluder is above a threshold (e.g., 30 mmHg, 40 mmHg, 50 mmHg, 60 mmHg), the magnetic force is overcome and the flap is opened and when the pressure upstream of the variable occluder is below the threshold, the magnetic force joins the magnetic elements and closes the flap, thereby sealing the opening.

Figures 12A, 12B:
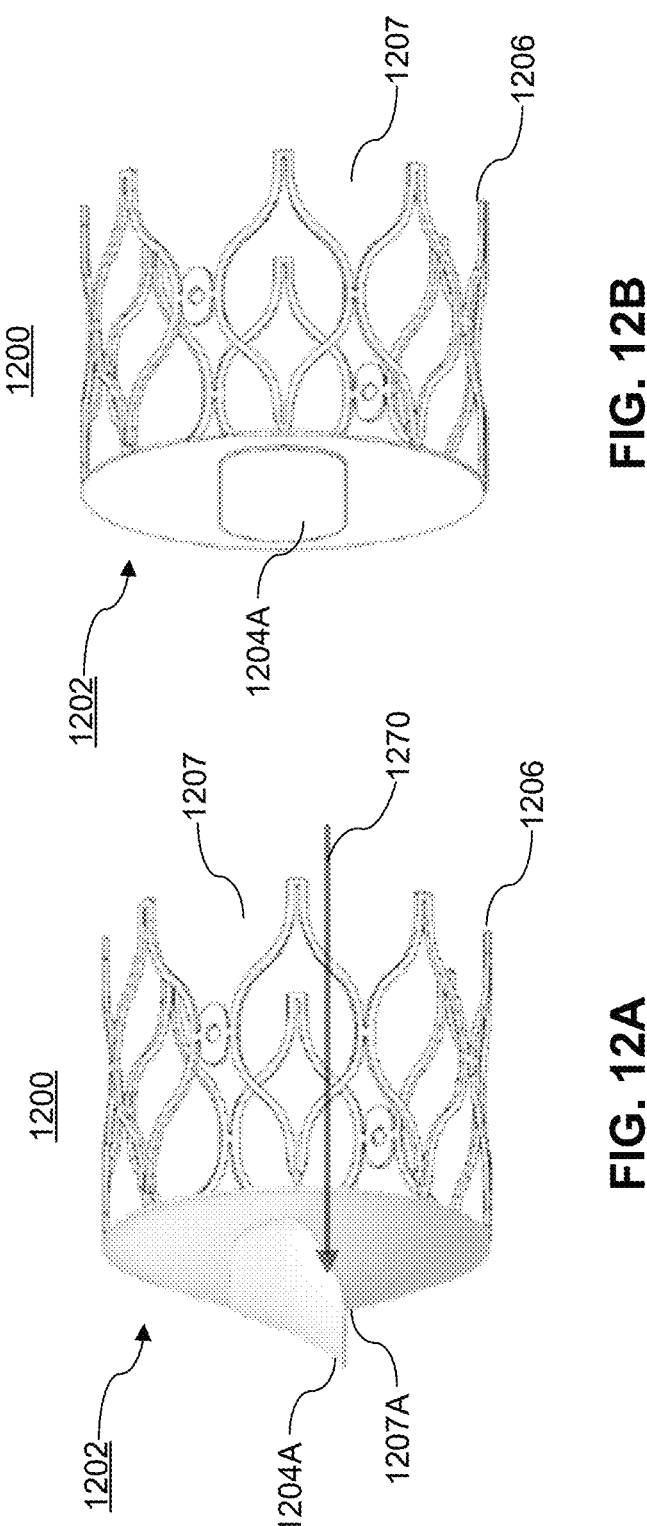
FIG. 12A is an isometric view of another example occluder in an open state, consistent with some disclosed embodiments.
FIG. 12B is an isometric view of the example occluder illustrated in FIG. 12A in a closed state, consistent with some disclosed embodiments.

By way non-limiting example, FIGS. 12A and 12B depict device 1200 with a variable occluder 1202 having a flap 1204A. As depicted in FIG. 12A, flap 1204A may be in an open state, providing a passageway 1207A through which fluid (e.g., blood) may flow (e.g., from or to passageway 1207, as indicated by flow arrow 1270). Further, as depicted in FIG. 12B, flap 1204A may be in a closed state, through which substantially no fluid may flow. Flap 1204A may extend from variable occluder 1202 and may be sized to cover passageway 1207A. Further, in some examples, flap 1204A and variable occluder 1202 may each include a magnetic component such that when flap 1204A is in a closed state, the magnetic components may magnetically connect to each other, thereby adhering flap 1204A to seal passageway 1207A, and preventing a flow of fluid therethrough.

Figures 13A, 13B, 13C, 13D:
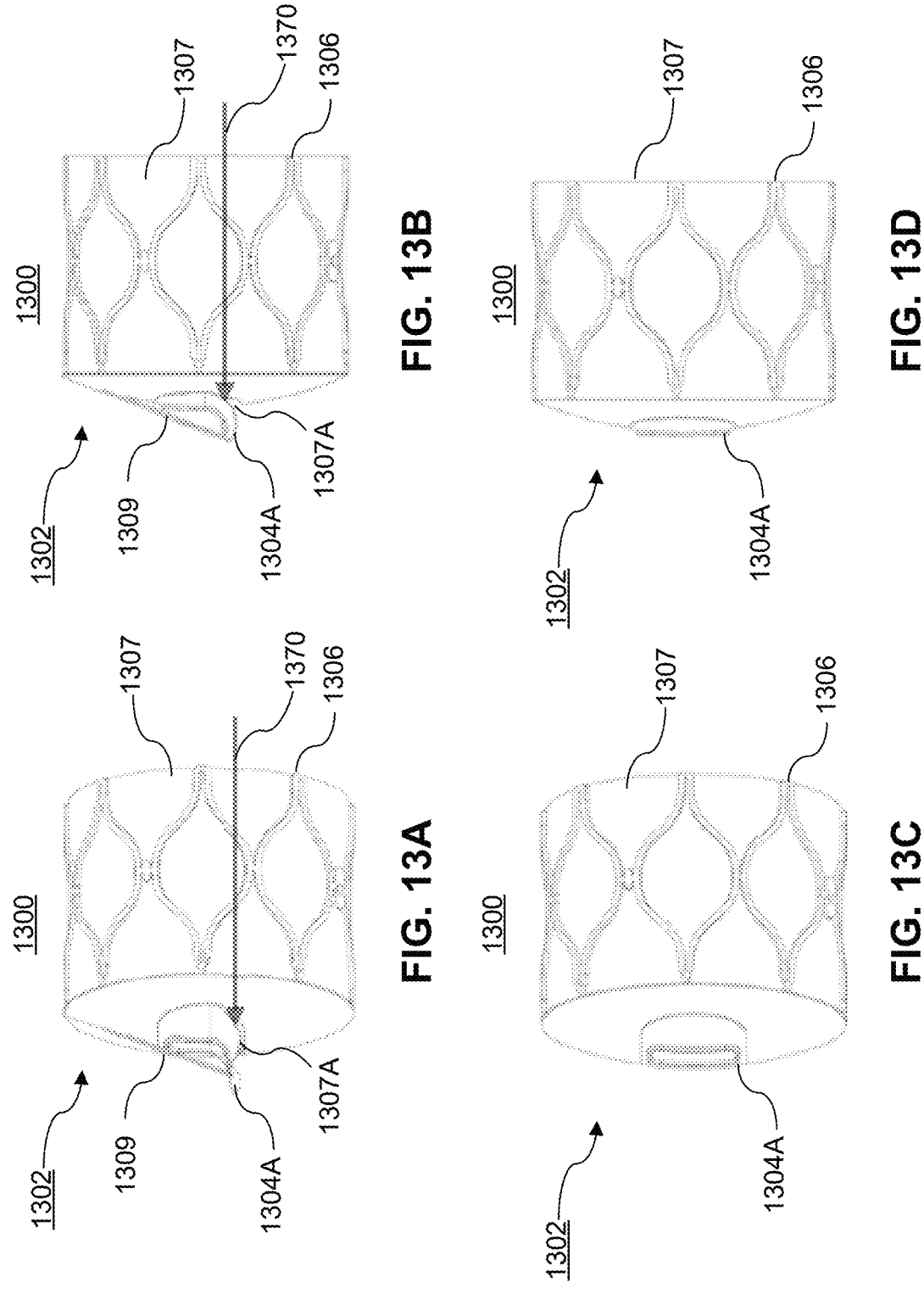
FIG. 13A is an isometric view of another example occluder in an open state, consistent with some disclosed embodiments.
FIG. 13B is a side view of the example occluder illustrated in FIG. 13A.
FIG. 13C is an isometric view of the example occluder illustrated in FIG. 13A in a closed state, consistent with some disclosed embodiments.
FIG. 13D is a side view of the example occluder illustrated in FIG. 13C.

By way of another non-limiting example, FIG. 13A-13C depict device 1300 with a variable occluder 1302 having a flap 1304A and a condition-dependent connection 1309. Flap 1304A may further include flexible frame to reduce flexibility. Condition-dependent connection 1309 may be connected to flap 1304A to keep flap 1304A in an open state, thereby permitting a flow of fluid therethrough (e.g., as indicated by flow arrow 1370). Further, condition-dependent connection 1309 may be made of a biodegradable material, as described and exemplified elsewhere herein, such that condition-dependent connection 1309 may naturally degrade over time or manually, mechanically or magnetically disconnect by internal or external action by a user. Once condition-dependent connection 1309 is degraded, flap 1304A may transition from the open state depicted in FIGS. 13A and 13B to the closed state depicted in 13C and 13D. In the closed state, flap 1304A may adhere to passageway 1307A (e.g., magnetic connection, adhesive connection, mechanical connection, or simply based on blood pressure), thereby sealing passageway 1307A and preventing a flow of fluid therethrough.

In some embodiments, a variable occluder may include material configured to promote tissue growth and thereby inhibit blood flow through the passageway. As used herein, promoting tissue growth refers to a material that stimulates, supports, or accelerates the development of tissue thereupon. For example, one side of a perforated sheet of a variable occluder may be coated with a delay tissue formation material (e.g., EPTFE), and the other side may be coated with a material that promotes tissue formation (e.g., PET). In this way, as tissue grows on the other side, the growing tissue may cover one or more holes of the perforated sheet, thereby increasing a level of blood flow restriction therethrough.

By way of non-limiting example, FIGS. 11A and 11B depict device 1100 with perforated sheet 1104D having a number of slits 1107B. Perforated sheet 1104D may be configured to promote tissue growth (e.g., by being made of PET) such that, over time, slits 1107B gradually transition from an open state permitting a flow of fluid therethrough (e.g., as depicted in FIG. 11A and indicated by flow arrows 1170) to a closed state not permitting any flow of fluid therethrough (e.g., as depicted in FIG. 11B). Slits 1107B may have a length less than a diameter of perforated sheet 1104D. For example, slits 1107B may have a length less than 70%, less than 50%, less than 40%, less than 30%, or less than 20% of the diameter of perforated sheet 1104D. Alternatively, perforated sheet 1104D may be made of a stretchable material such that as pressure is exerted on the material, the slits open to allow fluid to pass, and as the pressure drops the slits close as they are no longer deformed by the pressure.

In some embodiments, a variable occluder may include a flexible frame element. A flexible frame element refers to a component that is capable of deforming or bending. For example, a flexible frame element may be configured to maintain a first, rigid state while experiencing a force or pressure below a threshold and to bend or flex to a second, bent state while experiencing a force or pressure above a threshold. Additionally or alternatively, a flexible frame element may be configured to longitudinally expand while experiencing a force or pressure below a threshold and to be compressed to a second, compressed state while experiencing a force or pressure above a threshold.

In some examples, a flexible frame element may be connected to a component (e.g., a support, a perforated sheet, a flat sheet, a flap and/or a variable occluder) at one or more points. For example, a flexible frame may be connected to another component via welding, sewing, gluing, or any other mechanical or chemical means of securely connecting two components. Alternatively, the components need not be bonded, but rather the force of the flexible frame element presses against an associated component. Further, a flexible frame may be connected to another component securely and suitably for one or more fatigue requirements in relation to a support and/or in relation to a perforated sheet. A fatigue requirement may include a design criterion that ensures a component or device can withstand repeated loading and unloading over an expected lifespan without experiencing failure due to fatigue.

In some examples, a flexible frame element may be configured to apply a pressure or force against at least one flap of a variable occluder to keep the at least one flap in a closed state below a threshold (e.g., 30 mmHg, 0 mmHg) and to bend and permit the at least one flap to transition to an open state above a threshold (e.g., 30 mmHg, 40 mmHg, 50 mmHg, 60 mmHg). In another example, a flexible frame element may be configured to apply a pressure or force against a perforated sheet. Further, a flexible frame may be controlled to transition the at least one flap or transition the at least one opening in a perforated sheet between an open and a closed state based on the mechanical properties of the flexible frame and/or the geometric design of the flexible frame. For example, based on the material from which the flexible frame is made (e.g., nitinol, stainless steel, cobalt-chrome, or any other similar or similarly suitable material) and/or a geometric design of the flexible frame (e.g., as described and exemplified below), the threshold at which point the flexible frame opens or closes the at least one flap may be adjusted. In some examples, a flexible frame may be configured to control at least one flap independent of changes in size to the structure in which the variable occluder is implanted. By way of non-limiting example, as a vessel (e.g., coronary sinus) constricts and relaxes in normal function, the flexible frame may control the at least one flap only in response to changes in a pressure gradient (e.g., difference between upstream pressure and downstream pressure) relative to the variable occluder.

In some examples, a flexible frame element may be shaped as a spring (e.g., coil or helix), associated with a flat sheet and configured to apply a pressure or force against at least one perforated sheet to reduce the flow through the perforated sheet below a threshold (e.g., 30 mmHg, 0 mmHg) and to longitudinally compress the coil-shaped flexible frame and permit blood flow above a threshold (e.g., 30 mmHg, 40 mmHg, 50 mmHg, 60 mmHg). Based on the material from which the flexible frame and the flat sheet is made, and a geometric design of the flexible frame, the threshold at which point the flexible frame opens or closes the opening in the perforated sheet may be adjusted.

In some examples, a flexible frame may have any shape such that a distance between any two points along a perimeter of the flexible frame is less than a diameter of a vein (e.g., 7-13 mm) in a constricted state. For example, a flexible frame may be shaped as a zigzag, a curve, or a polygon. In some embodiments, the flexible frame is sized such that the distance between any point on the perimeter of the flexible frame and the support frame or coronary sinus is more than 1 mm, 2 mm, 3 mm, or 5 mm.

In some examples, a flexible frame may be integrally formed with a support. For example, a flexible frame and a support may be formed from a same tube, and the flexible frame may be cut or bent from a support. In some examples a flexible frame may be integrally formed with, associated with, or extended from a perforated sheet.

By way of non-limiting example, FIG. 4A-4C depict a flexible frame 405 bending and permitting flap 404A to be in an open state due to a pressure upstream of variable occluder 102 (e.g., relative to a downstream pressure as a pressure gradient) being above a threshold (e.g., 30 mmHg, 40 mmHg, 50 mmHg, 60 mmHg). Further, FIG. 5A-5C depict a flexible frame 405 in a more rigid state, preventing flap 404A from opening due to a pressure upstream of variable occluder 102 being below a threshold (e.g., 30 mmHg). By way of another non-limiting example, FIG. 4A-4C depict a flexible frame 405 bending and permitting flap 404A to be in an open state due to a pressure upstream of variable occluder 102 (e.g., relative to a downstream pressure as a pressure gradient) being above a threshold (e.g., 30 mmHg, 40 mmHg, 50 mmHg, 60 mmHg).

In some embodiments, a variable occluder may be configured to be permanently disabled after the period of days to enable retrograde flow in the coronary sinus. As used herein, permanently disabled refers to being irreversibly rendered inoperable so as to no longer function as intended (here, unable to effectively function as an occluder). For example, in some embodiments, a variable occluder may be configured to be permanently disabled by a tool configured to cross the variable occluder. As used herein, crossing refers to moving from one side of a boundary, surface, plane, or dividing line to another side. For example, in some embodiments, crossing may occur through penetration of a thin surface of material, while in other embodiments crossing may occur by passing a tool through a thicker piece of material, such as a plug or other seal. In one example, a tool may puncture and cross an occluding surface (e.g., perforated sheet, at least one flap) of a variable occluder, thereby creating an opening in the occluding surface through which fluid may flow. In this way, the variable occluder can no longer restrict a flow of fluid therethrough. In some examples, a permanently disabled variable occluder may permit a flow of fluid in the vessel (e.g., coronary sinus) therethrough that is substantially similar (e.g., within 10%, within 5%, within 1%) to a flow of fluid in the vessel (e.g., coronary sinus) without the variable occluder.

By way of non-limiting example, FIG. 1B depicts tool 110 crossing occluding surface 104 of variable occluder 102. By crossing the variable occluder, tool 110 forms an opening in occluding surface 104, thereby permanently (e.g., irreversibly) disabling variable occluder 102 and permitting a level of antegrade deoxygenated blood flow therethrough (e.g., as indicated by flow arrow 170).

In some embodiments, a flexible frame element may include a discontinuous perimeter configured to allow a tool to cross through the variable occluder. As used herein, a discontinuous perimeter refers to a boundary or outer edge of a shape that has a break, gap, or interruption. For example, a flexible frame element with a discontinuous perimeter may include a flexible frame having a gap between two ends of the flexible frame. In some examples, a flexible frame may be disconnectable. For example, a flexible frame may initially have a continuous perimeter and may, in response to a stimulus or cause (e.g., being disconnected or opened by a crossing and/or expandable tool), become discontinuous. Further, the flexible frame may be configured to be crossed by a tool such that when the tool crosses though the flexible frame, a gap in the discontinuous perimeter increases in size, permitting the tool to cross through the flexible frame. By way of non-limiting example, the flexible frame may be configured to accommodate a crossing tool with a diameter of up to 3 mm, 4 mm, 5 mm, 6 mm, or 7 mm. Further, in some examples, a flexible frame may include a biodegradable portion. The biodegradable portion may degrade over time, thereby creating an opening in the perimeter of the flexible frame.

By way of non-limiting example, FIGS. 6A and 6B depict flexible frame 405 with a discontinuous portion 605A. FIGS. 6C and 6D depict an expanded view of discontinuous portion 605, showing a gap 605D between two ends 605B and 605C. Therefore, flexible frame 405 as depicted in FIG. 6A-6D has a discontinuous perimeter. As a tool (e.g., tool 110) crosses through the center of flexible frame 405, gap 605D may increase in size to accommodate the diameter of the crossing tool.

In some embodiments, a flexible frame may be configured to be permanently disabled. For example, a flexible frame may be disabled by being compressed by an expandable element (e.g., balloon, stent frame, or any other dilator device). Further, the flexible frame may be pressed against a wall of a vessel (e.g., coronary sinus).

By way of non-limiting example, FIG. 7A-7C depict flexible frame 405 in a disabled state. As depicted in FIG. 7A-7C, flexible frame 405 in a disabled state occupies a plane tangential to the outer surface of stent 106. In the disabled state, flexible frame 405 no longer contacts or controls flap 404A, and flap 404A may open in response to an upstream pressure lower than a threshold (e.g., 30 mmHg, 40 mmHg, 50 mmHg, 60 mmHg).

In some embodiments, a spring may be associated with the flexible frame. A spring refers to a component or device that stores and releases energy when subjected to a force by deforming under load and returning to an original or resting shape when the force is removed. The spring may be integral with the flexible frame or may be a separate component mount on or otherwise connected to the flexible frame. For example, a spring may be positioned on a downstream side of a variable occluder to provide an elastic force or a restoring force against an occluding surface of the variable occluder (e.g., a flap, a flat sheet), thereby biasing the variable occluder closed. By way of non-limiting example, when a pressure on an upstream side of a variable occluder is above a threshold (e.g., 30 mmHg, 40 mmHg, 50 mmHg, 60 mmHg), the spring may compress, thereby permitting an occluding surface to transition to an open state, and permitting a flow of fluid therethrough. Further, when a pressure on an upstream side of a variable occluder is below a threshold (e.g., 30 mmHg, 40 mmHg, 50 mmHg, 60 mmHg), the spring may relax or return to an original or resting shape, thereby transitioning an occluding surface to a closed state in which substantially no fluid flows therethrough. A spring may be made of nitinol, stainless steel, cobalt-chromium alloys, titanium alloys, polyether ether ketone (PEEK), or any other suitable and biocompatible material known to those skilled in the art.

In embodiments employing a spring, a support may include at least one support post that extends on a downstream side of the variable occluder. The support post(s) may be integrally formed with the support and may be formed of the same material as the support. The support post(s) may provide a structural component to which a spring may be affixed, retained, or connected via a mechanical connection (e.g., interlocked using tabs, grooves, fasteners, clamps), an adhesive (e.g., cyanoacrylate, epoxy, fibrin sealant, collagen-based adhesive), welding, heat sealing, suturing, a magnetic connection, encapsulation, coating, or any other suitable biocompatible means of connecting two components known to those skilled in the art.

Figures 15A, 15B, 15C, 15D:
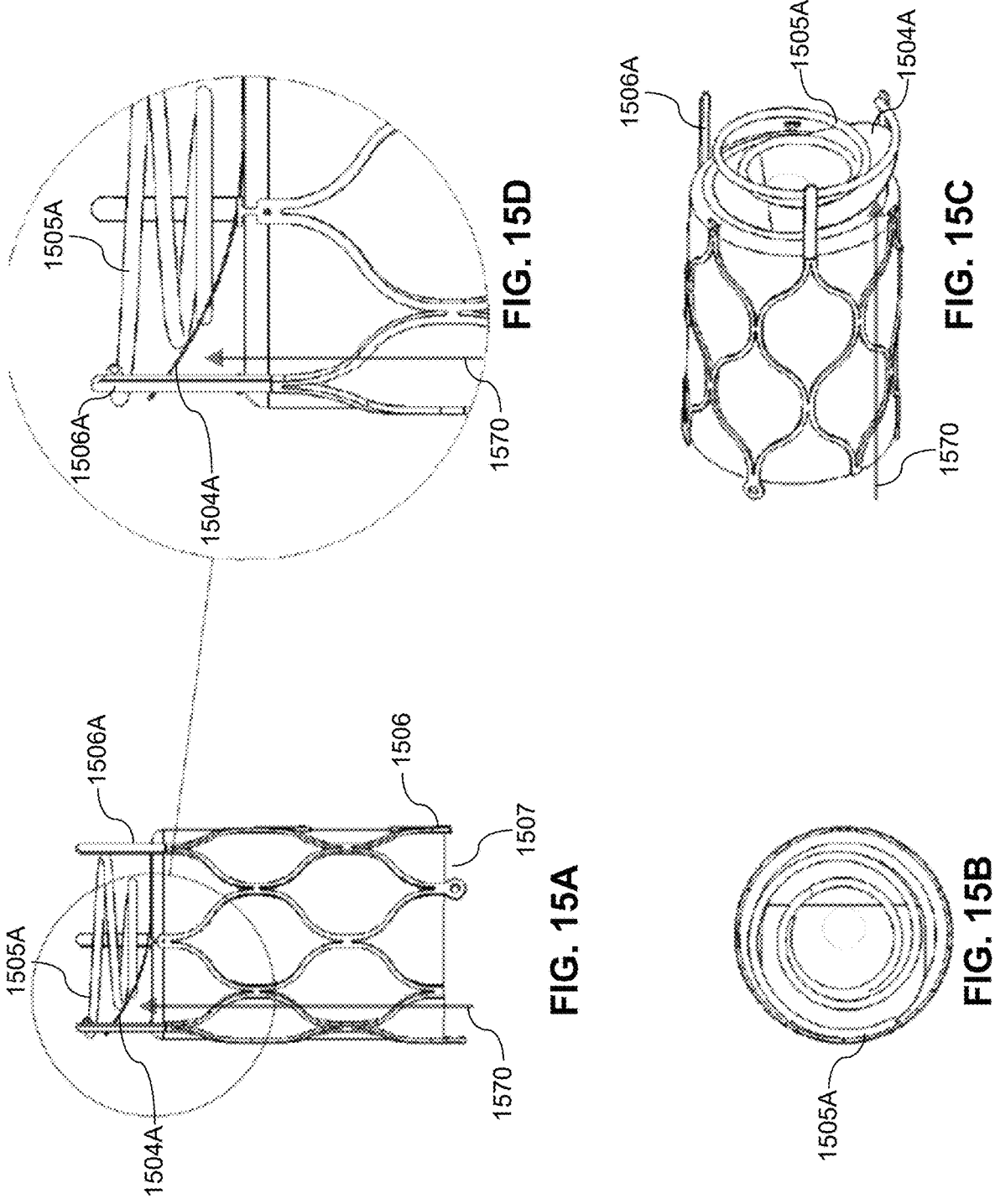
FIG. 15A is a side view of an example of a spring-biased occluder with a spring in an open state, consistent with some disclosed embodiments.
FIG. 15B is a top view of the example occluder illustrated in FIG. 15A.
FIG. 15C is an isometric view of the example occluder illustrated in FIG. 15A.
FIG. 15D is a detail view of a portion of the spring encircled in FIG. 15A.
Figures 15E, 15F, 15G, 15H:
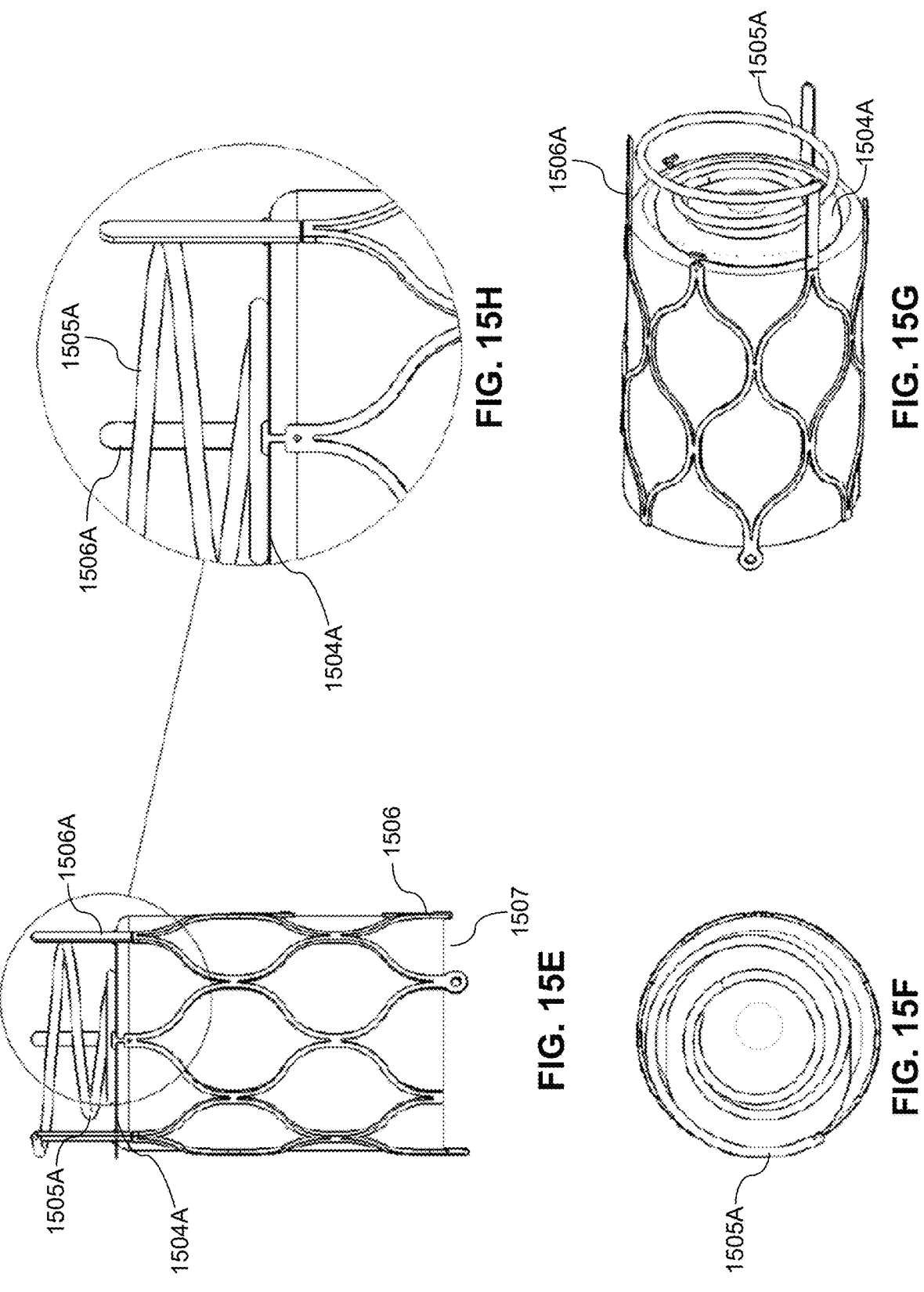
FIG. 15E is a side view of the example occluder illustrated in FIG. 15A in a closed state, consistent with some disclosed embodiments.
FIG. 15F is a top view of the example occluder illustrated in FIG. 15E.
FIG. 15G is an isometric view of the example occluder illustrated in FIG. 15E.
FIG. 15H is a detail view of the portion of the spring encircled in FIG. 15E.

By way of non-limiting example, FIG. 15A-15C depict an example device 1500 with a spring 1505A and flap 1504A in an open state. An upstream pressure exerted by fluid flowing through passageway 1507 (e.g., as indicated by flow arrow 1570) is above a threshold (e.g., 30 mmHg, 40 mmHg, 50 mmHg, 60 mmHg) compresses spring 1505A, thereby permitting flap 1504A to open and permit the fluid to flow therethrough. Device 1500 includes support 1506 with support posts 1506A, to which spring 1505A is connected and/or retained. FIG. 15E-15G depict device 1500 with spring 1505A and flap 1504A in a closed state.

Figures 16A, 16B, 16C, 16D:
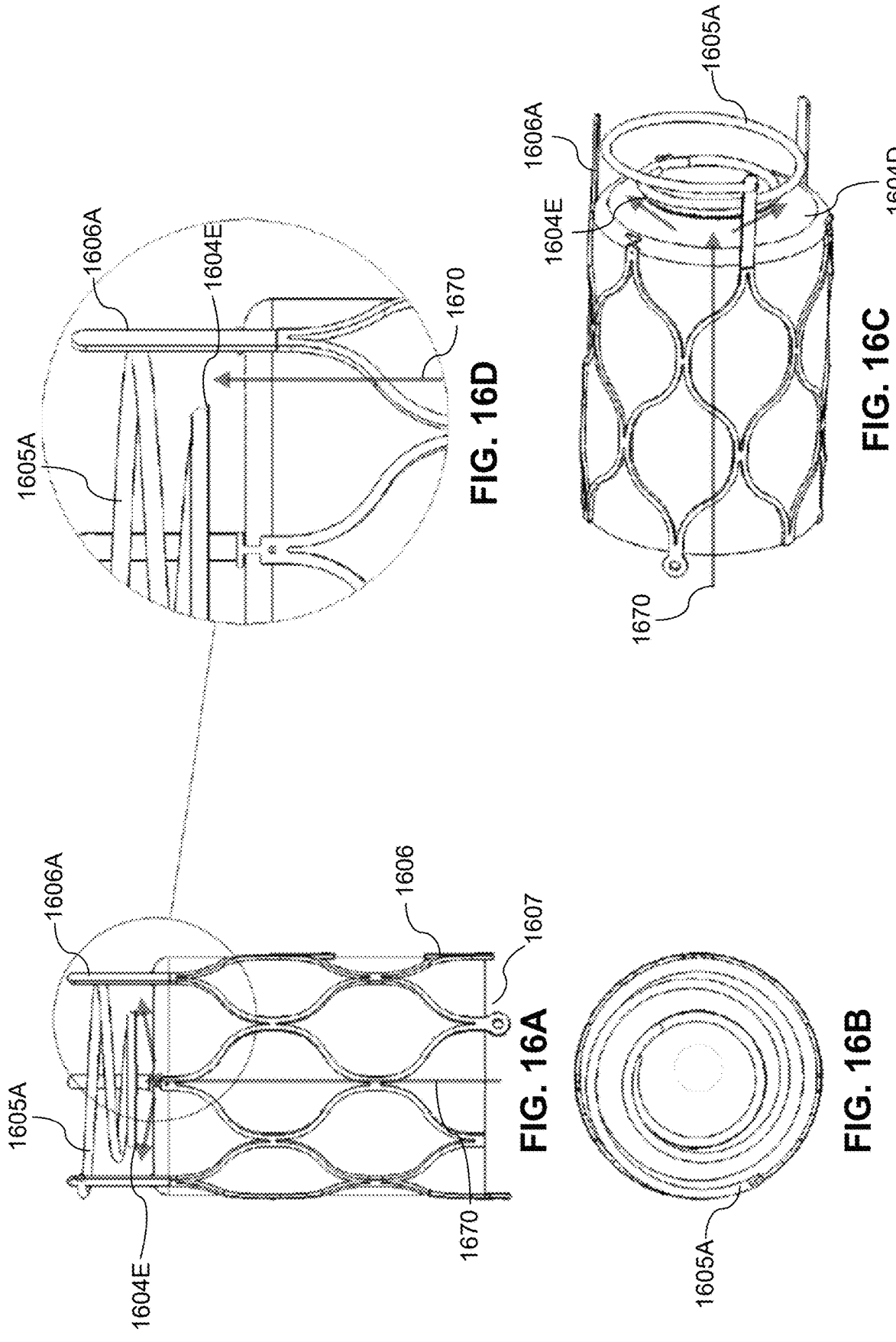
FIG. 16A is a side view of another example of a spring-biased occluder with a spring in an open state, consistent with some disclosed embodiments.
FIG. 16B is a top view of the example occluder illustrated in FIG. 16A.
FIG. 16C is an isometric view of the example occluder illustrated in FIG. 16A.
FIG. 16D is a detail view of the portion of the spring encircled illustrated in FIG. 16A.
Figures 16E, 16F, 16G, 16H:
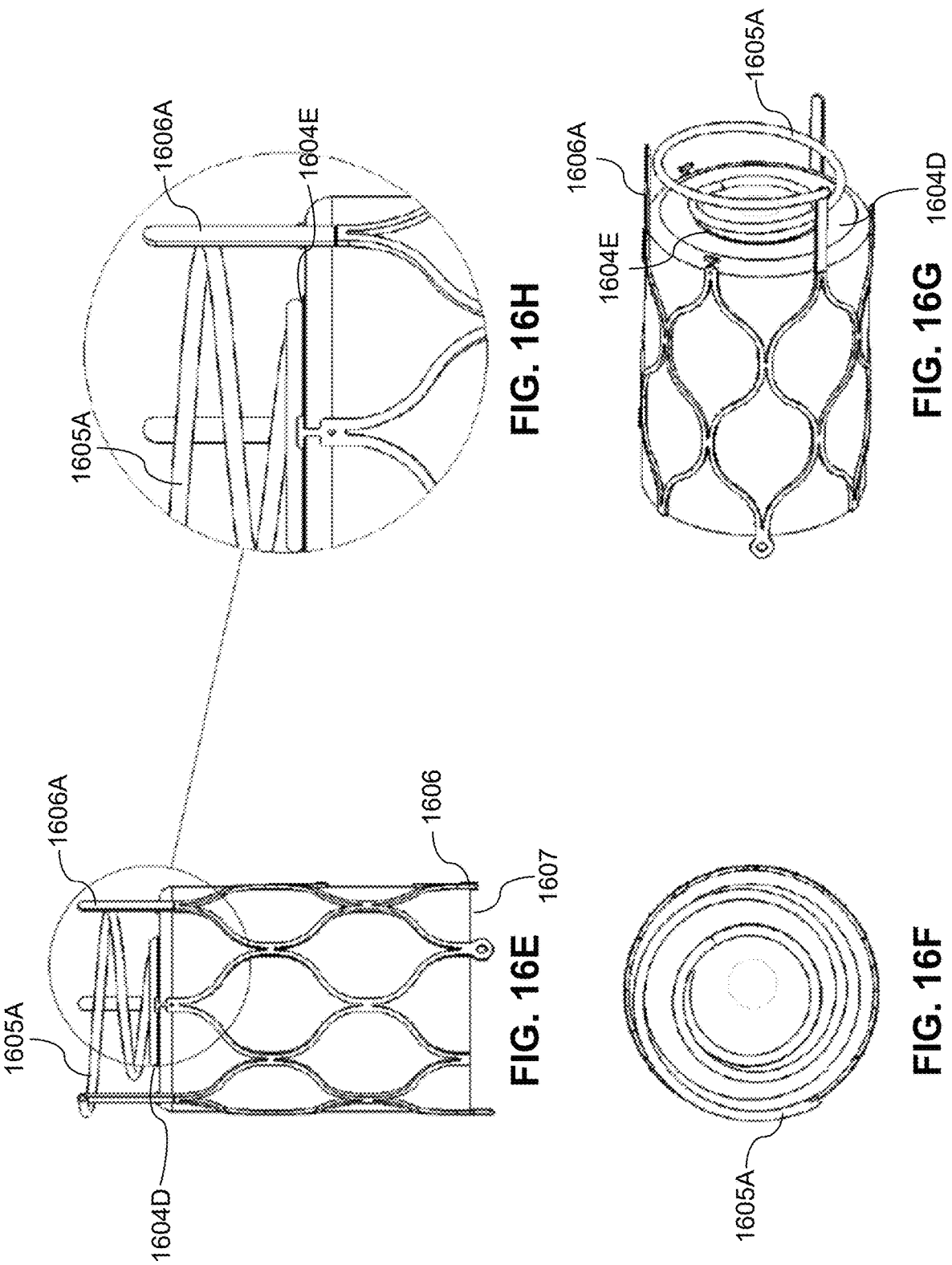
FIG. 16E is a side view of the example occluder illustrated in FIG. 16A in a closed state, consistent with some disclosed embodiments.
FIG. 16F is a top view of the example occluder illustrated in FIG. 16E.
FIG. 16G is an isometric view of the example occluder illustrated in FIG. 16E.
FIG. 16H is a detail view of a portion of the spring encircled in FIG. 16E.

Further by way of non-limiting example, FIG. 16A-16C depict an example device 1600 with a spring 1605A, perforated sheet 1604D, and flat sheet 1604E. As depicted in FIG. 16A-16C, spring 1605A and flat sheet 1604E may be connected to spring 1605A such that when an upstream pressure exerted by fluid flowing through passageway 1607 (e.g., as indicated by flow arrow 1670) is above a threshold (e.g., 30 mmHg, 40 mmHg, 50 mmHg, 60 mmHg) compresses spring 1505A, flat sheet 1604E is also moved with the compressed spring 1605A, thereby permitting the fluid to flow through an opening in perforated sheet 1604D. Device 1600 includes support 1606 with support posts 1606A, to which spring 1605A is connected. FIG. 16E-16G depict device 1600 in a closed state. In a closed state, flat sheet 160E may, as held by spring 1605A, cover an opening in perforated sheet 1604D, thereby permitting substantially no flow therethrough.

In some embodiments, gradually increasing a level of antegrade blood flow restriction through a passageway over a period of days may enable at least a portion of the venous system of the myocardium to compensate for increased pressure caused by the gradual increase in the level of antegrade blood flow restriction. In some embodiments, a period of days may span weeks. In some embodiments, a period of days may span months. In some embodiments, a period of days may span years. For example, by gradually increasing a level of antegrade blood flow restriction through a variable occluder, venous system compensation may occur, as described and exemplified elsewhere herein.

In some embodiments, a variable occluder may be further configured to substantially occlude antegrade blood flow through the passageway when a pressure on an upstream side of the variable occluder reaches a threshold of between 30 and 60 mmHg. Substantially occluding refers to being largely obstructed, such that the vast majority of the blood flow is rerouted in a retrograde manner. In some embodiments, substantial occlusion may be almost complete or complete occlusion (e.g., with less than 5% of normal blood passage). In some embodiments, a pressure threshold triggering substantial occlusion may be between 30 mmHg and 40 mmHg. In some embodiments, a threshold may be between 40 mmHg and 50 mmHg. In general, it may be appreciated by one having ordinary skill in the art that the upstream pressure threshold may depend on and vary with an anatomy of a patient.

As described in greater detail earlier, a variable occluder may be configured to cause retrograde flow in at least a portion of the venous system of the myocardium on an upstream side of the variable occlude When pressure reaches a threshold of between 30 and 60 mmHg, a variable occluder may be configured to cause retrograde flow in the at least a portion of the venous system of the myocardium on an upstream side of the variable occluder. That is, when the pressure reaches a design threshold on the upstream side of the occluder (or said another way, when the pressure gradient across the occluder reaches a threshold) retrograde flow occurs in at least some of the branches off of the coronary sinus.

In some embodiments, a support (as generally described earlier) may include a first section having a first diameter, and a second section having a second diameter greater than the first diameter. For example, the first section and the second section of the support may be integrally formed from a same tube. By way of non-limiting example, the first diameter may be less than 14 mm, less than 10 mm, or less than 8 mm; the second diameter may be more than 8 mm, more than 10 mm, more than 12 mm, or more than 14 mm. Further, the first section and the second section may be connected to form the support. By way of non-limiting example, the first section and the second section may be connected by at least one spring, at least one wire, at least one fabric, welding, or any other suitable connection method. Further, the first section and the second section may be connected by a frame coupler. A frame coupler may include a mechanical component configured to join or connect two or more sections together. For example, a frame coupler may have a linear shape, a curved shaped, or a coiled shape. Further, a frame coupler may include a fabric-based connection. A fabric-based connection may include medical-grade polyester, silk, polyurethane, PTFE, or medical-grade nylon.

In some embodiments, the second section may include fixation element to hinder migration. For example, a fixation element may include an anchor, as described and exemplified elsewhere herein. In an alternative or additional embodiment, the second diameter is sized to hinder migration of the support in the coronary sinus, and the first diameter is configured to support the variable occluder. As used herein, hinder migration refers to preventing, impeding, or restraining movement. For example, the second diameter may be sized to hinder migration by having a second diameter substantially similar to a diameter of a structure (e.g., coronary sinus), thereby engaging the walls of the structure and utilizing friction to prevent movement. The second diameter may be made to expand to a size a few millimeters wider than the coronary sinus diameter, such that when expanded, the second diameter exerts a friction and/or compression force on the coronary sinus wall. In contrast, the first diameter, may be a few millimeters smaller than the diameter of the coronary sinus. As the first diameter is designed to support the occluder, by making the first diameter smaller than the diameter of the coronary sinus, the first diameter stands off from the coronary sinus wall, preventing engagement with the wall from interfering with operation of the occluder.

Figures 14A, 14B, 14C, 14D, 14E, 14F:
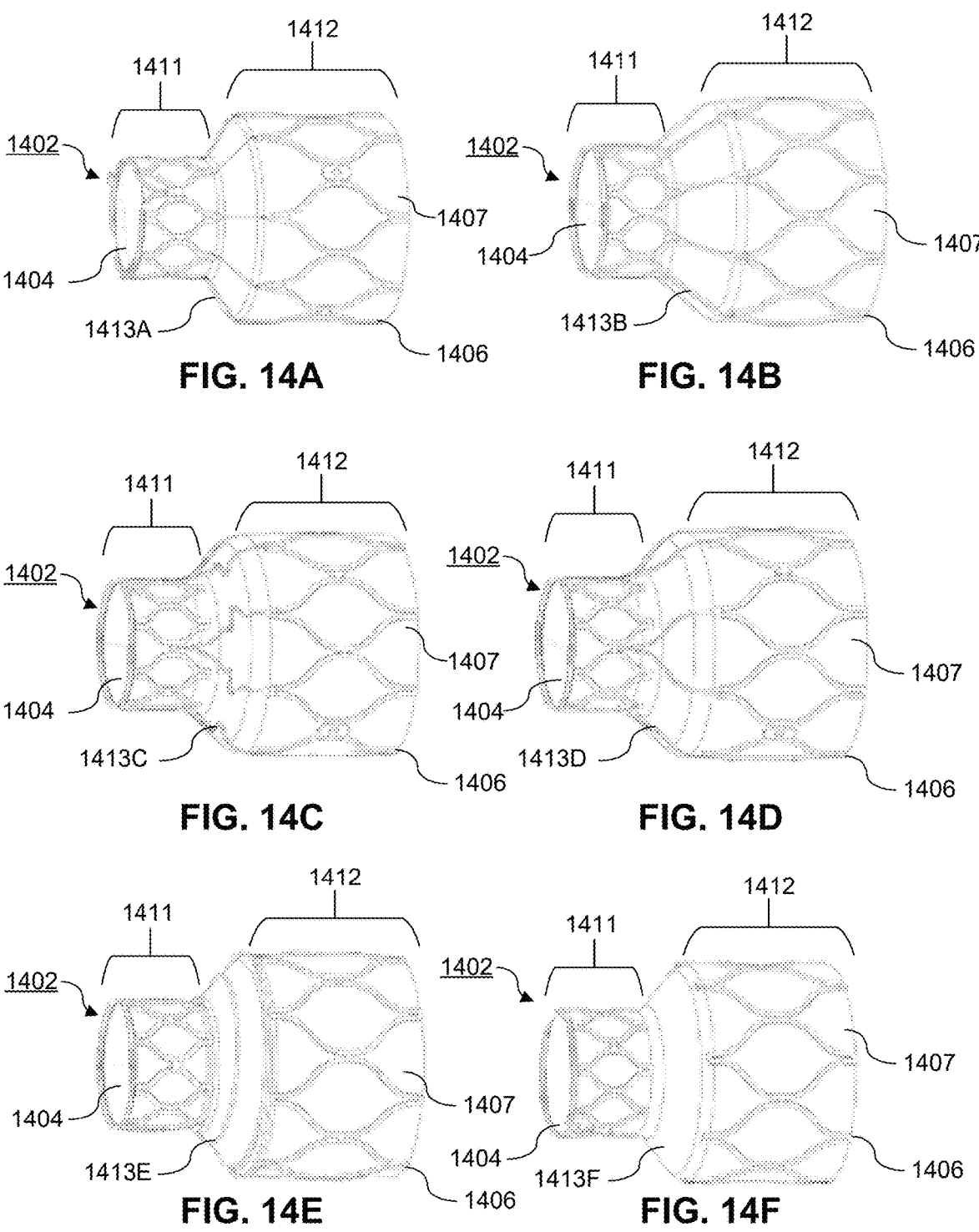
FIG. 14A is an isometric view of an example binary occluder, consistent with some disclosed embodiments.
FIG. 14B is an isometric view of another example binary occluder, consistent with some disclosed embodiments.
FIG. 14C is an isometric view of another example binary occluder, consistent with some disclosed embodiments.
FIG. 14D is an isometric view of another example binary occluder, consistent with some disclosed embodiments.
FIG. 14E is an isometric view of another example binary occluder, consistent with some disclosed embodiments.
FIG. 14F is an isometric view of another example binary occluder, consistent with some disclosed embodiments.

By way of non-limiting example, FIG. 14A-14F each depict support 1406 (e.g., a stent) with first section 1411 and second section 1412. As depicted in FIG. 14A, first section 1411 and second section 1412 are connected by linear frame coupler 1413A. As depicted in FIG. 14B, first section 1411 and second section 1412 are connected by linear frame coupler 1413B. As depicted in FIG. 14C, first section 1411 and second section 1412 are connected by curved frame coupler 1413C. As depicted in FIG. 14D, first section 1411 and second section 1412 are connected by curved frame coupler 1413D. As depicted in FIG. 14E, first section 1411 and second section 1412 are connected by coiled frame coupler 1413E. As depicted in FIG. 14F, first section 1411 and second section 1412 are connected by fabric-based connection 1413F. Further, as depicted in FIG. 14A-14F, variable occluder 1402 is secured and located within the first section.

Also disclosed herein are the following clauses:

Clause 1. A method for causing retrograde oxygenated blood flow in at least a portion of the venous system of the myocardium, the method comprising:

implanting a variable occluder in a coronary sinus region proximate a left atrium, wherein the variable occluder is configured to gradually increase a level of blood flow restriction over a period of days to enable a venous system of the myocardium to compensate for increased pressure caused by the gradual increase in the level of blood flow restriction; and following venous system compensation, shunting oxygenated blood flow into the coronary sinus to cause retrograde flow of oxygenated blood in at least a portion of the venous system of the myocardium to thereby enable revascularization of the myocardium.

Clause 2. The method of clause 1, wherein shunting oxygenated blood flow into the coronary sinus is from the left atrium.

Clause 3. The method of clause 1 or 2, wherein the variable occluder is configured for transvascular delivery in a compressed state for implantation in the coronary sinus via expansion in the region of the left atrium.

Clause 4. The method of any one of clauses 1-3, wherein the variable occluder is configured such that the gradual increase in the level of blood flow restriction occurs over a period of weeks.

Clause 5. The method of any one of clauses 1-4, wherein the variable occluder is configured such that the gradual increase in the level of blood flow restriction occurs over a period of months.

Clause 6. The method of any one of clauses 1-5, wherein the variable occluder is configured to gradually increase the level of blood flow restriction as a function of time.

Clause 7. The method of any one of clauses 1-6, wherein the variable occluder is configured to gradually increase the level of blood flow restriction as a function of pressure.

Clause 8. The method of any one of clauses 1-7, wherein the variable occluder is configured such that the level of blood flow restriction increases as a result of decreasing pressure on an upstream side of the occluder.

Clause 9. The method of any one of clauses 1-8, further comprising:

following the venous system compensation, at least partially deactivating flow restriction by the variable occluder to thereby enable retrograde blood flow from the left atrium in the coronary sinus.

Clause 10. The method of clause 9, wherein at least partially deactivating flow restriction includes:

transvascularly crossing the variable occluder with an expandable element; and compressing an occluding portion of the variable occluder against a wall of the coronary sinus.

Clause 11. The method of clause 10, wherein the expandable element includes a balloon or stent.

Clause 12. The method of clause 10, wherein the expandable element includes a stent retriever.

Clause 13. The method of any one of clauses 1-12, wherein shunting the blood flow from the left atrium into the coronary sinus includes:

transvascularly delivering a shunt; and implanting the shunt in a passageway formed between the left atrium and the coronary sinus. And implanting deflector in the coronary sinus Clause 14. The method of clause 13, wherein shunting the blood flow from the left atrium to the coronary sinus includes:

transvascularly delivering a puncturing tool to the region of the coronary sinus proximate the left atrium; and manipulating the puncturing tool to form the passageway through a wall of the coronary sinus and a wall of the left atrium.

Clause 15. The method of any one of clauses 1-14, wherein the variable occluder includes a stent and an occluding surface radially traversing the stent.

Clause 16. The method of clause 15, wherein the occluding surface includes at least one sheet of material.

Clause 17. The method of any one of clauses 1-16, further comprising:

sensing pressure upstream of the variable occluder; and increasing the level of blood flow restriction in response to a drop in upstream pressure.

Clause 18. The method of any one of clauses 1-17, further comprising:

deploying a flow deflector in the coronary sinus to deflect left atrium blood flow in a retrograde direction.

Clause 19. The method of any one of clauses 1-18, wherein the variable occluder is configured to enable simultaneous retrograde and antegrade blood flow in the coronary sinus.

Clause 20. The method of any one of clauses 1-19, further comprising:

determining the venous system compensation by comparing blood pressure in the left atrium with blood pressure upstream of the variable occluder.

Clause 21. A device for promoting venous system compensation to enable retrograde blood flow in at least a portion of the venous system of the myocardium, the device comprising:

a support configured for implantation within a coronary sinus at a location proximate a left atrium, the support being adapted to transition between a compressed state for delivery within the coronary sinus and an expanded state for fixation within the coronary sinus, the support in the expanded state including a passageway therethrough; and a variable occluder associated with the support, the variable occluder being configured to gradually increase a level of antegrade blood flow restriction through the passageway over a period of days to enable at least a portion of the venous system of the myocardium to compensate for increased pressure caused by the gradual increase in the level of antegrade blood flow restriction, wherein the variable occluder is further configured to substantially occlude antegrade blood flow through the passageway when a pressure on an upstream side of the variable occluder reaches a threshold of between 30 and 60 mmHg, and to cause retrograde flow in the at least a portion of the venous system of the myocardium on an upstream side of the variable occluder.

Clause 22. The device of clause 21, wherein the threshold is between 30 and 40 mmHg.

Clause 23. The device of clause 21 or 22, wherein the threshold is between 40 and 50 mmHg.

Clause 24. The device of any one of clauses 21-23, wherein the variable occluder includes at least one perforated sheet.

Clause 25. The device of any one of clauses 21-24, wherein the variable occluder includes at least one flap.

Clause 26. The device of clause 25, wherein the at least one flap is movable and configured to move in a manner limiting blood flow through the passageway in response to changes in the pressure on the upstream side of the variable occluder.

Clause 27. The device of clause 25 or 26, wherein the at least one flap is configured to progressively restrict antegrade blood flow through the passageway as antegrade blood flow force on the flap decreases.

Clause 28. The device of any one of clauses 25-27, wherein the at least one flap includes at least one sheet of flexible material.

Clause 29. The device of clause 28, wherein the at least one sheet includes a plurality of flexible sheets.

Clause 30. The device of any one of clauses 24-29, wherein the variable occluder further includes a flexible frame element.

Clause 31A. The device of clause 30, wherein the flexible frame element includes a discontinuous perimeter configured to allow a tool to cross through the variable occluder.

Clause 31B. The device of clause 30 or 31A, wherein the flexible frame element is associated with a flat sheet.

Clause 31C. The device of any one of clauses 30, 31A, or 31B, wherein the flexible frame is coil shaped.

Clause 32. The device of any one of clauses 21-31C, wherein the variable occluder includes material configured to promote tissue growth and thereby inhibit blood flow through the passageway.

Clause 33. The device of any one of clauses 21-23, wherein the variable occluder includes a perforated sheet extending over an opening of the passageway, and a flap configured to adhere to the opening to thereby seal the opening when the pressure on the upstream side of the variable occluder reaches the threshold.

Clause 34. The device of any one of clauses 21-33, wherein the variable occluder is further configured to be permanently disabled after the period of days to enable retrograde flow in the coronary sinus.

Clause 35. The device of any one of clauses 21-34, wherein the variable occluder is configured to be permanently disabled by a tool configured to cross the variable occluder.

Clause 36. The device of any one of clauses 21-35, wherein the variable occluder is further configured to at least partially allow blood flow passage through the passageway at a first flow volume when the pressure on the upstream side of the variable occluder is above 60 mmHg.

Clause 37. The device of clause 36, wherein the variable occluder is further configured to restrict blood flow passage through the passageway to a second flow volume less than the first flow volume when the pressure on the upstream side of the variable occluder is below 30 mmHg.

Clause 38. The device of any one of clauses 21-37, wherein the variable occluder is further configured to at least partially allow blood flow passage through the passageway at a first flow volume when the pressure on the upstream side of the variable occluder is above 50 mmHg.

Clause 39. The device of any one of clauses 21-38, wherein the variable occluder is further configured to at least partially allow blood flow passage through the passageway at a first flow volume when the pressure on the upstream side of the variable occluder is above 40 mmHg.

Clause 40. The device of any one of clauses 21-39, wherein the period of days spans weeks.

Clause 41. The device of any one of clauses 21-40, wherein the period of days spans months.

Clause 42. The device of any one of clauses 21-41, wherein the support includes a first section having a first diameter, and a second section having a second diameter greater than the first diameter.

Clause 43. The device of clause 42, wherein the second diameter is sized to hinder migration of the support in the coronary sinus, and the first diameter is configured to support the variable occluder.

Clause 44. An occlusion device for regulating an extent of occlusion over time comprising:

a support frame configured to transition between a compressed state and an expanded state, said support frame comprising a cylindrical periphery extending between a first perimeter end and a second perimeter end to define a central lumen; and an occlusive assembly having an occlusive sheet or set thereof which extends across the central lumen and comprises a passage with an adjustable size or area.

Clause 45. The occlusion device of clause 44, wherein the occlusive assembly is configured to:

provide a pressure gradient-dependent extent of occlusion of a vein or size of a passage when a first pressure gradient is above a first threshold value (e.g., 45 mmHg);

substantially decrease an extent of occlusion or an area of the passage such that there is minimal area to no passage when a second pressure gradient is below a second threshold value (e.g., 35 mmHg); and enable tool-crossing, independent of a pressure gradient.

Clause 46. The occlusion device of clause 44 or 45, wherein the occlusive assembly enables tool-crossing, independent of a pressure gradient and comprises any one or both of the following:

an occlusive sheet having a passage, said passage being configured to increase an extent of occlusion over time within a vein as a pressure gradient decreases; and a flap extending from an occlusive sheet and sized to cover a passage, said flap configured to transition from: a. a passage-uncovered state at a first timepoint or wherein a first pressure gradient is above a first threshold value to b. a passage-covering state at a second timepoint or wherein a second pressure gradient is below a second threshold value.

Clause 47. The occlusion device of any one of clauses 44-46, wherein the occlusive assembly enables tool-crossing, independent of a pressure gradient and comprises both of the following: an occlusive sheet having a passage and a flap extending from an occlusive sheet and sized to cover a passage, said flap configured to transition from a bent state at a first timepoint or under a first pressure gradient above a first threshold value to a planar state at a delayed timepoint or under a second pressure gradient below a second threshold value.

Clause 48. The occlusion device of clause 47, wherein said passage is configured to transition from an open state at a first timepoint or under a first pressure gradient above a first threshold value to a closed or decrease area state at a delayed timepoint or under a second pressure gradient below a second threshold value.

Clause 49. The occlusion device of any one of clause 45-48, wherein the first threshold is 40 mmHg, 45 mmHg, 50 mmHg, 55 mmHg, or 60 mmHg and the second threshold is 40 mmHg, 35 mmHg, 30 mmHg, 25 mmHg or 20 mmHg and wherein the second threshold is less than first threshold.

Clause 50. The occlusion device of clause 49, wherein the passage is configured to at least partially open or be uncovered above a first threshold and close or be covered by a flap below the second threshold.

Clause 51. The occlusion device of any one of clauses 44-50, wherein the occlusive sheet forms a planar surface.

Clause 52. The occlusion device of any one of clauses 44-51, wherein the occlusive sheet or set thereof is associated with a central or proximal perimeter of the support frame and extends across a circular base thereof.

Clause 53. The occlusion device of any one of clauses 44-52, wherein the occlusive sheet or set thereof is associated with the first perimeter end and extends across the central lumen.

Clause 54. The occlusion device of any one of clauses 44-53, wherein the occlusive sheet is at least partially impermeable and preferably fully impermeable.

Clause 55. The occlusion device of any one of clauses 44-54, wherein the occlusive sheet is configured to increase an extent of occlusion over time within a vein.

Clause 56. The occlusion device of any one of clauses 44-55, wherein the occlusive sheet comprises no reinforcement.

Clause 57. The occlusion device of any one of clauses 44-56, wherein the expanded state of the support frame is sized and shaped to expand radially and engage an inner surface of a vessel.

Clause 58. The occlusion device of any one of clauses 44-57, wherein the expanded state of the support frame is sized and shaped to expand radially without engaging an inner surface of a vessel, and wherein stabilization within the vein is by an alternative means.

Clause 59. The occlusion device of any one of clauses 44-58, wherein the support frame is covered with an additional layer for surface smoothing or improved contact with an inner vessel wall.

Clause 60. The occlusion device of any one of clauses 45-59, wherein the vessel is a vein.

Clause 61. The occlusion device of any one of clauses 44-60, wherein a ratio between an axial length of a support frame and a diameter of the sheet is between about 0.5 to 1.5.

Clause 62. The occlusion device of any one of clauses 44-61, wherein a passage is configured to open and close based on an elastic mechanism, mechanical mechanism or a combination thereof.

Clause 63. The occlusion device of clause 62, wherein a passage is configured to open and close based on an elastic mechanism.

Clause 64. The occlusion device of clause 62, wherein a passage is configured to open and close based on a mechanical mechanism.

Clause 65. The occlusion device of any one of clauses 44-64, wherein the passage is positioned at a central position within the occlusive sheet or is positioned proximate to first perimeter end of the occlusion device.

Clause 66. The occlusion device of clause 65, wherein an occlusive sheet is affixed to the first perimeter end and further comprises one or more passages in the occlusive sheet.

Clause 67. The occlusion device of any one of clauses 44-66, wherein the passage is formed by affixing a set of occlusive sheets to the first perimeter end, said set of occlusive sheets extending from opposite sides towards a center where they separate from one another to form a passage above a first threshold value (e.g., 40 mmHg or 45 mmHg) and overlap to limit or close a passage when a second pressure gradient is below a second threshold value (e.g., 35 mmHg).

Clause 68. The occlusion device of any one of clauses 44-67, wherein the passage is centrally positioned relative to the first perimeter of the support frame.

Clause 69. The occlusion device of any one of clauses 44-68, wherein the passage is configured to increase an extent of occlusion over time within a vein.

Clause 70. The occlusion device of clause 69, wherein the passage is configured to promote tissue growth.

Clause 71. The occlusion device of any one of clauses 44-70, wherein the passage is a slit.

Clause 72. The occlusion device of clause 71, wherein the slit has a perimeter with a degree of elasticity such that it is adapted to expand above the first threshold.

Clause 73. The occlusion device of clause 72, wherein a slit perimeter has a degree of elasticity which is distinct or increased compared with the elasticity at a perimeter edge of the occlusive sheet.

Clause 74. The occlusion device of any one of clauses 71-73, wherein the slit has a length of less than 70%, less than 50%, less than 40%, less than 30% or less than 20% of a diameter of the occlusive sheet.

Clause 75. The occlusion device of any one of clauses 71-74, wherein the slit in the occlusive sheet is further covered by a flap.

Clause 76. The occlusion device of clause 75, wherein a flap extends from the occlusive sheet to cover a passage, said flap being configured to transition between a planar state and a less than planar state.

Clause 77. The occlusion device of clause 75 or 76, wherein the flap is configured to adhere to the occlusive sheet after a period of time and/or at a threshold pressure.

Clause 78. The occlusion device of any one of clauses 75-77, wherein the flap is further reinforced.

Clause 79. The occlusion device of any one of clauses 75-78, wherein a condition-dependent connection drives the transition between a planar and bent states of the flap.

Clause 80. The occlusion device of any one of clauses 75-79, wherein a condition-dependent connection is composed of a material which degrades after a defined period of time or is sensitive to mechanical strain, magnetic field or chemical degradation.

Clause 81. The occlusion device of any one of clauses 44-80, wherein the set of occlusive sheets comprises a static occlusive sheet secured to the first perimeter end and a pivotable occlusive sheet secured to an opposing end of the first perimeter end and further configured to alter a passage size.

Clause 82. The occlusion device of clause 81, wherein two semi-circular frames are each associated with an occlusive sheet via a frame connector or extension and wherein each of said semi-circular frames are adapted to have a frame-open or pivot away from a coplanar position relative to the first perimeter when a first pressure gradient is above a first threshold value (e.g., 45 mmHg); and have a frame closed or coplanar position relative to the first perimeter when a second pressure gradient is below a second threshold value (e.g., 35 mmHg).

Clause 83. The occlusion device of any one of clauses 44-82, wherein the occlusion device further comprises a skirt on an inner surface of the support frame.

Clause 84. The occlusion device of any one of clauses 44-83, further comprising a frame coupler connecting between the support frame and a stabilizing frame.

Clause 85. The occlusion device of any one of clauses 44-84, wherein a stabilizing frame is configured to exert a radially outward force against an interior wall of a vessel in the expanded state.

Clause 86. A binary occlusion device for intraluminal delivery within a vessel, comprising:

a stabilizing frame having a compressed state and an expanded state, said expanded state being tubular to radially engage a vessel, define a first central lumen having a first diameter, extend between a second perimeter end and a first perimeter end and being further associated with a frame coupler;

a support frame configured to transition between a compressed state and an expanded state, said support frame defining a cylindrical periphery of a second central lumen having a second diameter and extending between a first perimeter end and a second perimeter end; said first perimeter end at least partially associated with an occlusive assembly configured to a. substantially decrease an area of a passage such that there is minimal to no passage when said occlusive assembly is under a second pressure gradient below a second threshold value (e.g., 35 mmHg); and enable tool-crossing, independent of a pressure gradient; and a frame coupler connecting between the support frame and the stabilizing frame.

Clause 87. The binary occlusion device of clause 86, wherein a ratio between an axial length of the support frame or between the first and second perimeter ends, and the diameter of a sheet is between about 0.3 to 0.5.

Clause 88. The occlusion device of clause 86 or 87, wherein the expanded state of the support frame is sized and shaped to expand radially without engaging an inner surface of a vessel.

Clause 89. A method of providing intraluminal occlusion, comprising:

providing an occlusive sheet secured to a perimeter of an expandable tubular frame which engages an inner wall of a vessel to provide an occluding surface and a passage;

enabling blood flow at a first pressure gradient above a first threshold while occluding a majority of a vein at a second pressure gradient below a second threshold;

and passing or crossing the occlusive sheet with a tool at a delayed timepoint.

Clause 90. The method of clause 89, wherein the method further comprises a time-dependent mechanism which closes the passage at a delayed timepoint prior to cross with a tool.

Clause 91. The method of clause 89 or 90, wherein the method further comprises a time-dependent decrease in the first or second threshold.

Clause 92. The method of any one of clauses 89-91, wherein the occlusive sheet is secured to a first perimeter end.

Clause 93. A method of gradually transitioning to retrograde flow within a coronary sinus comprising:

occluding blood flow within a coronary sinus at a location adjacent to a left heart chamber, waiting a period of time to meet specific criteria; and connecting between a left heart chamber and the coronary sinus to delivery oxygen rich blood from the left chamber to the venous system.

Clause 94. The method of clause 93, wherein the left heart chamber is a left atrium.

Clause 95. The method of clause 93 or 94, wherein the specific criteria is more than 2 weeks.

Clause 96. The method of any one of clause 93-95, wherein the specific criteria is a pressure less than the left atrium pressure.

Clause 97. The method of any one of clause 93-96, wherein the specific criteria is a pressure of less than 40 mmHg.

Disclosed embodiments may include any one of the following bullet-pointed features alone or in combination with one or more other bullet-pointed features, whether implemented as a system, device, and/or method.

a method for causing retrograde oxygenated blood flow in at least a portion of the venous system of the myocardium implanting a variable occluder in a coronary sinus region proximate a left atrium a variable occluder configured to gradually increase a level of blood flow restriction over a period of days to enable a venous system of the myocardium to compensate for increased pressure caused by the gradual increase in the level of blood flow restriction following venous system compensation, shunting oxygenated blood flow into the coronary sinus to cause retrograde flow of oxygenated blood in at least a portion of the venous system of the myocardium to thereby enable revascularization of the myocardium shunting oxygenated blood flow into the coronary sinus from the left atrium a variable occluder configured for transvascular delivery in a compressed state for implantation in the coronary sinus via expansion in the region of the left atrium a variable occluder configured such that the gradual increase in the level of blood flow restriction occurs over a period of weeks a variable occluder configured such that the gradual increase in the level of blood flow restriction occurs over a period of months a variable occluder configured to gradually increase the level of blood flow restriction as a function of time a variable occluder configured to gradually increase the level of blood flow restriction as a function of pressure a variable occluder configured such that the level of blood flow restriction increases as a result of decreasing pressure on an upstream side of the occluder following venous system compensation, at least partially deactivating flow restriction by a variable occluder to thereby enable retrograde blood flow from the left atrium in the coronary sinus at least partially deactivating flow restriction includes transvascularly crossing a variable occluder with an expandable element at least partially deactivating flow restriction includes compressing an occluding portion of a variable occluder against a wall of the coronary sinus an expandable element includes a balloon an expandable element includes a stent an expandable element includes a stent retriever shunting the blood flow from the left atrium into the coronary sinus includes transvascularly delivering a shunt shunting the blood flow from the left atrium into the coronary sinus includes implanting the shunt in a passageway formed between the left atrium and the coronary sinus shunting the blood flow from the left atrium to the coronary sinus includes transvascularly delivering a puncturing tool to the region of the coronary sinus proximate the left atrium shunting the blood flow from the left atrium to the coronary sinus includes manipulating the puncturing tool to form the passageway through a wall of the coronary sinus and a wall of the left atrium a variable occluder includes a stent a variable occluder includes an occluding surface radially traversing a stent an occluding surface includes at least one sheet of material sensing pressure upstream of the variable occluder increasing a level of blood flow restriction in response to a drop in upstream pressure deploying a flow deflector in the coronary sinus to deflect left atrium blood flow in a retrograde direction a variable occluder configured to enable simultaneous retrograde and antegrade blood flow in the coronary sinus determining venous system compensation by comparing blood pressure in the left atrium with blood pressure upstream of the variable occluder a device for promoting venous system compensation to enable retrograde blood flow in at least a portion of the venous system of the myocardium a support configured for implantation a support configured for implantation within a coronary sinus at a location proximate a left atrium a support adapted to transition between a compressed state for delivery within the coronary sinus and an expanded state for fixation within the coronary sinus a support in an expanded state including a passageway therethrough a variable occluder a variable occluder associated with the support a variable occluder configured to gradually increase a level of antegrade blood flow restriction through the passageway over a period of days to enable the at least a portion of the venous system of the myocardium to compensate for increased pressure caused by the gradual increase in the level of antegrade blood flow restriction a variable occluder is further configured to substantially occlude antegrade blood flow through the passageway when a pressure on an upstream side of the variable occluder reaches a threshold a variable occluder configured to substantially occlude antegrade blood flow through the passageway when a pressure on an upstream side of the variable occluder reaches a threshold of between 30 and 60 mmHg a variable occluder configured to cause retrograde flow in the at least a portion of the venous system of the myocardium on an upstream side of the variable occluder an occlusion threshold for a variable occluder between 30 and 40 mmHg an occlusion threshold for a variable occluder between 40 and 50 mmHg a variable occluder includes at least one perforated sheet a variable occluder includes at least one flap a variable occluder includes at least movable one flap at least one flap of an occluder is configured to move in a manner limiting blood flow through the passageway at least one flap of a variable occluder is configured to move in a manner limiting blood flow through a passageway in response to changes in the pressure on the upstream side of the variable occluder at least one flap of a variable occluder is configured to progressively restrict antegrade blood flow through a passageway as antegrade blood flow force on the flap decreases at least one flap of a variable occluder includes at least one sheet of flexible material a plurality of flexible sheets in a variable occluder a flexible frame element of a variable occluder a variable occluder includes material configured to promote tissue growth and thereby inhibit blood flow through the passageway a variable occluder includes a perforated sheet extending over an opening of the passageway a variable occluder includes a flap configured to adhere to the opening to thereby seal the opening when the pressure on the upstream side of the variable occluder reaches the threshold a variable occluder configured to be permanently disabled after the period of days to enable retrograde flow in the coronary sinus a variable occluder configured to be permanently disabled by a tool configured to cross the variable occluder a flexible frame element includes a discontinuous perimeter configured to allow a tool to cross through the variable occluder a variable occluder configured to at least partially allow blood flow passage through the passageway at a first flow volume when the pressure on the upstream side of the variable occluder is above 60 mmHg a variable occluder configured to restrict blood flow passage through the passageway to a second flow volume less than the first flow volume when the pressure on the upstream side of the variable occluder is below 30 mmHg a variable occluder configured to at least partially allow blood flow passage through a passageway at a first flow volume when the pressure on the upstream side of the variable occluder is above 50 mmHg a variable occluder configured to at least partially allow blood flow passage through a passageway at a first flow volume when the pressure on the upstream side of the variable occluder is above 40 mmHg a variable occluder that adjusts over a period of weeks a variable occluder that adjusts over a period of months a support of a variable occluder includes a first section having a first diameter, and a second section having a second diameter greater than the first diameter a second diameter of a variable occluder is sized to hinder migration of the support in the coronary sinus a first diameter of a variable occluder is configured to support the variable occluder Other embodiments will be apparent from consideration of the specification and practice of the embodiments disclosed herein. It is intended that the specification and examples be considered as example only, with a true scope and spirit of the disclosed embodiments being indicated by the following claims. It is also intended that the sequence of steps shown in figures are only for illustrative purposes and are not intended to be limited to any particular sequence of steps. As such, those skilled in the art can appreciate that these steps can be performed in a different order while implementing the same method.

What is claimed is:

1. A device for promoting venous system compensation to enable retrograde blood flow in at least a portion of the venous system of the myocardium, the device comprising:

a support configured for implantation within a coronary sinus at a location proximate a left atrium, the support being adapted to transition between a compressed state for delivery within the coronary sinus and an expanded state for fixation within the coronary sinus, the support in the expanded state including a passageway therethrough; and a variable occluder associated with the support, the variable occluder being configured to gradually increase a level of antegrade blood flow restriction through the passageway over a period of days to enable at least a portion of the venous system of the myocardium to compensate for increased pressure caused by the gradual increase in the level of antegrade blood flow restriction, wherein the variable occluder is further configured to substantially occlude antegrade blood flow through the passageway when a pressure on an upstream side of the variable occluder reaches a threshold, and to cause retrograde flow in the at least a portion of the venous system of the myocardium on an upstream side of the variable occluder.

2. The device of claim 1, wherein the threshold is between 20 and 30 mmHg.

3. The device of claim 1, wherein the threshold is between 30 and 40 mmHg.

4. The device of claim 1, wherein the variable occluder includes at least one perforated sheet.

5. The device of claim 1, wherein the variable occluder includes at least one flap.

6. The device of claim 5, wherein the at least one flap is movable and configured to move in a manner limiting blood flow through the passageway in response to changes in the pressure on the upstream side of the variable occluder.

7. The device of claim 5, wherein the at least one flap is configured to progressively restrict antegrade blood flow through the passageway as antegrade blood flow force on the flap decreases.

8. The device of claim 5, wherein the at least one flap includes at least one sheet of flexible material.

9. The device of claim 8, wherein the at least one sheet includes a plurality of flexible sheets.

10. The device of claim 4, wherein the variable occluder further includes a flexible frame element.

11. The device of claim 10, wherein the flexible frame element includes a discontinuous perimeter configured to allow a tool to cross through the variable occluder.

12. The device of claim 10, wherein the flexible frame element is associated with a flat sheet.

13. The device of claim 10, wherein the flexible frame is coil shaped.

14. The device of claim 1, wherein the variable occluder includes material configured to promote tissue growth and thereby inhibit blood flow through the passageway.

15. The device of claim 1, wherein the variable occluder includes a perforated sheet extending over an opening of the passageway, and a flap configured to adhere to the opening to thereby seal the opening when the pressure on the upstream side of the variable occluder reaches the threshold.

16. The device of claim 1, wherein the variable occluder is further configured to be permanently disabled after the period of days to enable retrograde flow in the coronary sinus.

17. The device of claim 1, wherein the variable occluder is configured to be permanently disabled by a tool configured to cross the variable occluder.

18. The device of claim 1, wherein the variable occluder is further configured to at least partially allow blood flow passage through the passageway at a first flow volume when the pressure on the upstream side of the variable occluder is above 60 mmHg.

19. The device of claim 18, wherein the variable occluder is further configured to restrict blood flow passage through the passageway to a second flow volume less than the first flow volume when the pressure on the upstream side of the variable occluder is below 30 mmHg.

20. The device of claim 1, wherein the variable occluder is further configured to at least partially allow blood flow passage through the passageway at a first flow volume when the pressure on the upstream side of the variable occluder is above 50 mmHg.

21. The device of claim 1, wherein the variable occluder is further configured to at least partially allow blood flow passage through the passageway at a first flow volume when the pressure on the upstream side of the variable occluder is above 40 mmHg.

22. The device of claim 1, wherein the period of days spans weeks.

23. The device of claim 1, wherein the period of days spans months.

24. The device of claim 1, wherein the support includes a first section having a first diameter, and a second section having a second diameter greater than the first diameter.

25. The device of claim 24, wherein the second diameter is sized to hinder migration of the support in the coronary sinus, and the first diameter is configured to support the variable occluder.

26. The device of claim 18, wherein the variable occluder is further configured to restrict blood flow passage through the passageway to a second flow volume less than the first flow volume when the pressure on the upstream side of the variable occluder is below 20 mmHg.

* * * * *